US009387239B2

(12) United States Patent
Zollinger et al.

(10) Patent No.: US 9,387,239 B2
(45) Date of Patent: Jul. 12, 2016

(54) MENINGOCOCCAL MULTIVALENT NATIVE OUTER MEMBRANE VESICLE VACCINE, METHODS OF MAKING AND USE THEREOF

(75) Inventors: Wendell David Zollinger, Silver Spring, MD (US); Mikhail Donets, North Potomac, MD (US); Deborah Schmiel, Rockville, MD (US); Boris Ionin, Potomac, MD (US); Ryan Marques, Rockville, MD (US); Elizabeth Ellen Moran, Wheaton, MD (US)

(73) Assignee: U.S. ARMY MEDICAL RESEARCH AND MATERIEL COMMAND, Fort Detrick, MD (US)

( * ) Notice: Subject to any disclaimer, the term of this patent is extended or adjusted under 35 U.S.C. 154(b) by 154 days.

(21) Appl. No.: 12/995,268

(22) PCT Filed: Jun. 1, 2009

(86) PCT No.: PCT/US2009/045818
§ 371 (c)(1),
(2), (4) Date: Mar. 9, 2011

(87) PCT Pub. No.: WO2009/158142
PCT Pub. Date: Dec. 30, 2009

(65) Prior Publication Data
US 2011/0182942 A1 Jul. 28, 2011

Related U.S. Application Data

(60) Provisional application No. 61/057,462, filed on May 30, 2008.

(51) Int. Cl.
A61K 39/095 (2006.01)
A61K 39/00 (2006.01)
C12N 1/36 (2006.01)

(52) U.S. Cl.
CPC .............. *A61K 39/095* (2013.01); *C12N 1/36* (2013.01); *A61K 2039/522* (2013.01); *A61K 2039/55505* (2013.01); *A61K 2039/55561* (2013.01); *A61K 2039/55572* (2013.01)

(58) Field of Classification Search
CPC ... A61K 39/02; A61K 39/095; A61K 39/116; A61K 39/385; A61K 39/39; A61K 47/26; A61K 9/08; A61P 31/00; A61P 31/04; A61P 37/04; C12N 1/20; C12N 1/21; C12N 1/36; C12N 15/00; C12N 15/01; C12N 15/74; C07K 14/22
See application file for complete search history.

(56) References Cited

U.S. PATENT DOCUMENTS

| 4,601,903 | A | 7/1986 | Frasch |
| 4,727,136 | A | 2/1988 | Jennings et al. |
| 5,705,161 | A | 1/1998 | Van Der Ley et al. |
| 6,476,201 | B1 | 11/2002 | Lowell et al. |
| 6,558,677 | B2 | 5/2003 | Zollinger et al. |
| 6,821,521 | B1 | 11/2004 | Robinson et al. |
| 6,921,537 | B2 | 7/2005 | Zlotnick |
| 7,112,332 | B1 | 9/2006 | Lowell |
| 7,238,345 | B1 * | 7/2007 | Seid et al. ............ 424/93.2 |
| 7,384,645 | B2 | 6/2008 | Foster et al. |
| 2002/0037295 | A1 | 3/2002 | Lowell |
| 2003/0059444 | A1 | 3/2003 | Zollinger |
| 2003/0180316 | A1 | 9/2003 | Boutriau |
| 2003/0215469 | A1 | 11/2003 | Robinson |
| 2004/0047880 | A1 | 3/2004 | De Bolle |
| 2004/0126389 | A1 | 7/2004 | Berthet |
| 2004/0131625 | A1 | 7/2004 | Berthet |
| 2004/0131642 | A1 | 7/2004 | Rosenqvist |
| 2005/0013831 | A1 | 1/2005 | Foster |
| 2006/0034854 | A1 | 2/2006 | Berthet |
| 2006/0047106 | A1 | 3/2006 | Pavliak et al. |
| 2006/0088553 | A1 | 4/2006 | Braun |
| 2006/0216307 | A1 | 9/2006 | Berthet |
| 2006/0240045 | A1 | 10/2006 | Berthet et al. |
| 2007/0031449 | A1 | 2/2007 | Bos |
| 2007/0166333 | A1 | 7/2007 | Niebla Perez |
| 2007/0196391 | A1 | 8/2007 | O'Hagan |
| 2008/0063665 | A1 | 3/2008 | Oster |
| 2008/0138359 | A1 * | 6/2008 | Steeghs et al. ........... 424/196.11 |
| 2008/0233154 | A1 | 9/2008 | Berthet |
| 2008/0248065 | A1 | 10/2008 | Granoff |
| 2009/0117147 | A1 | 5/2009 | Berthet |
| 2009/0123499 | A1 * | 5/2009 | Devos et al. .............. 424/250.1 |

FOREIGN PATENT DOCUMENTS

| WO | 9006696 | 6/1990 |
| WO | 9201791 | 2/1992 |
| WO | 9303761 | 3/1993 |
| WO | 9931132 | 6/1999 |
| WO | 9955873 | 11/1999 |
| WO | 0025811 | 5/2000 |
| WO | 0050074 | 8/2000 |
| WO | 0109350 | 2/2001 |
| WO | 2001009350 | 8/2001 |
| WO | 0191788 | 12/2001 |
| WO | 0209746 | 2/2002 |
| WO | 03051379 | 6/2003 |
| WO | 2004014417 | 2/2004 |
| WO | 2004014419 | 2/2004 |
| WO | 2005042571 | 5/2005 |
| WO | 2006024946 | 3/2006 |
| WO | 2006081259 | 8/2006 |
| WO | 2007144316 A2 | 12/2007 |

OTHER PUBLICATIONS

Van der Ley et al. Vaccine 13: 401-407, 1995, abstract.*
Aho et al., Mol. Microbiol., 5:1429-1437 (1991).
Barenkamp et al., Infect. Immun., 60:1302-1313 (1992).
Barlow et al., Infect. Immun., 55(11):2734-2740 (1987).
Comanducci et al., J. Exp. Med., 195:1445-1454 (2002).

(Continued)

*Primary Examiner* — S. Devi
(74) *Attorney, Agent, or Firm* — McAndrews, Held & Malloy, Ltd.

(57) ABSTRACT

The present technology provides vaccine compositions comprising native outer membrane vesicles (NOMVs) from at least one genetically modified strain of *Neisseria* which provides protective immunity to meningococcal disease, more preferably subtype B meningococcal disease. The present technology further provides methods of immunizing an animal or human against meningococcal disease comprising administering the vaccine composition of the present invention.

10 Claims, 18 Drawing Sheets

(56) References Cited

OTHER PUBLICATIONS

Frosch et al., Mol. Microbiol., 4(7):1215-1218 (1990).
Grass et al., Infect. Immun., 69:307-314 (2001).
Hendrixson et al., Mol. Cell, 2:841-850 (1998).
Hou et al., J. Infect. Dis., 192:580-590 (2005).
Legrain et al., Gene, 130(1):73-80 (1993).
Van der Ley et al., Vaccine 13:401-407 (1995).
McGuinness et al., J. Exp. Med., 171:1871-1882 (1990).
Nassif et al., J. Bacteriol., 173(7):2147-2154 (1991).
Peak et al., FEMS Immunol. Med. Microbiol., 28:329-334 (2000).
Poolman et al., J. Med. Microbiol., 19:203-209 (1985).
Sierra et al., NIPH Ann., 14(2):195-207 (1991).
St. Geme et al., J. Bacteriol., 182:6005-6013 (2000).
St. Geme et al., Mol. Microbiol., 14:217-233 (1994).
Swartley et al., J. Bacteriol., 176(5):1530-1534 (1994).
International Search Report and Written Opinion, Int'l Appln. No. PCT/US09/45818, filed Jun. 1, 2009.
Katial et al. "Immunogenicity and Safety Testing of a Group B Intranasal Meningocca Membrane Vesicle Vaccine" Infection and Immunity Feb. 2002, vol. 70, No. 2, pp. 702-707.
Zollinger et al. "Development of a vaccine for Neisseria Meningitidis Group B Based on Membrane Vesicles", Public report in Online information for the Defense Community, Jan. 10, 2006, http://www.dtic.mil/cgi-bin/GetTRDoc/Location=U2&doc=GetTRDoc.pdf&AD=ADA481545.
Fisseha et al. "Characterization of Native Outer Membrane Vesicles from IpxL Mutant Strains of Neisseria meningitidis for Use in Parenteral Vaccination", Infection and Immunity, Jul. 2005, vol. 73, No. 7, pp. 4070-4080.
M. Fisseha et al, "Characterization of native outer membrane vesicles from IpxL mutant strains of Neisseria meningitids for use in parenteral vaccination", Infection and Immunity, vol. 73, No. 7, Jul. 1, 2005, pp. 4070-4080.
Koeberling Oliver et al. "Bactericidal antibody response elicited by a vaccine with overexpressed factor H-bidning protein and genetically attenuated endotoxin", Journal of Infectious Diseases, JID, University of Chicago Press, Chicago IL, vol. 198, No. 2, May 27, 2008.
Holst J., "Strategies for development of universal vaccines against meningococcal serogroup B disease: The most promising options and the challenges evaluating them," Human Vaccines, Landes Bioscience, Georgetown, TX, US, vol. 3, No. 6, Nov. 1, 2007.
Van Berkel et al. "A critical contributionof both CD28 and ICOS in the adjuvant activity of Neisseria meningitidis H44/76 LPS and IpxL1 LPS", Vaccine, Elsevier LTD, GB, vol. 25, No. 24, May 24, 2007.
Giuliani Marzia M. et al. "A universal vaccine for serogroup B meningococcus" PNAS, National Academy of Sciences, vol. 103, No. 29, Jul. 18, 2006.
Van Der Ley et al. "Construction of Neisseria Meningitidis strains carrying multiple chromosomal copies of the porA gene for use in the production of a multivalent outer membrane vesicle vaccine", Vaccine, vol. 14, No. 4, Jan. 1, 1995.
Menende et al. "Recent advances in the pathogenic neisseria research" Biotechnologia Aplicada 2008 ELFOS Scientia Cub, vol. 25, No. 3, 2008.
Extended European Search Report for Application No. 09770677.4-142 (PCT/US2009045818); Oct. 14, 2013.

* cited by examiner

Master Cell Bank Preparation

Production Cell Bank Preparation

Fermentation

FIGURE 4

Purification of Native Outer Membrane Vesicles

```
┌─────────────────────────────────────┐
│ 8570 HOPS-G Cell Paste, Lot # 1267, │
│ 500 gm                              │
└─────────────────────────────────────┘
                 ↓
```

Thaw the cell paste at 2-8°C for 18-24 hr and suspend the cells in 4 volumes of buffer containing 0.01 M Tris-HCl, 0.15 M NaCl, 0.001 M EDTA pH 7.5.

↓

*First Extraction*
Warm the cell suspension at 56 ± 3°C for 30 min; cool; shear in a Waring blender for 3 min at high speed; centrifuge at 23,600 x g for 20 min, 4 ± 2°C; retain supernatant as extract 1; re-extract pellets.

↓

*Second Extraction*
Suspend pellets in 0.01 M Tris-HCl, pH 7.5, 37 ± 3°C; shear in a Waring blender for 3 min at high speed; centrifuge at 23,600 x g for 20 min, 4 ± 2°C; retain supernatant as extract 2; re-extract pellets.

↓

Centrifuge combined ~~extracts at 23,600 x g for~~ 20 min, 4 ± 2°C; discard pellets and retain supernatant containing extracted membrane vesicles. Store overnight at 2-8°C. Prior to further processing, centrifuge at 4200xg max for 15 min at 2-8°C and discard the small white pellets → Visual inspection of combined supernatant by PI to determine, based on turbidity, that the yield from the 2 extractions is adequate.

↓

Add 100X MgCl$_2$ to 15 mM final concentration. Add Benzonase (nuclease) to 100 units per ml and stir at 20 ±5° C for 60-80 min.

↓

Preparation of Native Outer Membrane Vesicles (Continued)
( Room 3 , Bldg. 501)

Lot No. 1289

FIGURE 8

IDENTITY TEST WITH MONOCLONAL ANTIBODIES
Meningococcal 8570 HOPS-G NOMV Vaccine, BPR-779-00, Lot No. 1289

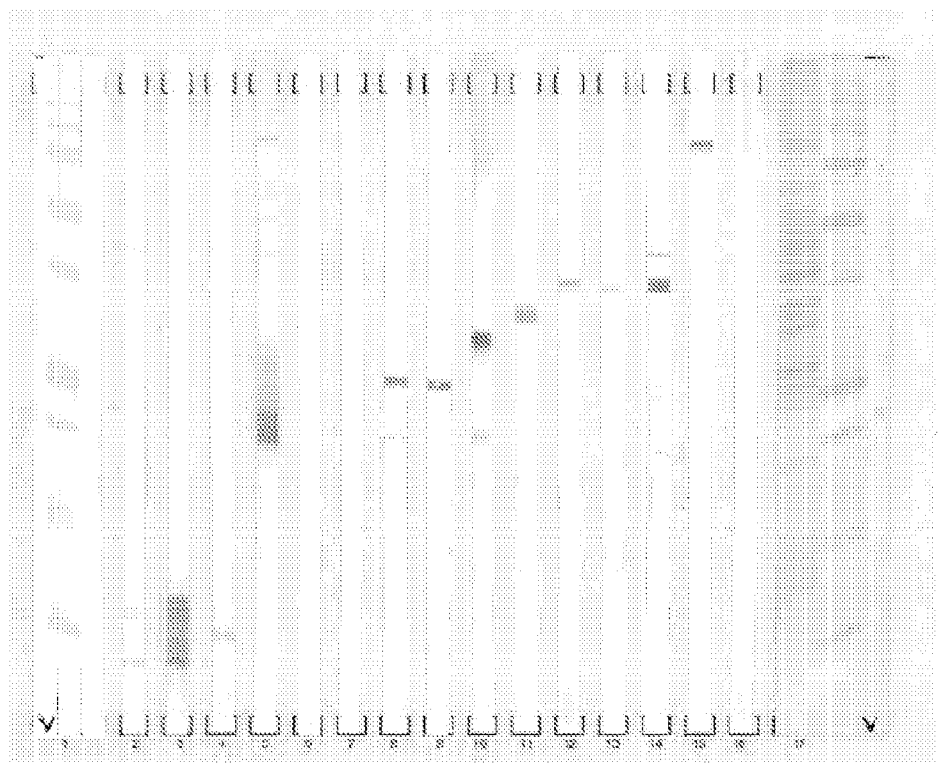

| Lane | Antibody Specificity | Monoclonal Antibody | Expected Reaction | Test Result |
|------|---------------------|---------------------|-------------------|-------------|
| 1 | Pre-stained Standard | NA | | |
| 2 | L8 LOS | 2-1 L8 | Trace | Trace |
| 3 | L8v LOS | 25-1-LC1 | Positive | Positive |
| 4 | L3,7 LOS | 9-2-L379 | Trace | Trace |
| 5 | Lip (H8) | 2-1-CA2 | Positive | Positive |
| 6 | Opa P5.10 | 23-1-P5.10 | Negative | Negative |
| 7 | Opa P5.11 | MF7-1-P5.11 | Negative | Negative |
| 8 | Opc (P5.C) | B306-P5C | Positive | Positive |
| 9 | FHBP 1 (GNA1870) | JAR 4 | Positive | Positive |
| 10 | Rmp | 9F5 | Positive | Positive |
| 11 | PorB P4 | 15-1-P4 | Positive | Positive |
| 12 | PorA P1.14 | MN21G3.17 | Positive | Positive |
| 13 | PorA P1.15 | MN3C5C | Positive | Positive |
| 14 | PorA P1.19 | 2-1-P1.19 | Positive | Positive |
| 15 | TBP2 | 476C2G2 | Positive | Positive |
| 16 | Group B Polysaccharide | 2-2-B | Negative | Negative |
| 17 | Amido Black Stain | NA | | |

IL-6 Release from Whole Human Blood Following Incubation with Different Concentrations of NOMV Vaccines TNF-α Release by Whole Human Blood Following Incubation with Different
Concentrations of Vaccine Lot 1289 or DOC-extracted OMV from strain 44/76.

Vaccine Groups:

1) 0.1 µg
2) 0.3 µg 3) 1.0 µg
4) 3.0 µg 5) 0.1 µg + REHYRDAGEL® LV
6) 0.3 µg + REHYRDAGEL® LV 7) 1.0 µg + REHYRDAGEL® LV
8) 3.0 µg + REHYRDAGEL® LV
9) 1.0 µg + REHYRDAGEL® HPA

FIGURE 17

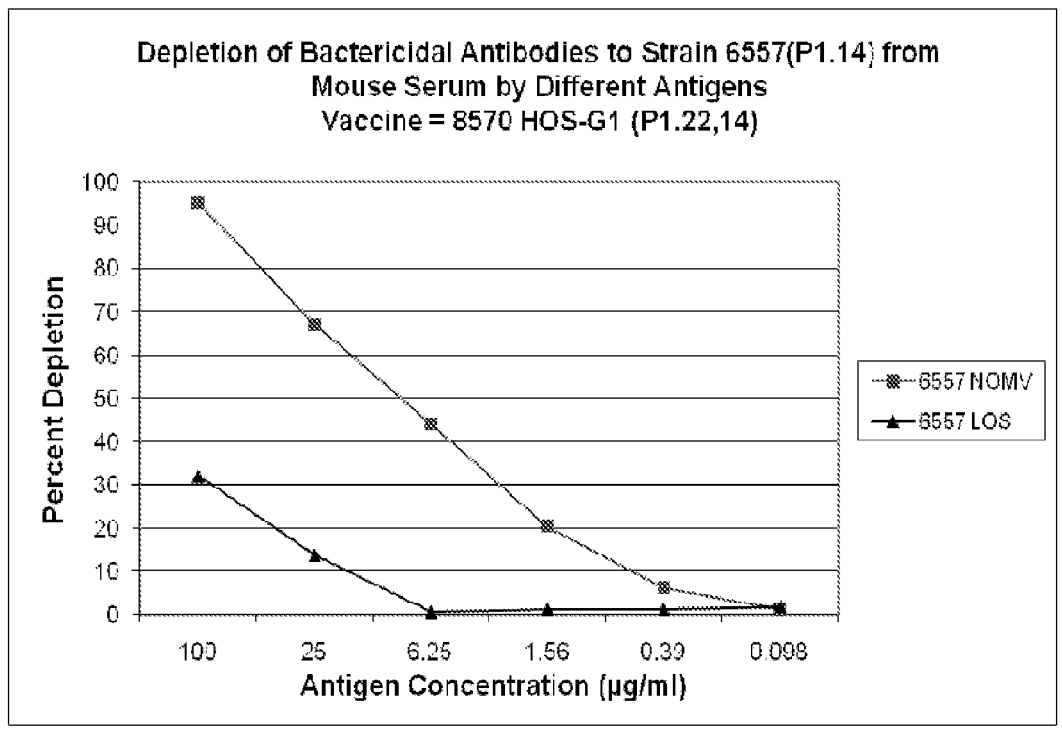

FIGURE 18

Strain B1

*Parent*
H44/76
B:15:P1.7,16:L3,7
ET-5 Clone
PorB3
TbpB isotype II

*Mutations*
synX deletion
lpxL1 deletion
Add 2nd PorA (P1.7-1.1)
Over express NadA
Stable expression of L8-3 LOS and Opc

Strain B2

*Parent*
8570
B:4:P1.19,15:L(3,7)-5
ET-5 Clone
PorB3
TbpB isotype II

*Mutations*
synX deletion
lpxL1 deletion
Add 2nd PorA (P1.22,14)
Over express fHbp (v.1)
Stable expression of L8-5 LOS and Opc

Strain B3

*Parent*
B16B6
B:2a:P1.5,2:L2
ET-37 Clone
PorB2
TbpB isotype I

*Mutations*
synX deletion
lpxL1 deletion
Add 2nd PorA (P1.22-1,4)
Over express fHbp(v.2)
Stable expression of L8-2

FIGURE 20
A.
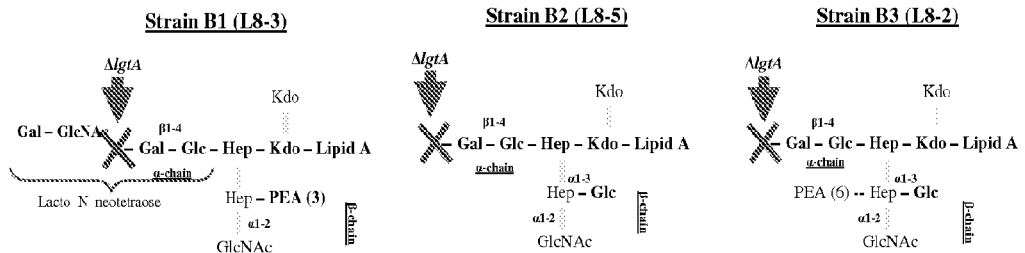
B.
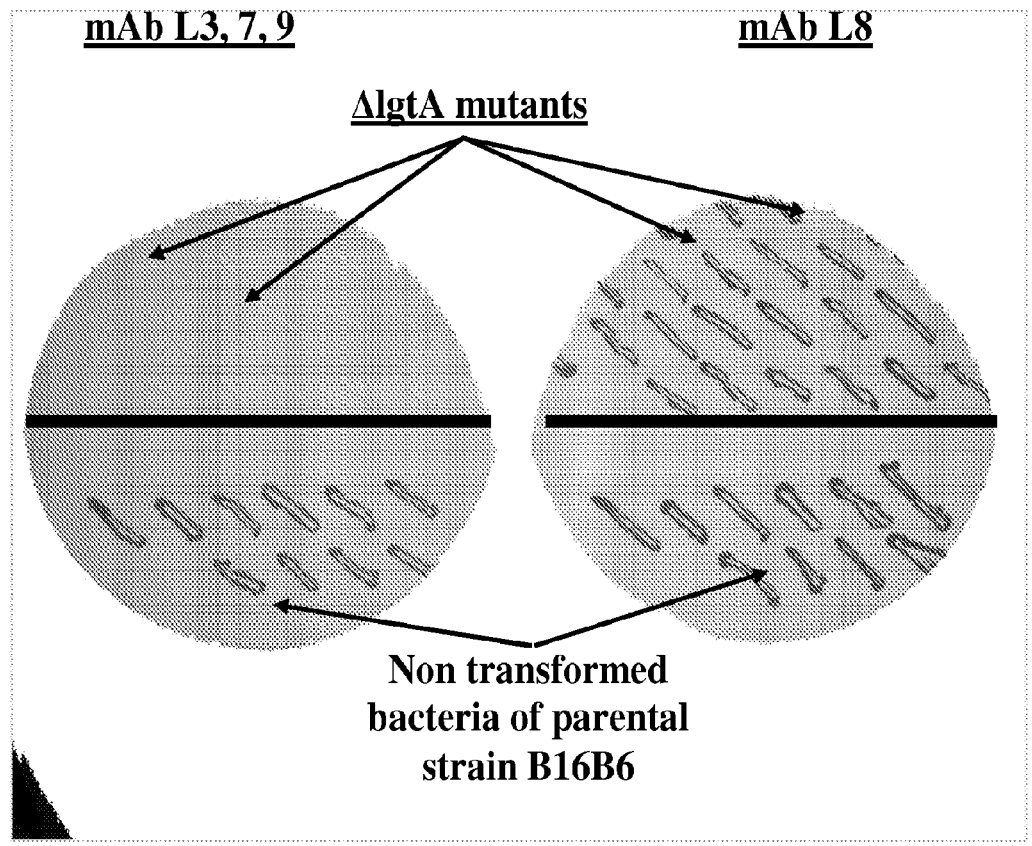

FIGURE 21
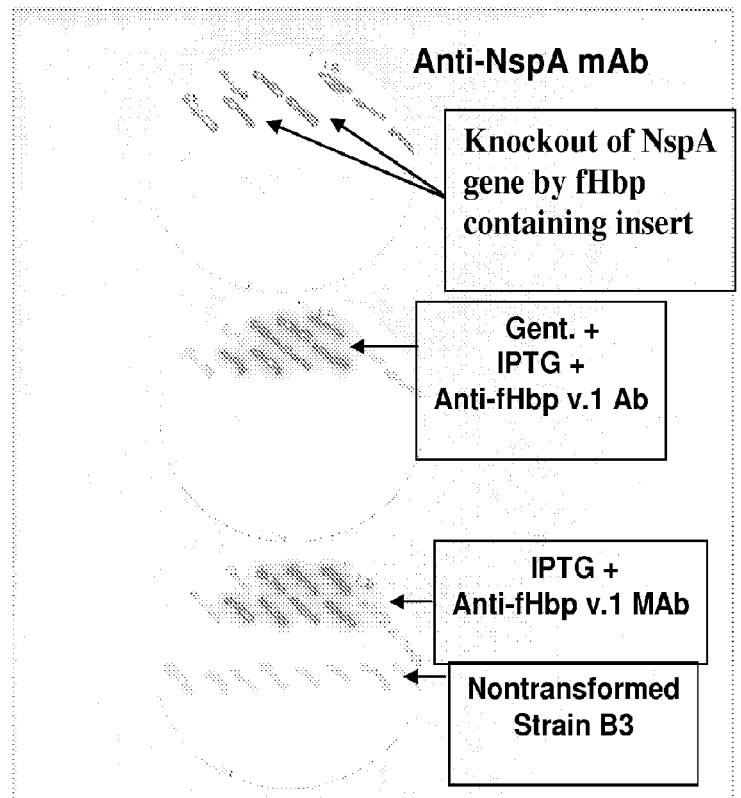
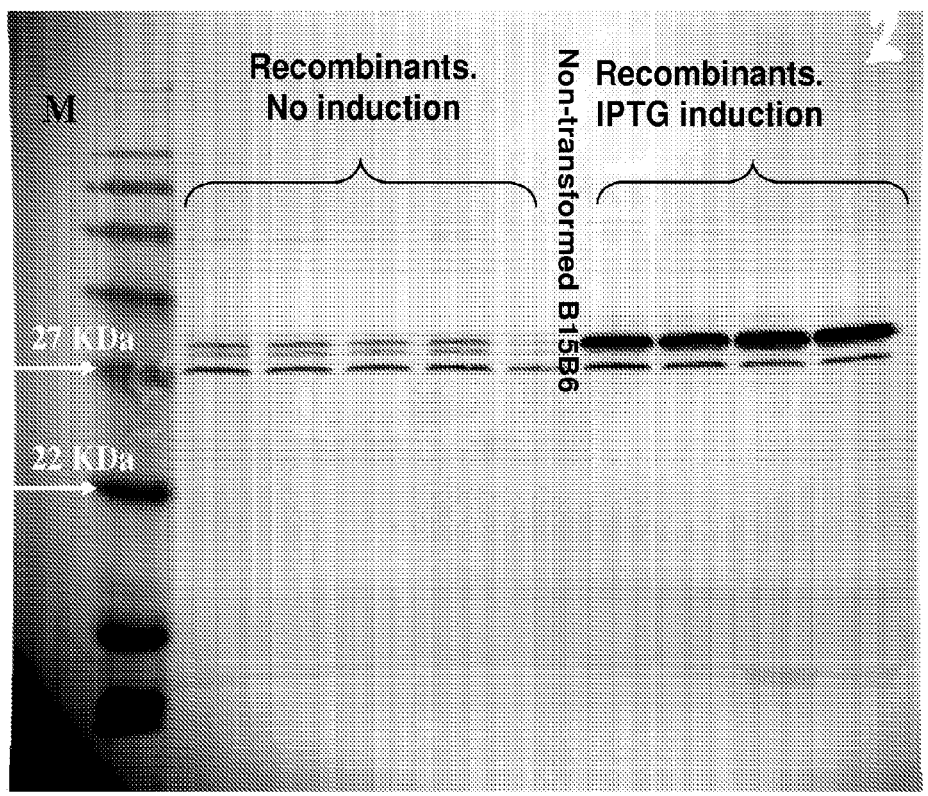

SEQUENCE LISTING

<160> NUMBER OF SEQ ID NOS: 10

<210> SEQ ID NO 1
<211> LENGTH: 108
<212> TYPE: DNA
<213> ORGANISM: Neisseria meningitidis
<220> FEATURE:
<221> NAME/KEY: misc_feature
<223> OTHER INFORMATION: promoter region of opcA gene of Neisseria meningiditis
<220> FEATURE:
<221> NAME/KEY: misc_feature
<222> LOCATION: (93)..(104)
<223> OTHER INFORMATION: poly-G sequence

<400> SEQUENCE: 1

```
catagttaaa acctctaaaa tttggattgt agtcggatat ggtaacataa cgtaaataat     60
cgttacgctt acaattatat tcttaagctt tcgggggggg ggggattt                 108
```

<210> SEQ ID NO 2
<211> LENGTH: 109
<212> TYPE: DNA
<213> ORGANISM: Artificial Sequence
<220> FEATURE:
<223> OTHER INFORMATION: promoter region of opcA gene of Neisseria meningiditis
<220> FEATURE:
<221> NAME/KEY: misc_feature
<222> LOCATION: (93)..(104)
<223> OTHER INFORMATION: replacement sequence for poly-G sequence
<220> FEATURE:
<221> NAME/KEY: misc_feature
<222> LOCATION: (95)..(102)
<223> OTHER INFORMATION: Not I restriction site

<400> SEQUENCE: 2

```
catagttaaa acctctaaaa tttggattgt agtcggatat ggtaacataa cgtaaataat     60
cgttacgctt acaattatat tcttaagctt tcgcgcggcc gcgcatttt                109
```

<210> SEQ ID NO 3
<211> LENGTH: 38
<212> TYPE: DNA
<213> ORGANISM: Artificial Sequence
<220> FEATURE:
<223> OTHER INFORMATION: promoter region of PorA of Neisseria meningiditis
<220> FEATURE:
<221> NAME/KEY: misc_feature
<222> LOCATION: (12)..(25)
<223> OTHER INFORMATION: poly-G sequence

<400> SEQUENCE: 3

```
ggtttttttg cggggggggg gggggtataa ttgaagac                             38
```

<210> SEQ ID NO 4
<211> LENGTH: 2940
<212> TYPE: DNA
<213> ORGANISM: Artificial Sequence
<220> FEATURE:
<223> OTHER INFORMATION: plasmid pOpc-79 for insertion of sequence into promoter of opc of Neisseria meningiditis

<400> SEQUENCE: 4

```
ctgcagattg ttttttacga cggggaagtt ggcaaagaaa tagcccgcgt aagaaaacag     60
gataacccac aacaagccac cgatgatgtt gtagcggata aatttggcat agtgcatttt    120
ccccataccg gcgacgaagg gggcgaaggt gcggacgatg ggcataaaac gggcaatgat    180
```

```
gatggttttg ccgccgtgtt tttcgtaaaa acggtgggtt ttatcgagat attcacgtcg    240
gaagatttta gaatcggggt tggcgaacag cctgccgccg aaatatttgc cgacggtaaa    300
attgagcgcg tcgccgagta tggcggcaag gcttaataat gcaaccatca aatgaatatc    360
cataccgccc agcgcggcaa tcccgccggc ggcaaacagc agcgaatcgc cgggcagtaa    420
gggcgtaaca atcaggccgg tttcgcaaaa aacaatcaaa aacagaatcg cataaatcca    480
cacaccgtat tgcgccgaca gcgcgagcag gtgttggtcg atatggagga tgaagtcgat    540
ggcggaggca agcacggcgc gttcctaaaa aaacaaaccg cgtattttaa ccgattggaa    600
aaatgccgtc tgaaaagttt cagacggcat cggctattca aattcatttc acgtaaaaac    660
cgcaaaccaa aatagtttgc ggtttggcat ttaaagtgac aatgatgatt tcaaatcatc    720
agaattttat gccgacgcgc aagccgtatt cacgaatact ggttttcggg atggtgagcg    780
atacgtcgcc actcttggtt gttacactaa actcgccgga ttctttgtaa gtgcgttgtt    840
tgtagaacgg ccccgcctcg atgctggcgg attcgcccag ttttttacca atatttgcac    900
ccaatccaaa gccccagccg ttggtttttt gattgatgtc ttttttgaga ttggtaacgc    960
cggtgtttaa tttatagcgg gaattgaggt caaatttcac ttcagaccaa gggttgatat   1020
accagccgtt acccagttgg gaaagcaaat ccgcgtgaac tttggctaac cacgactgac   1080
ggctgctgtg aagcgtatgc ttggtggttt taatgctgtc ttttgaagat tcaaaaccca   1140
agccggcacc cacacggaaa tttaaagaat cacttaacgt tgggtgtag gtgtagcctg   1200 tgtaaagatc gatacggttt tcaggaacgc cggtgggcag ttttacattt ttagtcttac   1260
ccagcttgtt ctcatctgtt tccaaattaa taatattttt tttgctgcgc ccgaaaccgg   1320
cttccaagcg gatgccttgg ttggcatcaa aaggaatatc agcacgcacg ctgatgtgtt   1380 tggcagctttt gtgtttttct ttcaggaaag cacgagttga agaaatggaa gagaggtcgg   1440
tgtggacggt aaactcatta gcggtttgaa gctcttgtgc agcggcggca gtaccggtca   1500
gggcaatcat ggcacatgta aaaactgttt ttttcatagt taaaacctct aaaatttgga   1560
ttgtagtcgg atatggtaac ataacgtaaa taatcgttac gcttacaatt atattcttaa   1620
gctttcgcgc ggccgcgcat tttacatata ttaataaaaa ttaacaaata gttatttgtt   1680
tacaacgaat tgttattctc acttggtttt ctgtttttta tgggaatgac gaaattttag   1740
tttgtgtgta tttatcggaa aaacagaaac ccgccgccgt cattcccgcg caggcgggaa   1800
tctagaaccc aacgcgacaa aaatttatcc gaagcgacaa caatcttttc atcgtcattc   1860
ccgcgcaggc gggaatctag aacgtaaaat ctaaagaaac cgttttaccc gataagtttc   1920
cgtgccgaca aacctagatt cccgcctgcg cgggaatgac gggattttag gtttctgatt   1980
tcggttttct gttttaaggg aatgacgaga cttgagatgg cggcatttat cgggagcaac   2040
tgaaaccacc ctgccgtcat tcccgcgaaa gcgggaatct aggttcgtcc ggtttcggtt   2100
atttccgata gattcctgcc gcgttggggg tctggattcc cgcctgcgcg ggaatgacgg   2160
gactttaggt ttctgttttt gtttgagacc tttgcaaaat tcctttccct cccgacagcc   2220
gaaacccaaa cacaggtttt cggctgtttt cgccccaaat accgcctaat tttacccaaa   2280
taccccctta atcctccccg gatacccgat aatcaggcat ccgggctgcc ttttaggcgg   2340
cagcgggcgc acttaacctg ttggccgctt tcaacaggtt caaacacatc gccttcaggt   2400
ggctttgcgc actcactttta atcagtccga aataggctgc ccgcgcatag cggaatttac   2460
ggtgcagcgt accgaagctc tgttcgacca catatagtgg attaaattta aaccagtacg   2520
gcgttgcctc gccttgccgt actatttgta ctgtctgcgg cttcgtcgcc ttgtcctgat   2580
```
ttaaatttaa tccactataa cgggtcttcg ataaatatcg gttacgtttg gtttgcgttt 2640
ccgtcagcgg acggttgcgg caggctttgc gcataatgcc gtccaacaac tgatgttctt 2700
ccagatgttg ccggttttcc gcactgtcat agcctttgtc ggcatagacg gtcgtacctt 2760
tgggcagtcc ttccaacaaa ggcggcaggt gtttgcactc atgggcattg gcgggggtaa 2820
tgtgcagttt ctcgatatag ccttccgcat cggtacgggt atgttgtttg taaccgagtt 2880
tgtagaggcc gtttttcttg atccaacggg catcgctgtc cttactcggt gtggtttggc 2940

<210> SEQ ID NO 5
<211> LENGTH: 3341
<212> TYPE: DNA
<213> ORGANISM: Artificial Sequence
<220> FEATURE:
<223> OTHER INFORMATION: Plasmid pMN5 for insertion sequence used for knockout of lpxL1 (also called htrB) gene of Neisseria meningiditis

<400> SEQUENCE: 5
ctgcagaaac cgtattgtct gcctcgcgga cgggaatggc gggtatcact tttgcatttg 60
caagcgcggc aatgcggctc aatccggtaa tcgttgccgt ctgaataccg aaaaaatcca 120
caaaaaccga atcgttgcgt ccgaaatcct gatcgggcag atacagaaac ggcgcgctgc 180
ttttgcggaa ctgtttgacg agggcgcgca gcccttcggt gcgcccgata aggaagacgt 240
tgtgatagcg gttgcggcct ttcaaaatct gttcgtccaa tatcttgttt ttttgatggg 300
aatacatact gatcagcggg atatcctgat taagcgcgta caccgccatc tcgaacgcgg 360
tgaagtgcgg atacaggatg atgacacgcg tttgtaatca tgtactcttt ttgataaaaa 420
attggagatt cctttacaaa tatgctctta cgtgctatta tttaagtgac tatttaaaag 480
gagttaataa atatgcggca aggtattctt aaataaactg tcaatttgat agcgggaaca 540
aataattaga tgtccttttt taggagggct tagtttttttg tacccagttt aagaatacct 600
ttatcatgtg attctaaagt atccagagaa tatctgtatg ctttgtatac ctatggttat 660
gcataaaaat cccagtgata aaagtattta tcactgggat ttttatgccc ttttgggttt 720
ttgaatggag gaaaatcaca tgaaaattat taatattgga gttttagctc atgttgatgc 780
aggaaaaact accttaacag aaagcttatt atataacagt ggagcgatta cagaattagg 840
aagcgtggac aaaggtacaa cgaggacgga taatacgctt ttagaacgtc agagaggaat 900
tacaattcag acaggaataa cctcttttca gtgggaaaat acgaaggtga acatcataga 960
cacgccagga catatggatt tcttagcaga agtatatcgt tcattatcag ttttagatgg 1020
ggcaattcta ctgatttctg caaaagatgg cgtacaagca caaactcgta tattgtttca 1080
tgcacttagg aaaatgggga ttcccacaat ctttttttatc aataagattg accaaaatgg 1140
aattgattta tcaacggttt atcaggatat taaagagaaa ctttctgccg aaattgtaat 1200
caaacagaag gtagaactgt atcctaatat gtgtgtgacg aactttaccg aatctgaaca 1260
atgggatacg gtaatagagg gaaatgatga cctttttagag aaatatatgt ccggtaaatc 1320
attagaagca ttggaactcg aacaagagga aagcataaga tttcataatt gttccctgtt 1380
ccctgtttat cacggaagtg caaaaaacaa tatagggatt gataacctta tagaagtgat 1440
tacgaataaa ttttattcat caacacatcg aggtccgtct gaactttgcg gaaatgtttt 1500
caaaattgaa tatacaaaaa aaagacaacg tcttgcatat atacgccttt atagtggagt 1560
actacattta cgagattcgg ttagagtatc agaaaaagaa aaaataaaag ttacagaaat 1620
gtatacttca ataaatggtg aattatgtaa gattgataga gcttattctg gagaaattgt 1680

| | |
|---|---|
| tattttgcaa aatgagtttt tgaagttaaa tagtgttctt ggagatacaa aactattgcc | 1740 |
| acagagaaaa agaattgaaa atccgcatcc tctactacaa ataactgttg aaccgagtaa | 1800 |
| acctgaacag agagaaatgt tgcttgatgc ccttttggaa atctcagata gtgatccgct | 1860 |
| tctacgatat tacgtggatt ctacgacaca tgaaattata ctttctttct tagggaaagt | 1920 |
| acaaatggaa gtgattagtg cactgttgca agaaaagtat catgtggaga tagaactaaa | 1980 |
| agagcctaca gtcatttata tggagagacc gttaaaaaat gcagaatata ccattcacat | 2040 |
| cgaagtgccg ccaaatcctt tctgggcttc cattggttta tctgtatcac cgcttccgtt | 2100 |
| gggaagtgga atgcagtatg agagctcggt ttctcttgga tacttaaatc aatcatttca | 2160 |
| aaatgcagtt atggaaggga tacgctatgg ttgcgaacaa ggattatatg gttggaatgt | 2220 |
| gacggaatgt aaaatctgtt ttaagtatgg cttatactat agccctgtta gtaccccagc | 2280 |
| agattttcgg atgcttgctc ctattgtatt ggaacaagtc ttaaaaaaag ctggaacaga | 2340 |
| attgttagag ccatatctta gttttaaaat ttatgcgcca caggaatatc tttcacgagc | 2400 |
| atacaacgat gctcctaaat attgtgcgaa catcgtagac actcaattga aaaataatga | 2460 |
| ggtcattctt agtggagaaa tccctgctcg gtgtattcaa gaatatcgta gtgatttaac | 2520 |
| tttctttaca aatggacgta gtgtttgttt aacagagtta aaagggtacc atgttactac | 2580 |
| cggtgaacct gtttgccagc cccgtcgtcc aaatagtcgg atagataaag tacgatatat | 2640 |
| gttcaataaa ataacttagt gtattttatg ttgttatata aatatggttt cttgttaaat | 2700 |
| aagatgaaat attttttaat aaagatttga attaaagtgt aaaggaggag atagttatta | 2760 |
| taaactacaa gtggatattg tgtcctgtat gtggaaataa aacacgatta agataagggg | 2820 |
| aagatactga attaaaaatt ccccctctat tgtccgaaat gcagacaaga aaatttaatt | 2880 |
| gaaataaagc agttcaaagt aactgtgatt acagagccag acgcaaagac gcagagccga | 2940 |
| taaaatgaga ttaatacaat ctcattttta tcggctcttt ccgttatgta tggattcttt | 3000 |
| taacgcgtca gaaactgcaa aacatacagt acaaaaaata taaatttcat ctcgatacac | 3060 |
| attttctttt cagacggcaa aatacaaatg ccgtctgaaa ctattgaaac ctgccgcgct | 3120 |
| tgacctgcat ccccgaagga ttgagtttgg cggcaagccc gtggttgcgt aaggcgtggg | 3180 |
| tcagcgcgac ggcaagaccg tccgccgcat ccggctgggg cgttcccgaa agtcccaaca | 3240 |
| tctgcaccac catatgctgc acctgttctt ttgccgcctt gcccttgccg actaccgcct | 3300 |
| gtttgacctg ctttcagacg gtccatccat cacactgcag g | 3341 |

<210> SEQ ID NO 6
<211> LENGTH: 7687
<212> TYPE: DNA
<213> ORGANISM: Artificial Sequence
<220> FEATURE:
<223> OTHER INFORMATION: plasmid pBE-101 for expression of fHBP variant
      1 of Neisseria meningiditis

<400> SEQUENCE: 6

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accataaaatt cgagctcgac cgtctgaaac ggcggcaaag ccgttaaccc gcgcgttgcc | 240 |
| tttaaatggt ggcggcggca tcacgcgcg gatgggtgaa acttgcaaac ggtttggaaa | 300 |
| aaacagcggt atctgtcgga ttgttgcagg tgcaggcata cggttttgtg tgcgtctgtg | 360 |

```
ccttaagcgt cggacatttc cggcggcggc tgtgccgtct gaaacgcccg gcggggatg    420
cggctgcgtt ttccatcgat aagcatattt tccggacgcg ttcggggcgg ttttcccgg    480
gcggccgccg atttgtttgc gcttatatag tggattaaca aaaatcagga caaggcgacg    540
aagccgcaga cagtacaaat agtacggaac cgattcactt ggtgcttcag caccttagag    600
aatcgttctc tttgagctaa ggcgaggcaa cgccgtactg ttttttgtta atccactata    660
aaaaacactg cagcaaatcg tttaaaaaca agcgtccttt ttcggtcggg cggaatacgg    720
cagggtcggt ttccagcagg cctttttgcc ttgccgtttc gatttgcgcc atgattttgg    780
cactcggtac gcccgtgcgc tcctgcaaca tcgcggcggg tacgccgtcg gtcaggcgca    840
gggcgttcat catgaattcg aacggcaaat cttcggcagc gacggttttg cgttcgacgg    900
cttcactcgg ttggctttgc attaaggcga ggtagtcgtt ggggtggcgg cggcggacgg    960
tgcgctcgat gcggtcggga taggaaattt tgccgtgcgc gcccgcgcct atgcctaaat    1020
aatcgccgaa ctgccagtag ttcaaattgt ggcggcactg catggctggt ttcgcaaaag    1080
ccgatgtttc gtagtggaca aaacccgcgc cttccagcgc gccgtgtacc gcgtcttcga    1140
tgtcgagggc ggcttcgtct gcggcaaac cttccggcgg cgtatgaccg aacggcgtgt    1200
tcggttccat cgtcaggtga tacgcgctga tgtgggttgc gcccgtaggg atcccgactt    1260
cgctgctgcc caaggttgcc gggtgacgca caccgtggaa acggatgaag gcacgaaccc    1320
agttgacata agcctgttcg gttcgtaaac tgtaatgcaa gtagcgtatg cgctcacgca    1380
actggtccag aaccttgacc gaacgcagcg gtggtaacgg cgcagtggcg gttttcatgg    1440
cttgttatga ctgtttttt gtacagtcta tgcctcgggc atccaagcag caagcgcgtt    1500
acgccgtggg tcgatgtttg atgttatgga gcagcaacga tgttacgcag cagcaacgat    1560
gttacgcagc agggcagtcg ccctaaaaca aagttaggtg gctcaagtat gggcatcatt    1620
cgcacatgta ggctcggccc tgaccaagtc aaatccatgc gggctgctct tgatctttc    1680
ggtcgtgagt tcggagacgt agccacctac tcccaacatc agccggactc cgattacctc    1740
gggaacttgc tccgtagtaa gacattcatc gcgcttgctg ccttcgacca agaagcggtt    1800
gttggcgctc tcgcggctta cgttctgccc aggtttgagc agccgcgtag tgagatctat    1860
atctatgatc tcgcagtctc cggcgagcac cggaggcagg gcattgccac cgcgctcatc    1920
aatctcctca gcatgaggc caacgcgctt ggtgcttatg tgatctacgt gcaagcagat    1980
tacggtgacg atcccgcagt ggctctctat acaaagttgg gcatacggga agaagtgatg    2040
cactttgata tcgacccaag taccgccacc taacaattcg ttcaagccga gatcggcttc    2100
ccggccgcgg aatgccgatt tcttcttcca gcaatttgat ttgtttggag atgccgggtt    2160
gcgaagtaaa caaggcttcg gccgcttcgg aaacgttcag gttgtgctgg taaacttcta    2220
aggcgtattt caattgccga caccatcgaa tggtgcaaaa cctttcgcgg tatggcatga    2280
tagcgcccgg aagagagtca attcagggtg gtgaatgtga aaccagtaac gttatacgat    2340
gtcgcagagt atgccggtgt ctcttatcag accgtttccc gcgtggtgaa ccaggccagc    2400
cacgtttctg cgaaaacgcg ggaaaaagtg gaagcggcga tggcggagct gaattacatt    2460
cccaaccgcg tggcacaaca actggcgggc aaacagtcgt tgctgattgg cgttgccacc    2520
tccagtctgg ccctgcacgc gccgtcgcaa attgtcgcgg cgattaaatc tcgcgccgat    2580
caactgggtg ccagcgtggt ggtgtcgatg gtagaacgaa gcggcgtcga agcctgtaaa    2640
gcggcggtgc acaatcttct cgcgcaacgc gtcagtgggc tgatcattaa ctatccgctg    2700
gatgaccagg atgccattgc tgtggaagct gcctgcacta atgttccggc gttatttctt    2760
```

```
gatgtctctg accagacacc catcaacagt attattttct cccatgaaga cggtacgcga    2820
ctgggcgtgg agcatctggt cgcattgggt caccagcaaa tcgcgctgtt agcgggccca    2880
ttaagttctg tctcggcgcg tctgcgtctg gctggctggc ataaatatct cactcgcaat    2940
caaattcagc cgatagcgga acgggaaggc gactggagtg ccatgtccgg ttttcaacaa    3000
accatgcaaa tgctgaatga gggcatcgtt cccactgcga tgctggttgc caacgatcag    3060
atggcgctgg gcgcaatgcg cgccattacc gagtccgggc tgcgcgttgg tgcggatatc    3120
tcggtagtgg gatacgacga taccgaagac agctcatgtt atatcccgcc gttaaccacc    3180
atcaaacagg attttcgcct gctggggcaa accagcgtgg accgcttgct gcaactctct    3240
cagggccagg cggtgaaggg caatcagctg ttgcccgtct cactggtgaa aagaaaaacc    3300
accctggcgc caatacgca aaccgcctct ccccgcgcgt tggccgattc attaatgcag    3360
ctggcacgac aggtttcccg actggaaagc gggcagtgag cgcaacgcaa ttaatgtaag    3420
ttagctcact cattaggcac aattctcatg tttgacagct tatcatcgac tgcacggtgc    3480
accaatgctt ctggcgtcag gcagccatcg gaagctgtgg tatggctgtg caggtcgtaa    3540
atcactgcat aattcgtgtc gctcaaggcg cactcccgtt ctggataatg ttttttgcgc    3600
cgacatcata acgttctgg caaatattct gaaatgagct gttgacaatt aatcatcggc    3660
tcgtataatg tgtggaattg tgagcggata caatttcac acaggaaaca gccagtccgt    3720
ttaggtgttt tcacgagcac ttcaccaaca aggaccatag catatgaatc gaactgcctt    3780
ctgctgcctt tctctgacca ctgcccygat tctgaccgcc tgcagcagcg gaggggtgg    3840
tgtcgccgcc gacatcggtg cggggcttgc cgatgcacta accgcaccgc tcgaccataa    3900
agacaaaggt ttgcagtctt tgacgctgga tcagtccgtc aggaaaaacg agaaactgaa    3960
gctggcggca caaggtgcgg aaaaaactta tggaaacggt gacagcctca atacgggcaa    4020
attgaagaac gacaaggtca gccgtttcga ctttatccgc caaatcgaag tggacgggca    4080
gctcattacc ttggagagtg gagagttcca agtatacaaa caaagccatt ccgccttaac    4140
cgcctttcag accgagcaaa tacaagattc ggagcattcc gggaagatgg ttgcgaaacg    4200
ccagttcaga atcggcgaca tagcgggcga acatacatct tttgacaagc ttcccgaagg    4260
cggcagggcg acatatcgcg ggacggcgtt cggttcagac gatgccggcg gaaaactgac    4320
ctacaccata gatttcgccg ccaagcaggg aaacggcaaa atcgaacatt tgaaatcgcc    4380
agaactcaat gtcgacctgg ccgccgccga tatcaagccg gatggaaaac gccatgccgt    4440
catcagcggt tccgtccttt acaaccaagc cgagaaaggc agttactccc tcggtatctt    4500
tggcggaaaa gcccaggaag ttgccggcag cgcggaagtg aaaaccgtaa acggcatacg    4560
ccatatcggc cttgccgcca agcaataacg ccggtgtgcg cgtcaaattc tgatatgcgc    4620
cttattctgc aaaccgccag cttggctgtt ttggcggatg agagaagatt ttcagcctga    4680
tacagattaa atcagaacgc agaagcggtc tgataaaaca gaatttgcct ggcggcagta    4740
gcgcggtggt cccacctgac cccatgccga actcagaagt gaaacgccgt agcgccgatg    4800
gtagtgtggg gtctccccat gcgagagtag ggaactgcca ggcatcaaat aaaacgaaag    4860
gctcagtcga aagactgggc ctttcgtttt atctgttgtt tgtcggtgaa cgctctcctg    4920
agtaggacaa atccgccgcc cgggcgagcc ttcggcggtt ttgtttttctg ccaccgcaac    4980
tacacaagcc ggcggttttg tacgataatc ccgaatgctg cggcttctgc cgccctattt    5040
tttgaggaat ccgaaatgtc caaaaccatc atccacaccg acaaagcccc cgccgccatc    5100
ggcgcgtaca gccaagccgt ccgagcaggc gacaccgttt acatgagcgg tcaaatcccc    5160
```

```
ctcgatcccg ccacgatgac cgtcgtcggc aacggcgatt tccgcgccga agcgcgccaa    5220
gtgttccaaa acctgcaagc cgtcgccgaa gcggcaggcg gcacgctggc cgacatcgtc    5280
aaactcaacg cctacctgac cgacttgggc aattttgccg tcttcaacga agtcatggcg    5340
gaatttatcg ccgagcccct ccccgcccgc gccgccgtcg gcgttgcctc gctgcccaaa    5400
ggcgtgcagg tcgaagccga agccgtcctc gtgaccgtct gaaacggaag cttggcgtaa    5460
tcatggtcat agctgtttcc tgtgtgaaat tgttatccgc tcacaattcc acacaacata    5520
cgagccggaa gcataaagtg taaagcctgg ggtgcctaat gagtgagcta actcacatta    5580
attgcgttgc gctcactgcc cgctttccag tcgggaaacc tgtcgtgcca gctgcattaa    5640
tgaatcggcc aacgcgcggg gagaggcggt ttgcgtattg ggcgctcttc cgcttcctcg    5700
ctcactgact cgctgcgctc ggtcgttcgg ctgcggcgag cggtatcagc tcactcaaag    5760
gcggtaatac ggttatccac agaatcaggg gataacgcag gaaagaacat gtgagcaaaa    5820
ggccagcaaa aggccaggaa ccgtaaaaag gccgcgttgc tggcgttttt ccataggctc    5880
cgcccccctg acgagcatca caaaaatcga cgctcaagtc agaggtggcg aaacccgaca    5940
ggactataaa gataccaggc gtttccccct ggaagctccc tcgtgcgctc tcctgttccg    6000
accctgccgc ttaccggata cctgtccgcc tttctccctt cgggaagcgt ggcgctttct    6060
catagctcac gctgtaggta tctcagttcg gtgtaggtcg ttcgctccaa gctgggctgt    6120
gtgcacgaac ccccccgttca gcccgaccgc tgcgccttat ccggtaacta tcgtcttgag    6180
tccaacccgg taagacacga cttatcgcca ctggcagcag ccactggtaa caggattagc    6240
agagcgaggt atgtaggcgg tgctacagag ttcttgaagt ggtggcctaa ctacggctac    6300
actagaagga cagtatttgg tatctgcgct ctgctgaagc cagttacctt cggaaaaaga    6360
gttggtagct cttgatccgg caaacaaacc accgctggta gcggtggttt ttttgtttgc    6420
aagcagcaga ttacgcgcag aaaaaaagga tctcaagaag atcctttgat cttttctacg    6480
gggtctgacg ctcagtggaa cgaaaactca cgttaaggga ttttggtcat gagattatca    6540
aaaaggatct tcacctagat ccttttaaat taaaaatgaa gttttaaatc aatctaaagt    6600
atatatgagt aaacttggtc tgacagttac caatgcttaa tcagtgaggc acctatctca    6660
gcgatctgtc tatttcgttc atccatagtt gcctgactcc ccgtcgtgta gataactacg    6720
atacgggagg gcttaccatc tggccccagt gctgcaatga taccgcgaga cccacgctca    6780
ccggctccag atttatcagc aataaaccag ccagccggaa gggccgagcg cagaagtggt    6840
cctgcaactt tatccgcctc catccagtct attaattgtt gccgggaagc tagagtaagt    6900
agttcgccag ttaatagttt gcgcaacgtt gttgccattg ctacaggcat cgtggtgtca    6960
cgctcgtcgt ttggtatggc ttcattcagc tccggttccc aacgatcaag gcgagttaca    7020
tgatccccca tgttgtgcaa aaaagcggtt agctccttcg gtcctccgat cgttgtcaga    7080
agtaagttgg ccgcagtgtt atcactcatg gttatggcag cactgcataa ttctcttact    7140
gtcatgccat ccgtaagatg cttttctgtg actggtgagt actcaaccaa gtcattctga    7200
gaatagtgta tgcggcgacc gagttgctct tgcccggcgt caatacggga taataccgcg    7260
ccacatagca gaactttaaa agtgctcatc attggaaaac gttcttcggg gcgaaaactc    7320
tcaaggatct taccgctgtt gagatccagt tcgatgtaac ccactcgtgc acccaactga    7380
tcttcagcat cttttacttt caccagcgtt tctgggtgag caaaaacagg aaggcaaaat    7440
gccgcaaaaa agggaataag ggcgacacgg aaatgttgaa tactcatact cttcctttt    7500 caatattatt gaagcattta tcagggttat tgtctcatga gcggatacat atttgaatgt    7560
```

| | |
|---|---:|
| atttagaaaa ataaacaaat aggggttccg cgcacatttc cccgaaaagt gccacctgac | 7620 |
| gtctaagaaa ccattattat catgacatta acctataaaa ataggcgtat cacgaggccc | 7680 |
| tttcgtc | 7687 |

<210> SEQ ID NO 7
<211> LENGTH: 7687
<212> TYPE: DNA
<213> ORGANISM: Artificial Sequence
<220> FEATURE:
<223> OTHER INFORMATION: plasmid pBE-201 for additional expression of fHBP variant 2 of Neisseria meningiditis

<400> SEQUENCE: 7

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accataaatt cgagctcgac cgtctgaaac ggcggcaaag ccgttaaccc gcgcgttgcc | 240 |
| tttaaatggt ggcggcggca tcacgcggcg gatgggtgaa acttgcaaac ggtttggaaa | 300 |
| aaacagcggt atctgtcgga ttgttgcagg tgcaggcata cggttttgtg tgcgtctgtg | 360 |
| ccttaagcgt cggacatttc cggcggcggc tgtgccgtct gaaacgcccg gcggggatg | 420 |
| cggctgcgtt ttccatcgat aagcatattt tccggacgcg ttcggggcgg ttttcccgg | 480 |
| gcggccgccg atttgtttgc gcttatatag tggattaaca aaaatcagga caaggcgacg | 540 |
| aagccgcaga cagtacaaat agtacggaac cgattcactt ggtgcttcag caccttagag | 600 |
| aatcgttctc tttgagctaa ggcgaggcaa cgccgtactg gttttgttta atccactata | 660 |
| aaaaacactg cagcaaatcg tttaaaaaca agcgtccttt tcggtcggg cggaatacgg | 720 |
| cagggtcggt ttccagcagg ccttttttgcc ttgccgtttc gatttgcgcc atgattttgg | 780 |
| cactcggtac gcccgtgcgc tcctgcaaca tcgcggcggg tacgccgtcg gtcaggcgca | 840 |
| gggcgttcat catgaattcg aacggcaaat cttcggcagc gacggttttg cgttcgacgg | 900 |
| cttcactcgg ttggctttgc attaaggcga ggtagtcgtt ggggtggcgg cggcggacgg | 960 |
| tgcgctcgat gcgtcggga taggaaattt tgccgtgcgc gcccgcgcct atgcctaaat | 1020 |
| aatcgccgaa ctgccagtag ttcaaattgt ggcggcactg catggctggt ttcgcaaaag | 1080 |
| ccgatgtttc gtagtggaca aaacccgcgc cttccagcgc gccgtgtacc gcgtcttcga | 1140 |
| tgtcgagggc ggcttcgtct tgcggcaaac ctttcggcgg cgtatgaccg aacggcgtgt | 1200 |
| tcggttccat cgtcaggtga tacgcgctga tgtgggttgc gcccgtaggg atcccgactt | 1260 |
| cgctgctgcc caaggttgcc gggtgacgca caccgtggaa acggatgaag gcacgaaccc | 1320 |
| agttgacata agcctgttcg gttcgtaaac tgtaatgcaa gtagcgtatg cgctcacgca | 1380 |
| actggtccag aaccttgacc gaacgcagcg gtggtaacgg cgcagtggcg gttttcatgg | 1440 |
| cttgttatga ctgtttttttt gtacagtcta tgcctcgggc atccaagcag caagcgcgtt | 1500 |
| acgccgtggg tcgatgtttg atgttatgga gcagcaacga tgttacgcag cagcaacgat | 1560 |
| gttacgcagc agggcagtcg ccctaaaaca aagttaggtg gctcaagtat gggcatcatt | 1620 |
| cgcacatgta ggctcggccc tgaccaagtc aaatccatgc gggctgctct tgatcttttc | 1680 |
| ggtcgtgagt tcggagacgt agccacctac tcccaacatc agccggactc cgattacctc | 1740 |
| gggaacttgc tccgtagtaa gacattcatc gcgcttgctg ccttcgacca agaagcggtt | 1800 |
| gttggcgctc tcgcggctta cgttctgccc aggtttgagc agccgcgtag tgagatctat | 1860 |

```
atctatgatc tcgcagtctc cggcgagcac cggaggcagg gcattgccac cgcgctcatc    1920
aatctcctca agcatgaggc caacgcgctt ggtgcttatg tgatctacgt gcaagcagat    1980
tacggtgacg atcccgcagt ggctctctat acaaagttgg gcatacggga agaagtgatg    2040
cactttgata tcgacccaag taccgccacc taacaattcg ttcaagccga gatcggcttc    2100
ccggccgcgg aatgccgatt tcttcttcca gcaatttgat ttgtttggag atgccgggtt    2160
gcgaagtaaa caaggcttcg gccgcttcgg aaacgttcag gttgtgctgg taaacttcta    2220
aggcgtattt caattgccga caccatcgaa tggtgcaaaa cctttcgcgg tatggcatga    2280
tagcgcccgg aagagagtca attcagggtg gtgaatgtga aaccagtaac gttatacgat    2340
gtcgcagagt atgccggtgt ctcttatcag accgtttccc gcgtggtgaa ccaggccagc    2400
cacgtttctg cgaaaacgcg ggaaaaagtg gaagcggcga tggcggagct gaattacatt    2460
cccaaccgcg tggcacaaca actggcgggc aaacagtcgt tgctgattgg cgttgccacc    2520
tccagtctgg ccctgcacgc gccgtcgcaa attgtcgcgg cgattaaatc tcgcgccgat    2580
caactgggtg ccagcgtggt ggtgtcgatg gtagaacgaa gcggcgtcga agcctgtaaa    2640
gcggcggtgc acaatcttct cgcgcaacgc gtcagtgggc tgatcattaa ctatccgctg    2700
gatgaccagg atgccattgc tgtggaagct gcctgcacta atgttccggc gttatttctt    2760
gatgtctctg accagacacc catcaacagt attattttct cccatgaaga cggtacgcga    2820
ctgggcgtga agcatctggt cgcattgggt caccagcaaa tcgcgctgtt agcgggccca    2880
ttaagttctg tctcggcgcg tctgcgtctg gctggctggc ataaatatct cactcgcaat    2940
caaattcagc cgatagcgga acgggaaggc gactggagtg ccatgtccgg ttttcaacaa    3000
accatgcaaa tgctgaatga gggcatcgtt cccactgcga tgctggttgc caacgatcag    3060
atggcgctgg gcgcaatgcg cgccattacc gagtccgggc tgcgcgttgg tgcggatatc    3120
tcggtagtgg gatacgacga taccgaagac agctcatgtt atatcccgcc gttaaccacc    3180
atcaaacagg atttttcgcct gctggggcaa ccagcgtgg accgcttgct gcaactctct    3240
cagggccagg cggtgaaggg caatcagctg ttgcccgtct cactggtgaa agaaaaaacc    3300
accctggcgc ccaatacgca aaccgcctct ccccgcgcgt tggccgattc attaatgcag    3360
ctggcacgac aggtttcccg actggaaagc gggcagtgag cgcaacgcaa ttaatgtaag    3420
ttagctcact cattaggcac aattctcatg tttgacagct tatcatcgac tgcacggtgc    3480
accaatgctt ctggcgtcag gcagccatcg gaagctgtgg tatggctgtg caggtcgtaa    3540
atcactgcat aattcgtgtc gctcaaggcg cactcccgtt ctggataatg ttttttgcgc    3600
cgacatcata acggttctgg caaatattct gaaatgagct gttgacaatt aatcatcggc    3660
tcgtataatg tgtggaattg tgagcggata acaatttcac acaggaaaca gccagtccgt    3720
ttaggtgttt tcacgagcac ttcaccaaca aggaccatag catatgaatc gaactgcctt    3780
ctgctgcctt tctctgacca ctgcccygat tctgaccgcc tgcagcagcg gaggcggcgg    3840
tgtcgccgcc gacatcggcg cggggcttgc cgatgcacta accgcaccgc tcgaccataa    3900
agacaaaagt ttgcagtctt tgacgctgga tcagtccgtc aggaaaaacg agaaactgaa    3960
gctggcggca caaggtgcgg agaaaactta tggaaacggc gacagcctca atacgggcaa    4020
attgaagaac gacaaggtca gccgcttcga ctttatccgt caaatcgaag tggacgggca    4080
gctcattacc ttggagagcg gagagttcca aatatacaaa caggaccact ccgccgtcgt    4140
tgccctacag attgaaaaaa tcaacaaccc cgacaaaatc gacagcctga taaaccaacg    4200
ctccttcctt gtcagcggtt tgggcggaga acataccgcc ttcaaccaac tgcctgacgg    4260
```

```
caaagccgag tatcacggca aagcattcag ctccgacgat gctggcggaa aactgaccta    4320
taccatagat ttcgccgcca aacagggaca cggcaaaatc gaacacctga aaacacccga    4380
gcaaaatgtc gagcttgccg ccgccgaact caaagcagat gaaaaatcac acgccgtcat    4440
tttgggcgac acgcgctacg gcagcgaaga aaaaggcact taccacctcg ccctttctcgg   4500 cgaccgcgcc caagaaatcg ccggctcggc aaccgtgaag atagggggaaa aggttcacga    4560 aatcggcatc gccggcaaac agtagtaacg ccggtgtgcg cgtcaaattc tgatatgcgc    4620
cttattctgc aaaccgccag cttggctgtt ttggcggatg agagaagatt ttcagcctga    4680
tacagattaa atcagaacgc agaagcggtc tgataaaaca gaatttgcct ggcggcagta    4740
gcgcggtggt cccacctgac cccatgccga actcagaagt gaaacgccgt agcgccgatg    4800
gtagtgtggg gtctccccat gcgagagtag ggaactgcca ggcatcaaat aaaacgaaag    4860
gctcagtcga aagactgggc ctttcgtttt atctgttgtt tgtcggtgaa cgctctcctg    4920
agtaggacaa atccgccgcc cgggcgagcc ttcggcggtt ttgttttctg ccaccgcaac    4980
tacacaagcc ggcggttttg tacgataatc ccgaatgctg cggcttctgc cgccctattt    5040
tttgaggaat ccgaaatgtc caaaaccatc atccacaccg acaaagcccc cgccgccatc    5100
ggcgcgtaca gccaagccgt ccgagcaggc gacaccgttt acatgagcgg tcaaatcccc    5160
ctcgatcccg ccacgatgac cgtcgtcggc aacggcgatt ccgcgccga agcgcgccaa    5220 gtgttccaaa acctgcaagc cgtcgccgaa gcggcaggcg gcacgctggc cgacatcgtc    5280
aaactcaacg cctacctgac cgacttgggc aattttgccg tcttcaacga agtcatggcg    5340
gaatttatcg ccgagcccctt ccccgcccgc cgccgcgtcg gcgttgcctc gctgcccaaa    5400
ggcgtgcagg tcgaagccga agccgtcctc gtgaccgtct gaaacggaag cttggcgtaa    5460
tcatggtcat agctgtttcc tgtgtgaaat tgttatccgc tcacaattcc acacaacata    5520
cgagccggaa gcataaagtg taaagcctgg ggtgcctaat gagtgagcta actcacatta    5580
attgcgttgc gctcactgcc cgcttttcag tcgggaaacc tgtcgtgcca gctgcattaa    5640
tgaatcggcc aacgcgcggg gagaggcggt ttgcgtattg ggcgctcttc cgcttcctcg    5700
ctcactgact cgctgcgctc ggtcgttcgg ctgcggcgag cggtatcagc tcactcaaag    5760
gcggtaatac ggttatccac agaatcaggg gataacgcag gaaagaacat gtgagcaaaa    5820
ggccagcaaa aggccaggaa ccgtaaaaag gccgcgttgc tggcgttttt ccataggctc    5880
cgcccccctg acgagcatca caaaaatcga cgctcaagtc agaggtggcg aaacccgaca    5940
ggactataaa gataccaggc gtttccccct ggaagctccc tcgtgcgctc tcctgttccg    6000
accctgccgc ttaccggata cctgtccgcc tttctccctt cgggaagcgt ggcgctttct    6060
catagctcac gctgtaggta tctcagttcg gtgtaggtcg ttcgctccaa gctgggctgt    6120
gtgcacgaac cccccgttca gcccgaccgc tgcgccttat ccggtaacta tcgtcttgag    6180
tccaacccgg taagacacga cttatcgcca ctggcagcag ccactggtaa caggattagc    6240
agagcgaggt atgtaggcgg tgctacagag ttcttgaagt ggtggcctaa ctacggctac    6300
actagaagga cagtatttgg tatctgcgct ctgctgaagc cagttacctt cggaaaaaga    6360
gttggtagct cttgatccgg caaacaaacc accgctggta gcggtggttt ttttgtttgc    6420
aagcagcaga ttacgcgcag aaaaaaagga tctcaagaag atcctttgat cttttctacg    6480
gggtctgacg ctcagtggaa cgaaaactca cgttaaggga ttttggtcat gagattatca    6540
aaaaggatct tcacctagat ccttttaaat taaaaatgaa gttttaaatc aatctaaagt    6600
atatatgagt aaacttggtc tgacagttac caatgcttaa tcagtgaggc acctatctca    6660
```

-continued gcgatctgtc tatttcgttc atccatagtt gcctgactcc ccgtcgtgta gataactacg 6720
atacgggagg gcttaccatc tggccccagt gctgcaatga taccgcgaga cccacgctca 6780
ccggctccag atttatcagc aataaaccag ccagccggaa gggccgagcg cagaagtggt 6840
cctgcaactt tatccgcctc catccagtct attaattgtt gccgggaagc tagagtaagt 6900
agttcgccag ttaatagttt gcgcaacgtt gttgccattg ctacaggcat cgtggtgtca 6960
cgctcgtcgt ttggtatggc ttcattcagc tccggttccc aacgatcaag gcgagttaca 7020
tgatccccca tgttgtgcaa aaaagcggtt agctccttcg gtcctccgat cgttgtcaga 7080
agtaagttgg ccgcagtgtt atcactcatg gttatggcag cactgcataa ttctcttact 7140
gtcatgccat ccgtaagatg cttttctgtg actggtgagt actcaaccaa gtcattctga 7200
gaatagtgta tgcggcgacc gagttgctct tgcccggcgt caatacggga taataccgcg 7260
ccacatagca gaactttaaa agtgctcatc attggaaaac gttcttcggg gcgaaaactc 7320
tcaaggatct taccgctgtt gagatccagt tcgatgtaac ccactcgtgc acccaactga 7380
tcttcagcat cttttacttt caccagcgtt tctgggtgag caaaaacagg aaggcaaaat 7440
gccgcaaaaa agggaataag ggcgacacgg aaatgttgaa tactcatact cttccttttt 7500
caatattatt gaagcattta tcagggttat tgtctcatga gcggatacat atttgaatgt 7560
atttagaaaa ataaacaaat aggggttccg cgcacatttc cccgaaaagt gccacctgac 7620
gtctaagaaa ccattattat catgacatta acctataaaa ataggcgtat cacgaggccc 7680
tttcgtc 7687

<210> SEQ ID NO 8
<211> LENGTH: 7584
<212> TYPE: DNA
<213> ORGANISM: Artificial Sequence
<220> FEATURE:
<223> OTHER INFORMATION: plasmid pBE-311 for additional expression of NadA of Neisseria meningiditis

<400> SEQUENCE: 8
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cgagctcgac cgtctgaaac ggcggcaaag ccgttaaccc gcgcgttgcc 240
tttaaatggt ggcggcggca tcacgcggcg gatgggtgaa acttgcaaac ggtttggaaa 300
aaacagcggt atctgtcgga ttgttgcagg tgcaggcata cggttttgtg tgcgtctgtg 360
ccttaagcgt cggacatttc cggcggcggc tgtgccgtct gaaacgcccg gcgggggatg 420
cggctgcgtt ttccatcgat aagcatattt tccggacgcg ttcggggcgg gttttcccgg 480
gcggccgccg atttgtttgc gcttatatag tggattaaca aaaatcagga caaggcgacg 540
aagccgcaga cagtacaaat agtacggaac cgattcactt ggtgcttcag caccttagag 600
aatcgttctc tttgagctaa ggcgaggcaa cgccgtactg gtttttgtta atccactata 660
aaaaacactg cagcaaatcg tttaaaaaca agcgtccttt ttcggtcggg cggaatacgg 720
cagggtcggt ttccagcagg ccttttttgcc ttgccgtttc gatttgcgcc atgattttgg 780
cactcggtac gcccgtgcgc tcctgcaaca tcgcggcggg tacgccgtcg gtcaggcgca 840
gggcgttcat catgaattcg aacggcaaat cttcggcagc gacggttttg cgttcgacgg 900
cttcactcgg ttggctttgc attaaggcga ggtagtcgtt ggggtggcgg cggcggacgg 960

```
tgcgctcgat gcggtcggga taggaaattt tgccgtgcgc gcccgcgcct atgcctaaat    1020
aatcgccgaa ctgccagtag ttcaaattgt ggcggcactg catggctggt ttcgcaaaag    1080
ccgatgtttc gtagtggaca aaacccgcgc cttccagcgc gccgtgtacc gcgtcttcga    1140
tgtcgagggc ggcttcgtct tgcggcaaac cttccggcgg cgtatgaccg aacggcgtgt    1200
tcggttccat cgtcaggtga tacgcgctga tgtgggttgc gcccgtaggg atcccgactt    1260
cgctgctgcc caaggttgcc gggtgacgca caccgtggaa acggatgaag gcacgaaccc    1320
agttgacata agcctgttcg gttcgtaaac tgtaatgcaa gtagcgtatg cgctcacgca    1380
actggtccag aaccttgacc gaacgcagcg gtggtaacgg cgcagtggcg gttttcatgg    1440
cttgttatga ctgttttttt gtacagtcta tgcctcgggc atccaagcag caagcgcgtt    1500
acgccgtggg tcgatgtttg atgttatgga gcagcaacga tgttacgcag cagcaacgat    1560
gttacgcagc agggcagtcg ccctaaaaca aagttaggtg gctcaagtat gggcatcatt    1620
cgcacatgta ggctcggccc tgaccaagtc aaatccatgc gggctgctct tgatcttttc    1680
ggtcgtgagt tcggagacgt agccacctac tcccaacatc agccggactc cgattacctc    1740
gggaacttgc tccgtagtaa gacattcatc gcgcttgctg ccttcgacca agaagcggtt    1800
gttggcgctc tcgcggctta cgttctgccc aggtttgagc agccgcgtag tgagatctat    1860
atctatgatc tcgcagtctc cggcgagcac cggaggcagg gcattgccac cgcgctcatc    1920
aatctcctca gcatgaggc caacgcgctt ggtgcttatg tgatctacgt gcaagcagat    1980
tacggtgacg atcccgcagt ggctctctat acaaagttgg gcatacggga agaagtgatg    2040
cactttgata tcgacccaag taccgccacc taacaattcg ttcaagccga atcggcttc    2100 ccggccgcgg tcggactttc agataatctt tgaatattgc tgttgttcta aggtctagat    2160
tcccgcctgc gcgggaatga cgaatccatc cgcacggaaa cctgcaccac gtcattccca    2220
cgaacccaca tcccgtcatt accacgaaag tgggaatcta ggacgcaggg ttaagaaaac    2280
ctacatcccg tcattcctca aaaacagaaa accaaaatca gaaacctaaa atcccgtcat    2340
tcccgcgcag gcgggaatcc agtccgttca gtttcggtcg tttccgataa attcctgctg    2400
cttttcattt ctagattccc actttcgtgg gaatgacggc ggaagggttt tggttttttc    2460
cgataaattc ttgaggcatt gaaattctag attcccgcct gcgcgggaat gacgaatcca    2520
tccgtacgga aacctgcacc acgtcattcc taagaaccta catcccgtca ttccctcaaa    2580
aacagaaaac caaaatcaga aacctaaaat cccgtcattc ccgcgcaggc gggaatccag    2640
tccgttcagt tcggtcatt tccgataaat tcctgctgct tttcatttct agattcccac    2700
tttcgtggga atgacggcgg aagggttttg gttttttccg ataaattctt gaggcattga    2760
aattctagat tcccgcctgc gcgggaatga cggctgtaga tgcccgatgg tctttatagc    2820
ggattaacaa aaatcaggac aaggcgacga agccgcagac agtacagata gtacggaacc    2880
gattcacttg gtgcttcagc accttagaga atcgttctct ttgagctaag gcgaggcaac    2940
gccgtacttg tttttgttaa tccactataa agtgccgcgt gtgttttttt atggcgtttt    3000
aaaaagccga gactgcatcc gggcagcagc gcatcggctc gcacgaggtc tgcgcttgaa    3060
ttgtgttgta gaaacacaac gttttgaaa aaataagcta ttgttttata tcaaaatata    3120
atcattttta aaataaaggt tgcggcattt atcagatatt tgttctgaaa aatggttttt    3180
tgcggggggg ggggtataat tgaagacgta tcgggtgttt gcccgatgtt tttaggtttt    3240
tatcaaattt acaaaaggaa gccgatcata tgaaacactt tccatccaaa gtactgacca    3300
cagccatcct tgccactttc tgtagcggcg cactggcagc cacaaacgac gacgatgtta    3360
```

-continued

```
aaaaagctgc cactgtggcc attgctgctg cctacaacaa tggccaagaa atcaacggtt    3420
tcaaagctgg agagaccatc tacgacattg atgaagacgg cacaattacc aaaaaagacg    3480
caactgcagc cgatgttgaa gccgacgact ttaaaggtct gggtctgaaa aaagtcgtga    3540
ctaacctgac caaaaccgtc aatgaaaaca acaaaaacgt cgatgccaaa gtaaaagctg    3600
cagaatctga aatagaaaag ttaacaacca agttagcaga cactgatgcc gctttagcag    3660
atactgatgc cgctctggat gcaaccacca acgccttgaa taaattggga gaaaatataa    3720
cgacatttgc tgaagagact aagacaaata tcgtaaaaat tgatgaaaaa ttagaagccg    3780
tggctgatac cgtcgacaag catgccgaag cattcaacga tatcgccgat tcattggatg    3840
aaaccaacac taaggcagac gaagccgtca aaaccgccaa tgaagccaaa cagacggccg    3900
aagaaaccaa acaaaacgtc gatgccaaag taaaagctgc agaaactgca gcaggcaaag    3960
ccgaagctgc cgctggcaca gctaatactg cagccgacaa ggccgaagct gtcgctgcaa    4020
aagttaccga catcaaagct gatatcgcta cgaacaaaga taatattgct aaaaaagcaa    4080
acagtgccga cgtgtacacc agagaagagt ctgcagcaa atttgtcaga attgatggtc    4140
tgaacgctac taccgaaaaa ttggacacac gcttggcttc tgctgaaaaa tccattgccg    4200
atcacgatac tcgcctgaac ggtttggata aacagtgtc agacctgcgc aaagaaaccc    4260
gccaaggcct tgcagaacaa gccgcgctct ccggtctgtt ccaaccttac aacgtgggtc    4320
ggttcaatgt aacggctgca gtcggcggct acaaatccga atcggcagtc gccatcggta    4380
ccggcttccg ctttaccgaa aactttgccg ccaaagcagg cgtggcagtc ggcacttcgt    4440
ccggttcttc cgcagcctac catgtcgcg tcaattacga gtggtaacgc cggtgtatat    4500
cggggcggtg aagcggatag ctttgtttt gacggctcgc cttcattctt tgattgcaat    4560
ctgactgcca atctgcttca gccccaaaca aaaatccgga tacggaagaa aaacggcaat    4620
aaagacagca ataccgtct gaaagatttt cagacggtat ttcgcatttt tggcttggtt    4680
tgcacatata gtgagacctt tgcaaaaata gtctgttaac gaaatttgac gcataaaaat    4740
gcgccaaaaa atttcaatt gcctaaaacc ttcctaatat tgagcaaaaa gtaggaaaaa    4800
tcagaaaagt tttgcatttt gaaaatgaga ttgagcataa aattttagta acctatgtta    4860
ttgcaaaggt ctcgaattgt cattcccacg caggcgggaa tctagtctgg aatgctgcgg    4920
cttctgccgc cctatttttt gaggaatccg aaatgtccaa aaccatcatc cacaccgaca    4980
aagcccccgc cgccatcggc gcgtacagcc aagccgtccg agcaggcgac accgtttaca    5040
tgagcggtca atcccccctc gatcccgcca cgatgaccgt cgtcggcaac ggcgatttcc    5100
gcgccgaagc gcgccaagtg ttccaaaacc tgcaagccgt cgccgaagcg gcaggcggca    5160
cgctggccga catcgtcaaa ctcaacgcct acctgaccga cttgggcaat tttgccgtct    5220
tcaacgaagt catggcggaa tttatcgccg agcccttccc cgcccgcgcc gccgtcggcg    5280
ttgcctcgct gcccaaaggc gtgcaggtcg aagccgaagc cgtcctcgtg accgtctgaa    5340
acggaagctt ggcgtaatca tggtcatagc tgtttcctgt gtgaaattgt tatccgctca    5400
caattccaca acaatacga gccggaagca taaagtgtaa agcctggggt gcctaatgag    5460
tgagctaact cacattaatt gcgttgcgct cactgcccgc tttccagtcg ggaaacctgt    5520
cgtgccagct gcattaatga atcggccaac gcgcgggag aggcggtttg cgtattgggc    5580
gctcttccgc ttcctcgctc actgactcgc tgcgctcggt cgttcggctg cggcgagcgg    5640
tatcagctca ctcaaaggcg gtaatacggt tatccacaga atcaggggat aacgcaggaa    5700
agaacatgtg agcaaaaggc cagcaaaagg ccaggaaccg taaaaaggcc gcgttgctgg    5760
```

| | |
|---|---|
| cgtttttcca taggctccgc cccctgacg agcatcacaa aaatcgacgc tcaagtcaga | 5820 |
| ggtggcgaaa cccgacagga ctataaagat accaggcgtt tccccctgga agctccctcg | 5880 |
| tgcgctctcc tgttccgacc ctgccgctta ccggatacct gtccgccttt ctcccttcgg | 5940 |
| gaagcgtggc gctttctcat agctcacgct gtaggtatct cagttcggtg taggtcgttc | 6000 |
| gctccaagct gggctgtgtg cacgaacccc ccgttcagcc cgaccgctgc gccttatccg | 6060 |
| gtaactatcg tcttgagtcc aacccggtaa gacacgactt atcgccactg gcagcagcca | 6120 |
| ctggtaacag gattagcaga gcgaggtatg taggcggtgc tacagagttc ttgaagtggt | 6180 |
| ggcctaacta cggctacact agaaggacag tatttggtat ctgcgctctg ctgaagccag | 6240 |
| ttaccttcgg aaaagagtt ggtagctctt gatccggcaa acaaaccacc gctggtagcg | 6300 |
| gtggtttttt tgtttgcaag cagcagatta cgcgcagaaa aaaaggatct caagaagatc | 6360 |
| ctttgatctt ttctacgggg tctgacgctc agtggaacga aaactcacgt taagggattt | 6420 |
| tggtcatgag attatcaaaa aggatcttca cctagatcct tttaaattaa aaatgaagtt | 6480 |
| ttaaatcaat ctaaagtata tatgagtaaa cttggtctga cagttaccaa tgcttaatca | 6540 |
| gtgaggcacc tatctcagcg atctgtctat ttcgttcatc catagttgcc tgactccccg | 6600 |
| tcgtgtagat aactacgata cgggagggct taccatctgg ccccagtgct gcaatgatac | 6660 |
| cgcgagaccc acgctcaccg gctccagatt tatcagcaat aaaccagcca gccggaaggg | 6720 |
| ccgagcgcag aagtggtcct gcaactttat ccgcctccat ccagtctatt aattgttgcc | 6780 |
| gggaagctag agtaagtagt tcgccagtta atagtttgcg caacgttgtt gccattgcta | 6840 |
| caggcatcgt ggtgtcacgc tcgtcgtttg gtatggcttc attcagctcc ggttcccaac | 6900 |
| gatcaaggcg agttacatga tcccccatgt tgtgcaaaaa agcggttagc tccttcggtc | 6960 |
| ctccgatcgt tgtcagaagt aagttggccg cagtgttatc actcatggtt atggcagcac | 7020 |
| tgcataattc tcttactgtc atgccatccg taagatgctt ttctgtgact ggtgagtact | 7080 |
| caaccaagtc attctgagaa tagtgtatgc ggcgaccgag ttgctcttgc ccggcgtcaa | 7140 |
| tacgggataa taccgcgcca catagcagaa ctttaaaagt gctcatcatt ggaaaacgtt | 7200 |
| cttcggggcg aaaactctca aggatcttac cgctgttgag atccagttcg atgtaaccca | 7260 |
| ctcgtgcacc caactgatct tcagcatctt ttactttcac cagcgtttct gggtgagcaa | 7320 |
| aaacaggaag gcaaaatgcc gcaaaaaagg gaataagggc gacacggaaa tgttgaatac | 7380 |
| tcatactctt cctttttcaa tattattgaa gcatttatca gggttattgt ctcatgagcg | 7440 |
| gatacatatt tgaatgtatt tagaaaaata acaaataggg gttccgcgc acatttcccc | 7500 |
| gaaaagtgcc acctgacgtc taagaaacca ttattatcat gacattaacc tataaaaata | 7560 |
| ggcgtatcac gaggcccttt cgtc | 7584 |

<210> SEQ ID NO 9
<211> LENGTH: 5759
<212> TYPE: DNA
<213> ORGANISM: Artificial Sequence
<220> FEATURE:
<223> OTHER INFORMATION: plasmid pBE-501 for knockout of lgtA gene of
      Neisseria meningiditis by replacement with zeomycin gene

<400> SEQUENCE: 9

| | |
|---|---|
| cttccgcttc ctcgctcact gactcgctgc gctcggtcgt tcggctgcgg cgagcggtat | 60 |
| cagctcactc aaaggcggta atacggttat ccacagaatc aggggataac gcaggaaaga | 120 |
| acatgtgagc aaaaggccag caaaaggcca ggaa

```
ttttccatag gctccgcccc cctgacgagc atcacaaaaa tcgacgctca agtcagaggt    240
ggcgaaaccc gacaggacta taaagatacc aggcgtttcc ccctggaagc tccctcgtgc    300
gctctcctgt tccgaccctg ccgcttaccg gatacctgtc cgcctttctc ccttcgggaa    360
gcgtggcgct ttctcatagc tcacgctgta ggtatctcag ttcggtgtag gtcgttcgct    420
ccaagctggg ctgtgtgcac gaaccccccg ttcagcccga ccgctgcgcc ttatccggta    480
actatcgtct tgagtccaac ccggtaagac acgacttatc gccactggca gcagccactg    540
gtaacaggat tagcagagcg aggtatgtag gcggtgctac agagttcttg aagtggtggc    600
ctaactacgg ctacactaga agaacagtat ttggtatctg cgctctgctg aagccagtta    660
ccttcggaaa aagagttggt agctcttgat ccggcaaaca aaccaccgct ggtagcggtg    720
gtttttttgt ttgcaagcag cagattacgc gcagaaaaaa aggatctcaa gaagatcctt    780
tgatctttc tacgggtct gacgctcagt ggaacgaaaa ctcacgttaa gggattttgg    840
tcatgagaca ataaccctga taatgcttc aataatattg aaaaggaag agtatgagta    900
ttcaacattt ccgtgtcgcc cttattccct ttttttgcggc attttgcctt cctgttttg    960
ctcacccaga aacgctggtg aaagtaaaag atgctgaaga tcagttgggt gcacgagtgg   1020
gttacatcga actggatctc aacagcggta agatccttga gagttttcgc cccgaagaac   1080
gttttccaat gatgagcact tttaaagttc tgctatgtgg cgcggtatta tcccgtattg   1140
acgccgggca agagcaactc ggtcgccgca tacactattc tcagaatgac ttggttgagt   1200
actcaccagt cacagaaaag catcttacgg atggcatgac agtaagagaa ttatgcagtg   1260
ctgccataac catgagtgat aacactgcgg ccaacttact tctgacaacg atcggaggac   1320
cgaaggagct aaccgctttt ttgcacaaca tgggggatca tgtaactcgc cttgatcgtt   1380
gggaaccgga gctgaatgaa gccataccaa acgacgagcg tgacaccacg atgcctgtag   1440
caatggcaac aacgttgcgc aaactattaa ctggcgaact acttactcta gcttcccggc   1500
aacaattaat agactggatg gaggcggata aagttgcagg accacttctg cgctcggccc   1560
ttccggctgg ctggtttatt gctgataaat ctggagccgg tgagcgtggg tctcgcggta   1620
tcattgcagc actggggcca gatggtaagc cctcccgtat cgtagttatc tacacgacgg   1680
ggagtcaggc aactatggat gaacgaaata gacagatcgc tgagataggt gcctcactga   1740
ttaagcattg gtaactgtca gaccaagttt actcatatat actttagatt gatttaaaac   1800
ttcattttta atttaaaagg atctaggtga agatcctttt tgataatctc atgagcggat   1860
acatatttga atgtatttag aaaaataaac aaataggggt tccgcgcaca tttccccgaa   1920
aagtgccacc tgatgcggtg tgaaataccg cacagatgcg taaggagaaa ataccgcatc   1980
aggaaattgt aagcgttaat aattcagaag aactcgtcaa gaaggcgata gaaggcgatg   2040
cgctgcgaat cgggagcggc gataccgtaa agcacgagga agcggtcagc ccattcgccg   2100
ccaagctctt cagcaatatc acgggtagcc aacgctatgt cctgatagcg gtccgccaca   2160
cccagccggc cacagtcgat gaatccagaa aagcggccat tttccaccat gatattcggc   2220
aagcaggcat cgccatgggt cacgacgaga tcctcgccgt cgggcatgct cgccttgagc   2280
ctggcgaaca gttcggctgg cgcgagcccc tgatgctctt cgtccagatc atcctgatcg   2340
acaagaccgg cttccatccg agtacgtgct cgctcgatgc gatgtttcgc ttggtggtcg   2400
aatgggcagg tagccggatc aagcgtatgc agccgccgca ttgcatcagc catgatggat   2460
actttctcgg caggagcaag gtgagatgac aggagatcct gccccggcac ttcgcccaat   2520
agcagccagt cccttcccgc ttcagtgaca acgtcgagca cagctgcgca aggaacgccc   2580
```

```
gtcgtggcca gccacgatag ccgcgctgcc tcgtcttgca gttcattcag ggcaccggac    2640
aggtcggtct tgacaaaaag aaccgggcgc ccctgcgctg acagccgaaa cacggcggca    2700
tcagagcagc cgattgtctg ttgtgcccag tcatagccga atagcctctc cacccaagcg    2760
gccggagaac ctgcgtgcaa tccatcttgt tcaatcatgc gaaacgatcc tcatcctgtc    2820
tcttgatcag agcttgatcc cctgcgccat cagatccttg gcggcaagaa agccatccag    2880
tttactttgc agggcttccc aaccttacca gagggcgccc cagctggcaa ttccggttcg    2940
cttgctgtcc ataaaaccgc ccagtctagc tatcgccatg taagcccact gcaagctacc    3000
tgctttctct ttgcgcttgc gttttccctt gtccagatag cccagtagct gacattcatc    3060
cggggtcagc accgtttctg cggactggct ttctacgtga aaaggatcta ggtgaagatc    3120 cttttttgata atctcatgcc tgacatttat attccccaga acatcaggtt aatggcgttt    3180
ttgatgtcat tttcgcggtg gctgagatca gccacttctt ccccgataac ggagaccggc    3240
acactggcca tatcggtggt catcatgcgc cagcttttcat ccccgatatg caccaccggg    3300
taaagttcac gggagacttt atctgacagc agacgtgcac tggccagggg gatcaccatc    3360
cgtcgccccg gcgtgtcaat aatatcactc tgtacatcca caaacagacg ataacggctc    3420
tctcttttat aggtgtaaac cttaaactgc cgtacgtata ggctgcgcaa ctgttgggaa    3480
gggcgatcgg tgcgggcctc ttcgctatta cgccagctgg cgaaaggggg atgtgctgca    3540
aggcgattaa gttgggtaac gccagggttt tcccagtcac gacgttgtaa aacgacggcc    3600
agtgaattgt aatacgactc actatagggc gaattgaatt tagcggccgc gaattcgccc    3660
ttgcgtcgac cgtctgaaac gggggcgagt aaccgttgta cagtccaaat gccgtctgaa    3720
gccttcagac ggcatcgtgc ctatcgggag aataaattgc agcctttagt cagcgtattg    3780
atttgcgcct acaacgtaga aaatatttc gcccaatcat tagccgccgt cgtgaatcaa    3840
acttggcgca acttggatat tttgattgtc gatgacggct cgacggacgg tacgcttgcc    3900
attgcccagc gtttccaaga acaggacggc cgcatccgca tcctcgcgca gccgcgcaat    3960
tccggtctga ttccctcttt aaacatcggg ctggatgaat tggcaaagtc ggggggggggg    4020 gggaatata ttgcgcgatc gctagctcga gcacgtgttg acaattaatc atcggcatag    4080
tatatcggca tagtataata cgacaaggtg aggaactaaa ccatggccaa gttgaccagt    4140
gccgttccgg tgctcaccgc gcgcgacgtc gccggagcgg tcgagttctg gaccgaccgg    4200
ctcgggttct cccgggactt cgtggaggac gacttcgccg gtgtggtccg ggacgacgtg    4260
accctgttca tcagcgcggt ccaggaccag gtggtgccgg acaacaccct ggcctgggtg    4320
tgggtgcgcg gcctggacga gctgtacgcc gagtggtcgg aggtcgtgtc cacgaacttc    4380
cgggacgcct ccgggccggc catgaccgag atcggcgagc agccgtgggg gcgggagttc    4440
gccctgcgcg acccggccgg caactgcgtg cacttcgtgg ccgaggagca ggactgagaa    4500 ttccccgggga tcctctagag tcgacctgca ggcatgcaag cttggcactg gccgtcgttt    4560
tacaacgtcg tgactgggaa aaccctggcg ttacccaact taatcgcctt gcagcacatc    4620 ccccttttcgc cagcgcgcac cgatgcagac gatattgccg ccccgactg gattgagaaa    4680 atcgtgggtg agatggaaaa agaccgcagc atcatcgcga tgggtgcgtg gctgaaagtt    4740
ttgtcggaag aaaaggacgg caaccggctg gcgcggcacc acgaacacgg caaaaattgg    4800
aaaaaaccga cccgcacgga agacattgcc gacttttttcc ctttcggcaa ccccatacac    4860
aacaacacga tgattatgag gcgcagcgtc attgacggcg gtttgcgtta caacaccgag    4920
cgggattggg cggaagatta ccaattttgg tacgatgtca gcaaattggg caggctggct    4980
```

```
tattatcccg aagccttggt caaataccgc cttcacgcca atcaggtttc atccaaatac    5040
agcatccgcc aacacgaaat cgcgcaaggc atccaaaaaa ccgccagaaa cgattttttg    5100
cagtctatgg gttttaaaac ccggttcgac agccttgaat accgccaaat aaaagcagta    5160
gcgtatgaat tgctggagaa acatttgccg gaagaagatt ttgaacgcgc ccgccggttt    5220
ttgtaccaat gcttcaaacg gacggacacg ctgcccgccg gcgcgtggct ggattttgcg    5280
gcagacggca ggatgcggcg gctgtttacc ttgaggcaat acttcggcat tttgcaccga    5340
ttgctgaaaa accgttgaaa aacgccgctt tatccaacag acaaaaaaca ggataaatta    5400
tgcaaaacca cgttatcagc ttagcttccg ccgcagaacg cagggcgccc gtttcagacg    5460
gtcgaaaggg cgaattcgtt taaacctgca ggactagtcc ctttagtgag ggttaattct    5520
gagcttggcg taatcatggt catagctgtt tcctgtgtga aattgttatc cgctcacaat    5580
tccacacaac atacgagccg gaagcataaa gtgtaaagcc tggggtgcct aatgagtgag    5640
ctaactcaca ttaattgcgt tgcgctcact gcccgctttc cagtcgggaa acctgtcgtg    5700
ccagctgcat taatgaatcg gccaacgcgc ggggagaggc ggtttgcgta ttgggcgct    5759

<210> SEQ ID NO 10
<211> LENGTH: 10
<212> TYPE: DNA
<213> ORGANISM: Artificial Sequence
<220> FEATURE:
<223> OTHER INFORMATION: putative uptake sequence

<400> SEQUENCE: 10
accgtctgaa                                                              10
```

MENINGOCOCCAL MULTIVALENT NATIVE OUTER MEMBRANE VESICLE VACCINE, METHODS OF MAKING AND USE THEREOF

CROSS-REFERENCE TO RELATED APPLICATIONS

This application is a 371 National Phase filing of International Patent Application Serial No. PCT/US2009/045818 filed Jun. 1, 2009, which claims priority to U.S. Patent Application Ser. No. 61/057,462 filed May 30, 2008. The above applications are incorporated herein by reference in their entirety.

FEDERALLY SPONSORED RESEARCH OR DEVELOPMENT

The U.S. Government has rights in this invention.

BACKGROUND OF THE INVENTION

*Neisseria meningitidis* is a major cause of meningitis and septicemia world-wide. Meningococcal meningitis is an inflammation of the meninges, the membrane lining the brain and the spinal cord. In both meningococcal septicemia and meningococcal meningitis, damage is caused by an uncontrolled localized or systemic host inflammatory response. Group B meningococcal disease currently accounts for at least one half of all meningococcal disease in many countries including North and South America, and Europe. The emergence of a new virulent clone of group B *Neisseria meningitidis*, known as ET5, in Norway in the late 70's has since been responsible for prolonged epidemics in Norway, Cuba, Brazil, and Chile. These epidemics have created serious public health problems and led to intensive efforts to develop an effective group B vaccine in several of the affected countries. The absence of a U.S.-licensed group B vaccine along with the poor performance of the A and C capsular polysaccharide vaccines in children under 18 months have prevented serious consideration of routine childhood vaccination against meningococcal disease.

*Neisseria meningitidis* is divided into 13 serogroups, of which 9 cause invasive disease (A, B, C(C1, C1-), X, Y, W-135, Z, and L). Five the serotypes are targeted for development of vaccines due to their ability to cause epidemics, including serotypes A, B, C, Y and W135 which are the target of much vaccine research.

Vaccines against serogroups A, C, Y and W135 of *Neisseria meningitidis* that cause nearly all invasive meningococcal disease are available and are routinely used with excellent results. A suitable vaccine against group B strains of *Neisseria meningitidis* has been more difficult to develop for a variety of reasons. For instance, the capsular polysaccharide which defines the serogroup is ineffective and potentially unsafe for use in a vaccine because it has the same structure as polysialic acid found on certain human cells, specifically blood cells.

Further adding to the lack of a suitable vaccine is the fact that subcapsular antigens that are surface exposed, such as outer membrane proteins and the lipooligosaccharide (endotoxin), are antigenically variable and/or inconsistently expressed among group B strains. No single antigen has been identified that alone has all the characteristics that are essential for an effective vaccine.

BRIEF SUMMARY OF THE INVENTION

In one aspect, the present technology provides a vaccine comprising native outer membrane vesicles (NOMVs) obtained from at least two meningococcal strains that have been genetically modified to provide broad based protection. The native outer membrane vesicles include three different sets of antigens based on PorA, LOS, and conserved outer membrane proteins; and the genetically modified strains have been modified to provide enhanced safety based on inactivation of lpxL1, synX, and lgtA genes. The two meningococcal strains can both express LOS having a different LOS core structure and has an alpha chains consisting of glucose and galactose. Each strain may express at least two different PorA subtype proteins or subtype epitopes which are chosen based on the most prevalent of PorA subtypes among group B case isolates. Further, the vaccine may further include a different conserved surface protein with demonstrated capacity to induce bactericidal antibodies is over-expressed in each strain and are taken from the group consisting of FHBP (GNA1870) variants 1, FHBP variants 2, and FHBP variants 3; NadA; App; NspA; TbpA and TbpB.

In a further aspect, the present technology provides a combination of NOMVs from three genetically modified, antigenically diverse *Neisseria meningitidis* strains. At least one of the stains is selected from (1) H44/76 HOPS-DL which has the following genetic modifications or characteristics:inactivation of the genes synX, lpxL1, and lgtA; insertion of a second porA gene (subtype P1.7-1,1) in the place of opaD; increased expression of NadA; and stabilized high expression of Opc and PorA; (2) 8570 HOPS-$G_4L$ which has the following genetic modifications or characteristics: inactivation of the genes synX, lpxL1, and lgtA; insertion of a second porA gene in place of opaD; increased expression of factor H binding protein variant 1; and stabilized high expression of PorA and Opc; and/or (3) B16B6 HPS-$G_2A$ which has the following genetic modifications or characteristics: inactivation of the genes synX, lpxL 1, and lgtA; insertion of a second porA gene in place of opaD; increased expression of factor H binding protein variant 2; and stabilized high expression of PorA and Opc. The NOMV are prepared without exposure to detergent or denaturing solvents from packed cells or from spent culture medium. The vaccine may be combined with one or more adjuvants and may be administered intramuscularly and/or intranasally.

In another aspect, the present technology provides a vaccine composition against meningococcal disease, more preferably group B meiningococcal disease, including native outer membrane vesicles (NOMVs) from one or more genetically modified strains of *Neisseria meningitidis*. The one or more genetically modified strains has been modified by: inactivation of the synX gene, inactivation of the lpxL1 gene, inactivation of the lgtA gene in each strain resulting in expression of a shortened or truncated lipooligosaccharides (LOS) that lacks lacto-N-neotetraose tetrasaccharide, and/or insertion of at least one second antigenically different porA gene in place of the opa gene. In another aspect, the genetically modified strain further comprises increased or stable expression of at least one minor conserved outer membrane protein, and/or stabilized expression of at least one outer membrane protein. The at least one second antigenically different porA gene may express at least one PorA subtype protein or subtype epitope selected from the most prevalent of PorA subtypes of meningitidis group B isolates.

In yet another aspect, the present technology provides a genetically modified vaccine strain of *Neisseria meningitidis* subtype B strain. The genetically modified vaccine strain may include H44/76 HOPS-D strain (B1), 8570 HOS-G1 strain (B2), and/or B16B6 HPS-$G_2A$ strain (B3).

In yet another aspect, the present technology provides a genetically modified vaccine strain of *Neisseria meningitidis* subtype B derived from: H44/76 strain comprising the genetic modifications of i) inactivation of a synX gene, ii) inactivation of the lpxL1 gene, iii) inactivation of the lgtA gene, iv) insertion of a second porA gene in the place of a opaD gene, v) increased expression of NadA compared with the native strain, and yl) stabilized increased expression of Opc and PorA proteins. In some aspects, the genetically modified strain was derived from the ET-5 wild type strain H44/76 (B:15: P1.7,16: L,3,7:P5.5,C).

In another aspect, the present technology provides a genetically modified vaccine strain of *Neisseria meningitidis* subtype B strain: derived from 8570 comprising the genetic modifications of: i) inactivation of a synX gene, ii) inactivation of the lpxL1 gene, iii) inactivation of the lgtA gene, iv) insertion of a second porA gene in place of opaD; v) increased expression of factor H binding protein variant 1; and yl) stabilized increased expression of PorA and Opc proteins. In some aspects, the genetically modified strain was derived from the ET-5 wild type strain 85 70(B:4: P1.19,15: L3,7v: P5.5,11,C).

In yet another aspect, the present technology provides a genetically modified vaccine strain of *Neisseria meningitidis* subtype B derived from B16B6 comprising the genetic modifications of: i) inactivation of a synX gene, ii) inactivation of the lpxL1 gene, iii) inactivation of the lgtA gene, iv) insertion of a second porA gene (subtype P1.22-1,4) in place of opaD; v) increased expression of factor H binding protein variant 2; and yl) stabilized increased expression of PorA and Opc proteins. In some aspects, the genetically modified strain is derived from the ET-37 wild type strain B16B6 (B:2a:P 1.5,2: L2:P5.1,2,5).

In some aspects, the present technology provides a genetically modified strain grown in iron deficient medium.

In other aspects, the present technology provides a genetically modified strain wherein inactivation of synX gene, lpxL1 gene, or lgtA gene is by an insertion of a drug resistance gene within the sequence of the inactivated gene.

Yet another aspect provides a vaccine including NOMVs derived from the genetically modified strains of the present technology. The NOMV are prepared from packed cells or spent culture medium without exposure to a detergent or denaturing solvent. The vaccine may further comprise one or more adjuvants. In further aspects, the genetically altered strain is altered to express iron uptake proteins.

In a further aspect, the present technology provides a vaccine against meningococcal disease comprising a variety of native outer membrane vesicles (NOMVs), wherein at least some of the NOMVs are essentially free of expression or sialylation of lipooligosaccharide (LOS), contain LOS that includes a lipid A with a penta-acyle structure and contain increased expression levels of at least one minor conserved outer membrane protein, wherein the minor conserved outer membrane protein is selected from proteins that induce bactericidal antibodies. The minor conserved outer membrane protein can be selected from the group consisting of NadA, factor H binding protein (FHBP) variant 1, and FHBP variant 2. In other aspects, at least some of the NOMV comprise shortened or truncated LOS that are essentially free of lacto-N-neotetraose (LNnT) tetrasaccharide and/or at least some of the NOMV comprise two or more different PorA proteins.

In another aspect, the present technology provides a method of eliciting an immune response to meningococcal disease in an animal or human comprising administering the composition containing NOMVs from at least one genetically altered strain of *N. Meniniitdis* to the animal or human for immunization against meningococcal disease. The vaccine is used for immunization against group B meningococcal disease.

In a further aspect, the present technology provides a method of preparing a genetically modified strain of *N. meningitidis* for use in a vaccine against meningococcal disease comprising the steps of: a) selecting a strain of meningococcal type B able to be genetically modified; b) genetically modifying the strain by inactivating the synX gene, c) genetically modifying the strain by inactivating the lpxL1 gene, d) genetically modifying the strain by inactivating the lgtA gene, and e) genetically modifying the strain by increasing expression of one or more minor conserved outer membrane proteins. In further aspects, the method further comprises genetically modifying the strain by inserting at least one second antigenically different porA gene into the open reading frame of the opa gene. In other aspects, the method further comprises the step of genetically modifying the strain to stably express or over express at least one outer membrane protein by replacing the poly-C sequence within the promoter or open reading frame of the at least one outer membrane protein with a sequence containing G and C nucleotides.

In yet another aspect, the present technology provides a method of preparing a vaccine against meningococcal disease comprising the steps of: a) culturing a genetically modified strain of *N. meningitidis* comprising one or more modification selected from the group consisting of inactivation of the synX gene, inactivation of the lpxL1 gene, inactivation of the IgtA gene, insertion of at least one second antigenically different porA gene in place of the opa gene, increased or stable expression of at least one minor conserved outer membrane protein, and/or stabilized expression of at least one outer membrane protein; b) expanding the culture by fermentation using the cultured strain of a) to inoculate medium in a fermentor; c) inactivating the fermented culture; d) harvesting *N. meningitidis* cultured cells by continuous flow centrifugation and collecting cell paste; e) isolating NOMVs from the cell paste; and f) resuspending NOMVs in buffer or carrier suitable for vaccine administration.

BRIEF DESCRIPTION OF SEVERAL VIEWS OF THE DRAWINGS

FIG. 4 is a flow chart depicting the purification of NOMVs from the genetically modified strains of *Neisseria* for vaccine production.

FIG. 8 is a picture of an antibody stained western blot showing the identity and composition of the proteins found in the 8570 HOPS-G NOMV vaccine.

FIG. 17 is a graph depicting the results of the bactericidal depletion assay for LOS and FHBP antigens for the 8570 HOPS-G1 PorA knockout strain.

FIG. 18 is a representation of phenotype of the three genetically modified strains of *Neisseria* (A=B1, B=B2, and C=B3) of the present technology.

FIG. 20a is depiction of the stabilization of the truncated LOS immunotype of NOMV vaccine strain by knockout of the lgtA gene of the three genetically modified strains. FIG. 20b is an picture of an immunoblot of the expression of LOS alpha chain by the genetically altered strain B2 and the parental strain (B16B6) with monoclonal antibodies against L3, 7,9 (left) and L8 (right).

FIG. 21 is a picture representation showing the expression of fHbp variant 2 in the genetically modified strain B3. The top panel shows selection of the strain containing the gentamicin resistance recombinant containing the overexpressed fHbp by immunoblotting and the bottom panel is a Western Blot using JAR4 monoclonal antibody to fHbp showing increased expression of fHBp.

DETAILED DESCRIPTION OF THE INVENTION

Figure 1:
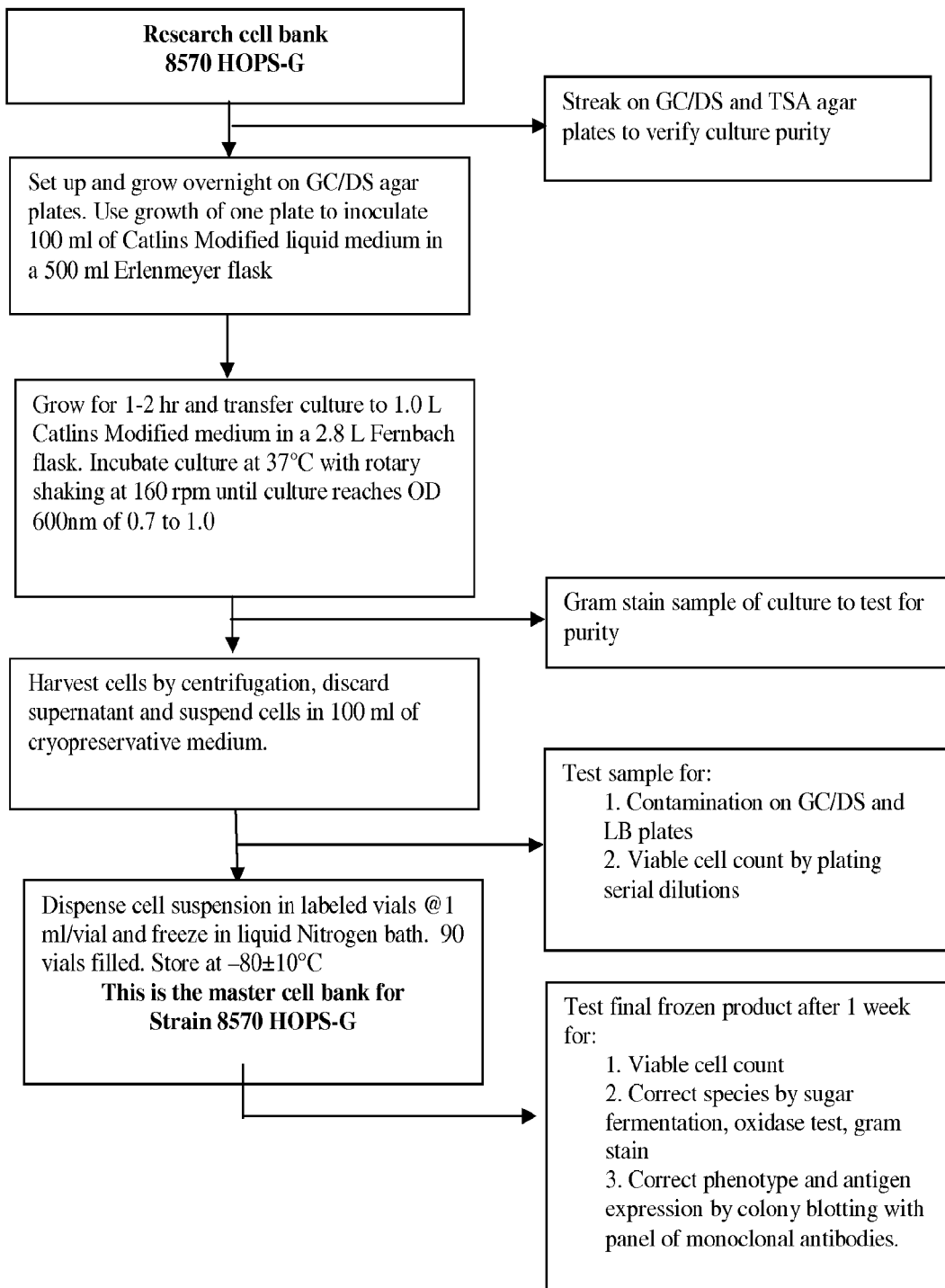
FIG. 1 is a flow chart depicting the preparation of a master cell bank of cells for the genetically modified strains of *Neisseria* for vaccine production.
Figure 2:
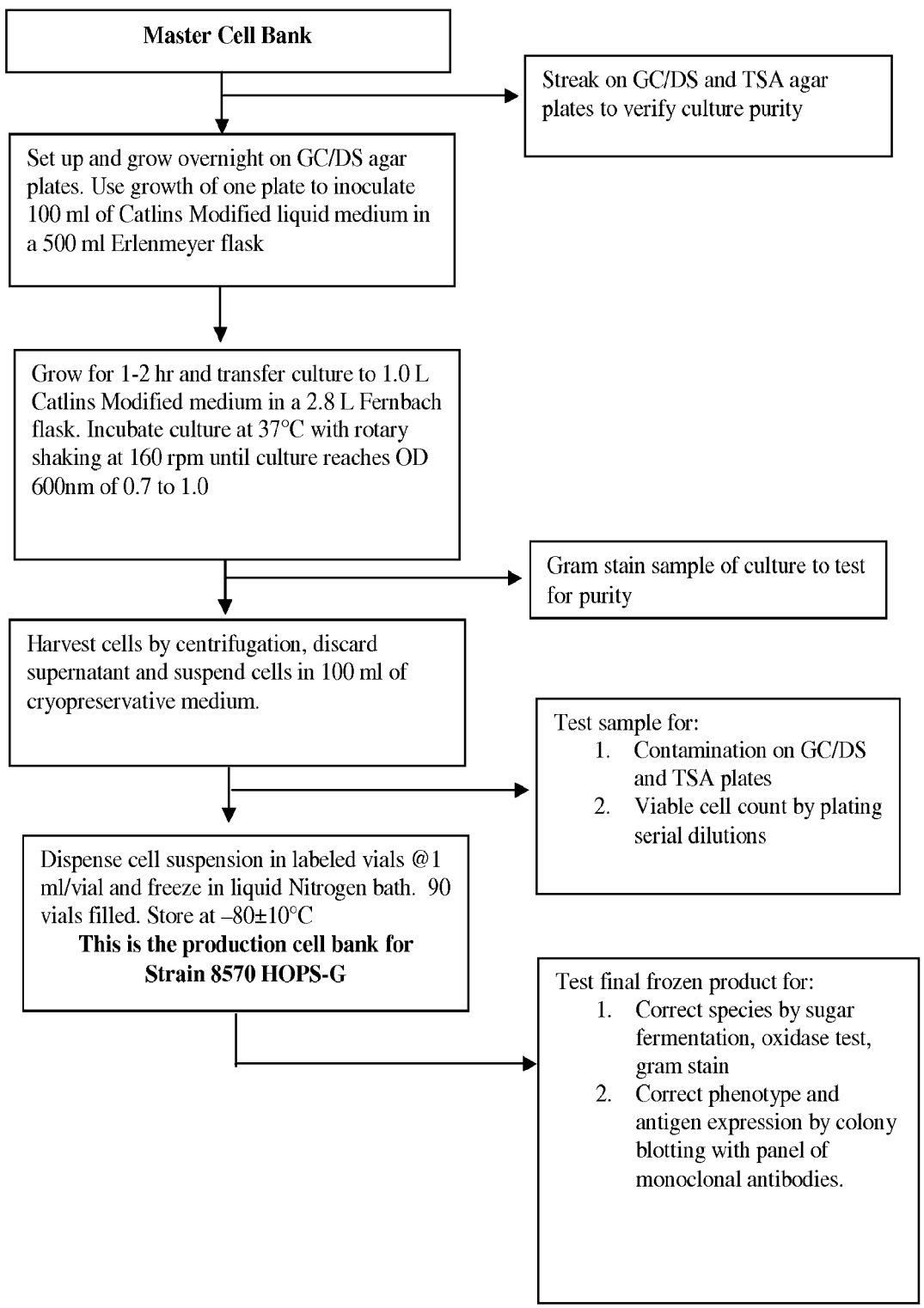
FIG. 2 is a flow chart depicting the production of the cell bank preparation used for making the genetically modified strains of *Neisseria* for vaccine production.
Figure 3:
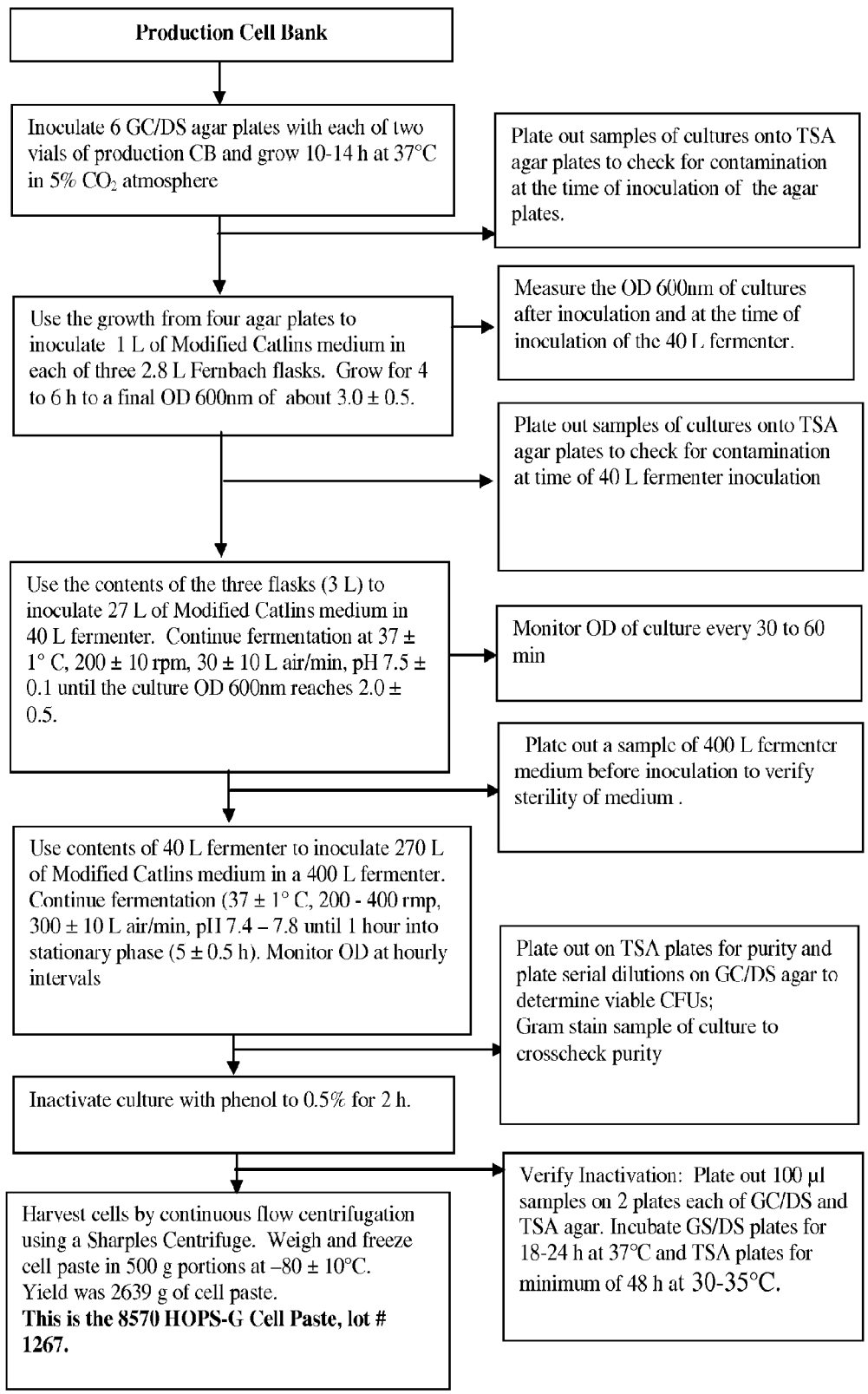
FIG. 3 is a flow chart depicting the fermentation of the *Neisseria* used for making the genetically modified strains of *Neisseria* for vaccine production.
Figure 5:
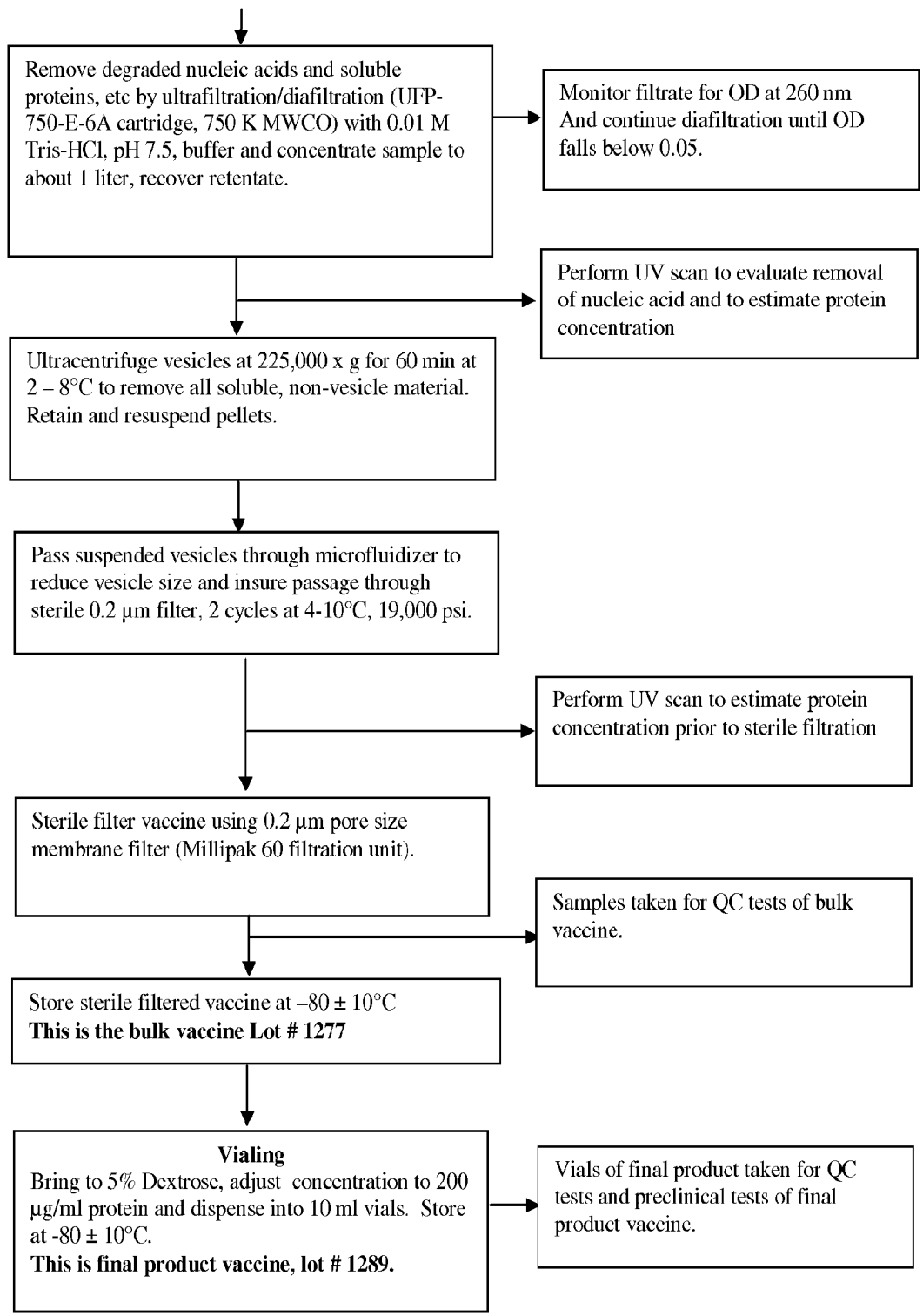
FIG. 5 is a continuation of the flow chart from FIG. 4.

The present technology provides a broadly protective vaccine composition for use in immunization against meningococcal disease, more preferably *Neisseria meningitidis* subgroup type B. One embodiment of the present technology provides a vaccine composition including native outer membrane vesicles (NOMVs) from at least one, preferably at least two, more preferably at least three genetically modified strains of *Neisseria meningitidis*. Native outer membrane vesicles, also known as blebs, are vesicles formed or derived from fragments of the outer membrane of gram negative bacterium naturally given off during growth and may be obtained from culture medium or from the cells by mild methods that do not use detergents or denaturing solvents. These NOMV typically comprise outer membrane proteins (OMPs), lipids, phospholipids, periplasmic material and lipopolysaccharide (LPS) including lipooligosaccharides. Gram negative bacteria, especially pathogens like *N. meningitidis*, often shed NOMVs during virulent infections in a process known as blebbing. In the present technology, NOMV are vesicles produced from the outer membrane of bacteria without the used of chemical denaturation processes and are produced from the genetically modified strains which are antigenically diverse and have each been genetically modified to improve safety, antigenic stability, and the breadth of the protective immune response.

One embodiment of the present invention provides a vaccine composition comprising native outer membrane vesicles (NOMVs) derived from at least two or more genetically modified strains of *N. meningitidis*, preferably at least three different genetically modified strains.

Some embodiments of the present technology provide antigenically diverse strains of *N. meningitidis*, preferably subtype B which include at least three genetic modifications within the genome of the bacteria, more preferably at least five genetic modifications, more suitable at least six genetic modifications. The genetic modifications can include one or more of the following: 1) inactivation of the synX gene, which is essential for sialic acid biosynthesis and results in no capsule expression or sialylation of lipooligosaccharide (LOS); 2) inactivation of the lpxL1 gene which results in a significantly less toxic LOS having lipid A with a penta-acyl structure; 3) insertion of a second, antigenically different porA gene in place of one of the opa genes (OpaC or OpaD); 4) increased expression of at least one minor conserved outer membrane protein, the minor conserved outer membrane protein demonstrating the ability to induce bactericidal antibodies (for example, but not limited to, NadA, factor H binding protein (FHBP) variant 1, and FHBP variant 2); 5) inactivation of the lgtA gene in each strain which results in the expression of a shortened or truncated LOS that lacks the lacto-N-neotetraose (LNnT) tetrasaccharide; and/or 6) stabilized expression of certain outer membrane proteins, such as Opc and PorA that are susceptible to phase variation in wild type strains.

The present technology provides genetically modified strains that provide both increased safety of use and increase the breadth of the protective antibody response to meningococcal disease. In one embodiment, the genetically modified strains provide increased safety by incorporating at least one of the following mutations into the bacterial genome: deletion of the synX gene which blocks sialic acid synthesis of capsid and results in the formation of capsule-negative phenotype NOMVs, deletion of the lpxL1 gene which reduces the endotoxin activity by resulting in a penta-acyl lipid A structure, and/or deletion of the lgtA gene which block lacto-N-neotetraose biosynthesis on the lipooligosaccharide (LOS) which stabilized the truncated LOS structure; more preferably the genetically modified strains provide two of these mutations, most preferably the genetically modified strains provide all three of these mutations. In another embodiment of the present technology, the genetically modified strains have an increased breadth of protective antibody response by targeting at least one of three sets of possible protective antigens contained within the NOMVs. The three possible antigens targeted include at least one of the following: PorA protein, at least one conserved minor protein, and/or the LOS core structure, and include any combination thereof. In more preferred embodiments, the genetically modified strain targets at least two of the possible protective antigens, most preferably targeting all three of the possible protective antigens.

In some embodiments of the present technology, the synX-mutation (inactivation of the synX gene) was inserted into the genetically modified strain by a method as described in U.S. Pat. No. 6,558,677, incorporated by reference herein in its entirety. In brief summary, a pUC19-based plasmid containing the synX gene in which 200 bp sequence was replaced by a kanamycin resistance gene is used to transform the genetically modified strain. Kan resistant transformants were selected and tested by PCR for the presence of the disrupted synX gene and for the capsule negative phenotype. This synX-mutant was constructed based on results and sequence information reported by Swartley and Stephens (Swartley and Stephens (1994) *J. Bacteriol.* 176: 1530-1534) who showed that insertion of a transposon into the synX gene led to a capsule negative phenotype. The same or an equivalent mutation can be introduced into any transformable *N. meningitidis* strain. A suitable plasmid for use in transforming meningococci was constructed using the following procedure. Three DNA sequences were pieced together using the splicing by overlap extension (SOE) polymerase chain reaction (PCR) technique (Horton et al. (1989) Gene 77: 61-65). The three DNA sequences included, in order beginning at the 5' end, synXB bases 67 to 681; the kanamycin resistance gene from pUC4K (Pharmacia LKB Biotech Co.) 671 to 1623; and synxB bases 886 to 1589. In addition, at the 5' end, a putative uptake sequence, ACCGTCTGAA (SEQ ID NO. 10), was added by including it at the end of the PCR primer used to amplify the synXB 67 to 691 base sequence. The complete construct was amplified by PCR, purified and blunt ligated into pUC19. pUC19 was used to transform *Escherichia coli* DH5a and selected on LB agar with 50 μg kanamycin. A kanamycin resistant colony was selected, the DNA extracted, purified, and cut with XbaI. Another copy of the presumptive uptake sequence was ligated into this multiple cloning region site and the resulting plasmid again used to transform *E. coli* DH5a and kanamycin resistant colonies screened by PCR for presence of the additional uptake sequence. Plasmid DNA was isolated from a selected colony and used as a template for PCR using primers that amplified only the insert part of the plasmid excluding the ampicillin resistance gene which should not be introduced into *N. meningitidis*. The amplified DNA was then purified and used to transform the genetically modified *N. meningitidis* strain. The synX(–) mutant of *N. meningitides* was selected by kanamycin resistance and confirmed by PCR amplification of the modified region.

In some embodiments of the present invention, the lpxL1 gene was inactivated in the genetically modified strains to produce a reduced endotoxic LOS expressed on the NOMVs in the vaccine compositions. The lipid A of *N. meningitidis* LOS is normally a hexa-acyl structure and is responsible for the endotoxic properties of the LOS. Two acyl-oxy-acyl linked secondary fatty acids present in the lipid A are important for endotoxic activity. The genetically modified strain includes the lpxL1 mutant as described by van der Ley and co-workers (van der Ley, P., Steeghs, L., Hamstra, H. J., van Hove, J., Zomer, B., and van Alphen, L. Modification of lipid A biosynthesis in *Neisseria meningitidis* lpxL mutants: influence on lipopolysaccharide structure, toxicity, and adjuvant activity. Infection and Immunity 69(10), 5981-5990, 2001.) Deletion of the lpxL1 gene resulted in expression of normal levels of penta-acyl LOS with greatly reduced endotoxicity as tested by both rabbit pyrogen test and by cytokine release assay using human monocytes from whole blood. Other methods for disrupting the lpxL1 gene are contemplated in further embodiments of the present technology for use in developing the genetically modified strains.

In some embodiments, the genetically modified strain contains an insertion of a second, antigenically different porA gene in place of one of the opa gene (OpaC or OpaD). The major outer-membrane protein, Porin A or PorA of *Neisseria meningitidis*, is the product of the porA gene. PorA has wide antigenic variation and is subject to phase variations to evade immune selective pressure; therefore it is not always cross-protective to other subtypes. To increase the reactivity of the vaccine compositions against different subtypes of PorA, at least one additional porA gene is inserted into the opaC or opaD gene of the genetically altered strain. The PorA serotype selected for insertion is selected based on the most prevalent forms of PorA found in cases of subtype B meningococcal disease. Suitable PorA serotypes include, but are not limited to: P1.7-1, (from strain M1080); P1.22,14 (from strain M4410); P1.22,1,4; or other suitable PorA serotypes as to be understood by one skilled in the art or described in the current literature, for example, as described by Sacchi et al., Diversity and prevalence of PorA types in *Neisseria meningitidis* serogroup B in the United States, 1992-1998, J Infect Dis. 2000 October; 182(4):1169-76. The second PorA genes may be under control of any suitable strong promoter that provided expression of the PorA protein, for example the PorA promoter from suitable strains, e.g., H44/76 strain. Suitable methods of cloning the porA gene into the genetically altered strain would be known to a person skilled in the art, and can include, but is not limited to homologous recombination. For example, the porA gene may be PCR amplified from bacterial chromosomal DNA, cloned into a cloning vector and recloned into an appropriately constructed plasmid, for example pUC19, using gene splicing by a modification of the overlap extension PCR technique. This construction plasmid can be introduced into the bacterial genome via homologous recombination such as to replace the opa gene. Transformants may be selected by colony blotting with monoclonal antibodies to the Porin. These methods are known to one skilled in the art.

In further embodiments of the present technology, the modified strains have stable and/or increased expression of at least one minor outer membrane protein. Suitable minor outer membrane proteins demonstrate the ability to induce bactericidal antibodies (for example, but not limited to, NadA, factor H binding protein (FHBP) variant 1, and FHBP variant 2). Not to be bound by any theory, stabilization and/or increased expression of highly conserved surface exposed minor outer membrane proteins identified through genomic analysis as having potential to induce protective antibodies may lead to an increase in the cross-protective immune response. Suitable conserved minor proteins include, but are not limited to, NadA, FHBP variant 1 and 2, and Opc. Methods of stabilizing and/or overexpression of the minor outer membrane protein (OMP) include use of expression plasmids and homologous recombination, or other suitable methods that are known to one skilled in the art. The minor OMPs can be under a strong promoter, for example, but not limited to the *N. meningitidis* PorA promoter or IPTG-inducible *E. Coli* ptac promoter.

As described in the examples below, construct plasmids were used to establish increased expression of fHbp 1 and fHbp 2 in the genetically modified strains, where the overexpressed protein appeared properly processed, lipidated, and translocated to the surface of the outer membrane. For example, expression of v.1 under the control of IPTG-inducible *E. coli* Ptac promoter in strain 8570 HOPS-G (B2) was about 4-fold higher than in the parental strain 8570 and expression of v.2 in strain B16B2 HPS-$G_2$A (B3) was 32-64 fold higher than in the parental strain B16B6 (See FIG. 20). Alternatively, an expression system that utilized the PorA promoter could be used to stabilize/overexpress the minor conserved proteins.

In further embodiments of the present technology, the genetically modified strains include inactivation of the lgtA gene which results in the expression of a shortened or truncated LOS that lacks the lacto-N-neotetraose (LNnT) tetrasaccharide.

An important characteristic of meningococcal LOS is phase-variation, which occurs due to high-frequency mutations in homopolymeric tracts of nucleotide residues in lgtA and other neisserial genes. These mutations switch on or off the expression of the LgtA transferase which mediates the assembly of the LOS α-chain (altering the configuration of substituents on heptose two). This phase-variable activation of the lgtA gene may lead to undesirable elongation of the LOS α-chain resulting in lacto N-neotetraose which has structural similarity to human blood cell antigens. The genetically modified strains of the present technology have the lgtA gene knocked out by disrupting the native gene with a antibiotic marker or other suitable marker (for use in screening for alternations in the gene), for example, but not limited to the zeomycin resistance gene. Methods of knocking out the lgtA gene are known to one skilled in the art including, but not limited to construct plasmids and homologous recombination or transformation. The mutated ΔlgtA gene was inactive in all modified strains during at least 22 observed passages and this was a stabilized truncated form of the LOS core structure. The deletion of the lgtA gene stabilizes the truncated α-core LOS structure, for example, providing the truncated core structures as depicted in FIG. 19, wherein three exemplary modified strains are shown, for example the B3 strain contains the L8 alpha chain with the L3 core structure. The genetically modified strains of the preset technology contain specific LOS core structures corresponding to immunotypes L3, L5 and L2 providing stabilized core structures in which an immune response can be mounted, and in the examples below demonstrate truncated L8-like LOS (L8-3, L8-5, and L8-2) which are able to kill wild type strains expressing full length LOS. ΔlgtA strains are able to elicit antibodies that recognize both the truncated and full-length forms of the LOS structure, without cross-reacting with the lacto-N-neotetraose oligosaccharides found on human blood cells.

In further embodiments of the present technology, the genetically modified strains of *N. meningitidis* have stabilized expression of outer membrane proteins that are normally susceptible to phase variation in wildtype strains, for example, but not limited to, Opc and PorA. The expression of these proteins can be stabilized by methods known in the art, and include the method of replacing the polymeric repeat sequence in either the promoters or within the reading frame of the gene being stabilized with a non-repeating sequence of optimal length form maximal expression. For example, part of the poly-C or poly-G sequence in the promoter of these genes can be replaced with a sequence of the same length containing both C and G nucleotides, for example, 12 bp poly-G sequence of the promoter of opcA (see Seq. ID. No. 1) was replaced with a new sequence of the same length containing both C and G nucleotides and a Not I site (See Seq. ID No. 2, Not I site underlined). In other suitable embodiments, the poly-G sequence in the PorA promoter (for example, see Seq. ID No. 3) can be replaced with a new sequence containing both C and G nucleotides.

Further embodiments of the present technology provide growth of the vaccine strains in liquid medium containing a low level of iron in order to induce protein expression of proteins involved in uptake of iron, for example transferring binding protein A and B. In some embodiments, the medium used did not contain specific addition of iron chelators such as desferol. One suitable medium is modified from that published by B W Catlin (Catlin B W. (1973) *J. Infec. Dis.* 128: 178-194) by replacing sever individual amino acids with 1% casamino acids (certified, Difco Laboratories). The medium contained per liter: 0.4 g $NH_4Cl$, 0.168 g KCl, 5.85 g NaCl, 1.065 g $Na_2HPO_4$, 0.17 g $KH_2PO_4$, 0.647 g sodium citrate, 6.25 g sodium lactate (60% syrup), 0.037 g $CaCl_2.2H_2O$, 0.0013 g $MnSO_4.H_2O$, 5 g glycerol, 0.02 g cysteine, 10 g casamino acids, 0.616 g $MgSO_4$, and distilled water to one liter. The same iron deficient medium was used for the starter flasks and the final culture flasks or fermenters.

The vaccine composition of the present technology which includes NOMVs from at least three different genetically modified strains of subgroup B can provide three potential levels of protection or three types of antigens that each potentially induce a protective antibody response. The three antigens are the PorA protein (six different PorA subtypes are present in the vaccine, two on each of the three vaccine strains); the lipooligosaccharides (three different LOS core structures are present in the vaccine, one from each strain); and the conserved minor proteins NadA, FHBP variants 1 and 2, and Opc, which have been over expressed in the vaccine strains. Although PorA has a relatively high level of antigenic variation with several hundred different sequence variations having been identified, certain PorA serosubtypes are much more frequently encountered than others and a modest number of different serosubtypes may potentially protect against more than half of group B disease. Having more than one antigen capable of inducing bactericidal antibodies in the vaccine is important because it has been shown that when the surface density of an antigen is low, antibodies to it may not be able to initiate a complement mediated lytic event. But if antibodies to two or more such antigens are present the antibodies can together initiate complement mediated lysis. Genetically modified strains of the present invention include, but are not limited to, the three strains depicted in FIG. 18, including B1 (44/76 HOPS-D), B2 (8570 HOPS-G1) and B3 (B16B6 HPS-G2) strains. These three strains have been deposited with the ATCC in accordance with the Budapest Treaty and were given ATCC deposit designations. The 8570HOPS-G strain is listed as ATCC deposit PTA-10224 (deposited on Jul. 16, 2009), B16B6 HPS-$G_2$L as ATCC deposit PTA-10584 (deposited on Jan. 15, 2010) and 44/76 HOPS-DL as ATCC deposit PTA-121594 (deposited on Sep. 11, 2014).

The present technology provides a vaccine that provides broad spectrum protection against meningococcal disease, specifically meningococcal disease caused by *Neisseria meningitidis* subgroup B. The vaccine composition of the present invention can be combined with the existing tetravalent A, C, Y, and W-135 vaccine to provide protection against a majority of pathogenic serogroups of *N. meningitidis*. Not to be bound by any particular theory, the vaccine of the present technology may also provide back up protection against the other pathogenic serogroups as well as the minor serogroups of meningococci since the subcapsular antigens on which it is based are shared across all serogroups of meningococci.

In preferred embodiments of the present technology, the genes of interest or DNA of interest is delivered and integrated into the bacterial chromosome by means of homologous and/or site specific recombination. Integrative vectors used to deliver such genes and/or operons can be conditionally replicative or suicide plasmids, bacteriophages, transposons, or linear DNA fragments obtained by restriction hydrolysis or PCR amplicification as known by one skilled in the art. In some embodiments, integration is targeted to chromosomal regions dispensable for growth in vitro. In other embodiments, the gene of interest or DNA of interest can be delivered to the bacterium by means of episomal vectors such as circular/linear replicative plasmids, cosmids, plasmids, lysogenic bacteriophages, or bacterial artificial chromosomes. Selection of recombination events can be selected by means of selectable genetic markers such as genes conferring resistance to antibiotics (e.g., kanamycin, zeomycin, erythromycin, chloramphenicol, gentamycin, etc.), genes conferring resistance to heavy metal and/or toxic compounds or genes complementing auxotrophic mutations. Alternatively, recombination can be screened by PCR amplification, sequencing, restriction digestion or other methods known to one skilled in the art.

A "vaccine" as referred herein is defined as a pharmaceutical or therapeutic composition used to inoculate an animal in order to immunize the animal against infection by an organism, preferably a pathogenic organism. Vaccines typically comprise one or more antigens derived from one or more organisms which on administration to an animal will stimulate active immunity and protect that animal against infection with these or related pathogenic organisms.

The purified NOMVs are prepared for administration to mammals, suitably humans, mice, rats or rabbits, by methods known in the art, which can include filtering to sterilize the solution, diluting the solution, adding an adjuvant and stabilizing the solution.

Vaccines of the present invention may be administered to a human or animal by a number of routes, including but not limited to, for example, parenterally (e.g. intramuscularly, transdermally), intranasally, orally, topically, or other routes know by one skilled in the art. The term parenteral as used hereinafter includes intravenous, subcutaneous, intradermal, intramuscular, intraarterial injection, or infusion techniques. The vaccine may be in the form of a single dose preparation or in multi-dose flasks which can be used for mass vaccination programs. Suitable methods of preparing and using vaccines can be found in *Remington's Pharmaceutical Sciences*, Mack Publishing Co., Easton, Pa., Osol (ed.) (1980) and *New Trends in Developments in Vaccines*, Voller et al. (eds.), University Park Press, Baltimore, Md. (1978), incorporated by reference.

A vaccine composition of the present technology is typically administered parenterally in dosage unit formulations containing standard, well-known nontoxic physiologically acceptable carriers, adjuvants, and/or vehicles.

The vaccine compositions of the present technology may further comprise one or more adjuvants. An "adjuvant" is a substance that serves to enhance, accelerate, or prolong the antigen-specific immune response of an antigen when used in combination with specific vaccine antigens but do not stimulate an immune response when used alone. Suitable adjuvants include inorganic or organic adjuvants. Suitable inorganic adjuvants include, but are not limited to, for example, an aluminium salt such as aluminum hydroxide gel (alum) or aluminium phosphate (preferably aluminium hydroxide), but may also be a salt of calcium (particularly calcium carbonate), iron or zinc, or may be an insoluble suspension of acylated tyrosine, or acylated sugars, cationically or anionically derivised polysaccharides or polyphosphazenes. Other suitable adjuvants are known to one skilled in the art. Suitable Th1 adjuvant systems may also be used, and include, but are not limited to, for example, Monophosphphorly lipid A, other non-toxic derivatives of LPS, and combination of monophosphoryl lipid A, such as 3-de-O-acrylated monophosphorly lipid A (#D-MPL) together with an aluminium salt.

Other suitable examples of adjuvants include, but are not limited to, MF59, MPLA, *Mycobacterium tuberculosis, Bordetella pertussis*, bacterial lipopolysaccharides, aminoalkyl glucosamine phosphate compounds (AGP), or derivatives or analogs thereof, which are available from Corixa (Hamilton, Mont.), and which are described in U.S. Pat. No. 6,113,918; e.g., 2-[(R)-3-Tetradecanoyloxytetradecanoylamino]ethyl, 2-Deoxy-4-O-phosphono-3-O—[(R)-3-tetradecanoyoxytetradecanoy 1]-2-[(R)-3-tetradecanoyoxytetradecanoylamino]-b-D-glucopyra noside, MPL™ (3-O-deacylated monophosphoryl lipid A) (available from Corixa) described in U.S. Pat. No. 4,912,094, synthetic polynucleotides such as oligonucleotides containing a CpG motif (U.S. Pat. No. 6,207,646), COG-ODN (CpG oligodeoxynucleotides), polypeptides, saponins such as Quil A or STIMULON™ QS-21 (Antigenics, Framingham, Mass.), described in U.S. Pat. No. 5,057,540, a pertussis toxin (PT), or an *E. coli* heat-labile toxin (LT), particularly LT-K63, LT-R72, CT-5109, PT-K9/G129; see, e.g., International Patent Publication Nos. WO 93/13302 and WO 92/19265, cholera toxin (either in a wild-type or mutant form). Alternatively, various oil formulations such as stearyl tyrosine (ST, see U.S. Pat. No. 4,258,029), the dipeptide known as MDP, saponin, cholera toxin B subunit (CTB), a heat labile enterotoxin (LT) from *E. coli* (a genetically toxoided mutant LT has been developed), and Emulsomes (Pharmos, LTD., Rehovot, Israel). Various cytokines and lymphokines are suitable for use as adjuvants. One such adjuvant is granulocyte-macrophage colony stimulating factor (GM-CSF), which has a nucleotide sequence as described in U.S. Pat. No. 5,078,996. The cytokine Interleukin-12 (IL-12) is another adjuvant which is described in U.S. Pat. No. 5,723,127. Other cytokines or lymphokines have been shown to have immune modulating activity, including, but not limited to, the interleukins 1-α, 1-β, 2, 4, 5, 6, 7, 8, 10, 13, 14, 15, 16, 17 and 18, the interferons-α, β and γ, granulocyte colony stimulating factor, and the tumor necrosis factors α and β, and are suitable for use as adjuvants.

The vaccine compositions can be lyophilized to produce a vaccine against *N. meningitidis* in a dried form for ease in transportation and storage. Further, the vaccine may be prepared in the form of a mixed vaccine which contains the NOMVs containing the proteins from the genetically altered strains described above and at least one other antigen as long as the added antigen does not interfere with the effectiveness of the vaccine and the side effects and adverse reactions are not increased additively or synergistically. The vaccine can be associated with chemical moieties which may improve the vaccine's solubility, absorption, biological half life, etc. The moieties may alternatively decrease the toxicity of the vaccine, eliminate or attenuate any undesirable side effect of the vaccine, etc. Moieties capable of mediating such effects are disclosed in *Remington's Pharmaceutical Sciences* (1980). Procedures for coupling such moieties to a molecule are well known in the art.

The vaccine may be stored in a sealed vial, ampule or the like. The present vaccine can generally be administered in the form of a spray for intranasal administration, or by nose drops, inhalants, swabs on tonsils, or a capsule, liquid, suspension or elixirs for oral administration. In the case where the vaccine is in a dried form, the vaccine is dissolved or suspended in sterilized distilled water before administration. Any inert carrier is preferably used, such as saline, phosphate buffered saline, or any such carrier in which the NOMV vaccine has suitable solubility.

Vaccine compositions of the present technology may include a carrier. If in a solution or a liquid aerosol suspension, suitable carriers can include, but are not limited to, salt solution, sucrose solution, or other pharmaceutically acceptable buffer solutions. Aerosol solutions may further comprise a surfactant.

Among the acceptable vehicles and solvents that may be used include water, Ringer's solution, and isotonic sodium chloride solution, including saline solutions buffered with phosphate, lactate, Tris and the like. In addition, sterile, fixed oils are conventionally employed as a solvent or suspending medium, including, but not limited to, for example, synthetic mono- or di-glycerides. In addition, fatty acids such as oleic acid find use in the preparation of injectables.

Injectable preparations, for example sterile injectable aqueous or oleaginous suspensions, are formulated according to the known art using suitable dispersing or wetting agents and suspending agents. The sterile injectable preparation are also a sterile injectable solution or suspension in a nontoxic parenterally acceptable diluent or solvent, for example, as a solution in 1,3-butanediol.

The presently described technology and its advantages will be better understood by reference to the following examples. These examples are provided to describe specific embodiments of the present technology. By providing these specific examples, the applicants do not limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1

Derivation of the Genetically Modified Vaccine Strain of *N. Meningitidis* and Production of NOMVs Containing the Outer Membrane Proteins of the Genetically Modified Vaccine Strain The genetically modified strain 8570 HOPS-G1 was modified by five genetic modifications from a parental strain 8570 which had been analyzed by multilocus enzyme electrophoresis by the laboratory from whom the strain was obtained and determined to belong to the ET-5 clonal complex (Caugant, et al.) The PorA variable regions were sequenced typed and the LOS immunotype was verified before the genetic modifications were made. Strain 8570 was and ET-5 clone 4:P1.19, 15:L7v, ProB3 (ST4) Tbp2 type II. A series of five sequential genetic modifications were made to the strain as described below:

1) A second, different porA gene was inserted at the opaD locus knocking out the opaD gene. pUC19-based plasmid pA 18.4 has no antibiotic resistance marker in the insert, was used to insert a second porA gene into the chromosome at the opaD locus, disabling opaD by replacing a 100 bp sequence in the middle of the gene with the insert. The insert contained the new porA gene taken from strain M4410 (B:15:P1.22,14) and placed behind a porA promoter taken from strain H44/76. The resulting porA type was P1.19,15: P1.22,14 containing the two porin A genes.

2) Starting with the strain resulting from 1, with a second PorA expressed, the expression of the outer membrane protein OpcA was stabilized by replacing a 12 bp poly-C sequence in the promoter of opcA with a new sequence of the same length containing both C and G nucleotides. Original promoter sequence (Seq. ID No. 1) (poly-G sequence italicized and bold) 5'..CATAGTTAAAACCTCTAAAATTTG-GATTGTAGTCGGATATGGTAACATAACGTAAATAAT-CGTTACGCTTACAATTATATTCTTAAGCTTTC *GGGGGG GGGGGG* ATTT..3' was replaced with a modified promoter sequence (Seq ID No. 2) containing both G and C nucleotides with a Not I site (underlined) 5'..CATAGT-TAAAACCTCTAAAATTTGGATTGTAGTCGGATATGG-TAACATAACGTAAATAATCGTTACGCTTACAATTATA-TTCTTAAGCTTTC*GC GCGGCCGC GC* ATTTT.3' The replacement sequence was chosen to contain a restriction site for NotI to enable verification of the presence of the replacement sequence. The plasmid used for the transformation was pOpc79 (Seq. ID No. 4). The plasmid insert does not contain an antibiotic marker. Selection of transformants was based on colony blotting with monoclonal antibody to OpcA. The strain to be transformed was chosen to be an OpcA negative phase variant, and strong OpcA positive clones were identified by colony blotting. True transformants were distinguished from OpcA positive phase variants by PCR and restriction enzyme (Not I) analysis.

3) Starting with the strain resulting from 2, the gene lpxL1, which is an acyl transferase responsible for linking one of two acyl-oxy-acyl linked fatty acids to the lipid A of the LOS, was disabled by replacing a 260 bp sequence in the middle of the lpxL1 gene with an insert containing the tetM antibiotic resistance gene. The tetM gene was obtained from a plasmid pJS 1934, which was derived from the transposon Tn916 (Swartley, et al. 1993. Mol. Microbiol. 10:299-310). The plasmid used to disable the lpxL1 gene was pMn5 (Seq. ID No. 5). The presence of the insert in the lpxL1 gene was verified by PCR which produced a 3.3 kbp amplicon using primers at the beginning and end of the lpxL1 gene.

Figure 19:
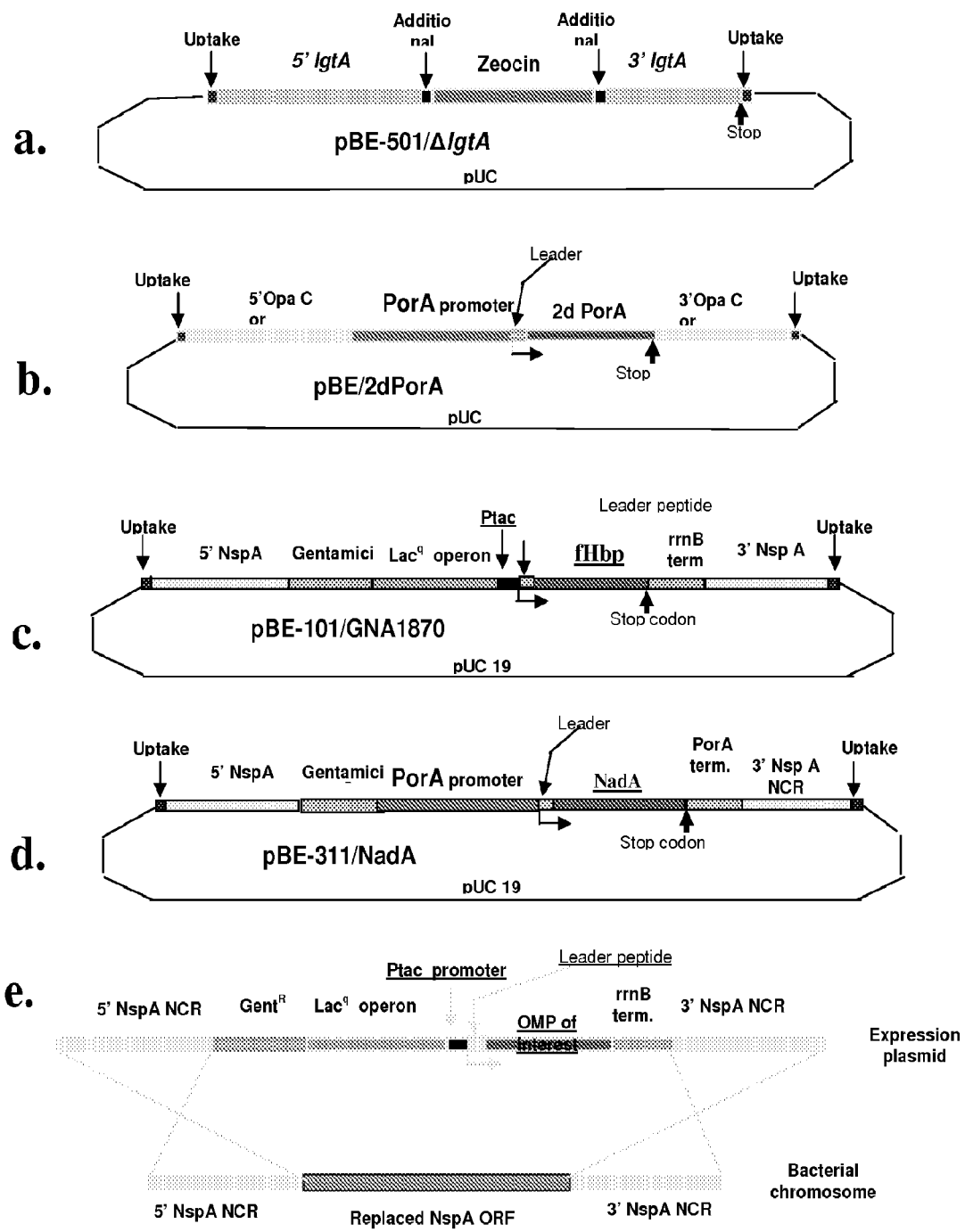
FIG. 19 is a representation of the plasmids used to construct the genetically modified strains of *Neisseria*: a) plasmid constructed to knockout lgtA, b) plasmid to express second PorA, c) plasmid to overexpress fHbp driven by orthologous (Ptac if *E. coli*) promoter, and d) plasmid to overexpress NadA driven by a homologous promoter (PorA promoter of *N. meningitidis*) and the e) representational scheme of transformation of *N. meningitis* with fHbp (variant 1 and 2) and NadA overexpression plasmid via homologous recombination replacing NspA gene.

4) Starting with the strain resulting from step 3, expression of the conserved outer membrane protein GNA 1870 (variant 1) (FHBP v.1) was increased by inserting a second copy of the GNA 1870 variant 1 gene in the nspA locus, knocking out expression of NspA. The newly inserted gene was part of an insert that contained a gentamicin antibiotic resistance gene, the *E. coli* lac operon with the IPTG-inducible Ptac promoter, the GNA1870 variant 1 gene and the rrnB terminator, the plasmid used is depicted in FIG. 19c and Seq. ID No. 6. The PUC19 based plasmid, pBE/GNA1870/101, was used in the transformation and homologous recombination to insert the GNA 1870 variant 1 gene into the modified strain. pBE/GNA1870/101 plasmid (7687 b.p.) was constructed with the features as described in Table 1 (sequence can be found in Seq. ID No. 6).

TABLE 1

| Feature | Coordinates (nt ##) | Source |
| --- | --- | --- |
| pUC19*) | 1-191 | New England Biolabs (NEB) |
| Sac I site (unique) | 192-197 | pUC19 cloning site |
| Uptake Sequence | 198-212 | PCR construct |
| 5' NspA non coding region (NCR) | 213-1248 | *N. mening.*, 44-76, PCR construct |

TABLE 1-continued

| Feature | Coordinates (nt ##) | Source |
|---|---|---|
| Bam H I site | 1249-1254 | Gent$^R$ gene cloning site |
| Gent$^R$ gene | 1255-2104 | PCR construct of Gent$^R$ gene |
| Sac II (unique) | 2105-2110 | PCR construct |
| Rmp promoter 5' fragment (rest) | 2111-2230 | Previous plasmid for NspA expression |
| Mfe I site (unique) | 2231-2236 | PCR construct |
| Lac$^q$ operon | 2237-3641 | pMAL-p2X (New England Biolabs) |
| Ptac promoter | 3642-3673 | pMAL-p2X, PCR construct |
| Lac operator | 3674-3702 | pMAL-p2X, PCR construct |
| RBS | 3750-3755 | pMAL-p2X, PCR construct |
| Nde I site (unique) | 3761-3766 | PCR construct |
| fHBP (variant 1) leader peptide | 3764-3823 | *N. mening.*, 44-76, PCR construct |
| fHBP (variant 1) ORF with stop codon | 3824-4588 | *N. mening.*, 44-76, PCR construct |
| SgrAI site (unique) | 4589-4596 | *N. mening.*, 44-76, PCR construct |
| 3'NspA and 3'NspA NCR | 4597-4638 | Previous plasmid for NspA expression |
| rrnB transcription terminators | 4639-4945 | pBAD/Thio-E (Invitrogen), PCR |
| 3' NspA NCR | 4946-5432 | *N. mening.*, PCR construct |
| Uptake Sequence | 5433-5447 | PCR construct |
| Hind III | 5448-5453 | pUC19 cloning site |
| pUC 19 | 5454-7687 end | NEB (Amp.$^R$) |

*)Start from nt. 1 of pUC 19. The plasmid was modified to remove Nde I site for further convenient cloning as follow: It was digested by Nde I - EcoR I and 213 b.p. fragment was removed. Sticky ends were filled in and ligated to restore the plasmid. As a result sited Nde I (183) and EcoRI (395) were destroyed. For cloning of constructs for the expression of target protein we used Sac I and Hind III cloning sites of pUC 19.

5) The strain resulting from step 4 was transformed with a pUC19-based plasmid containing the synX gene in which a 200 bp sequence was replaced by a kanamycin resistance gene. Kan resistant transformants were selected and tested by PCR for the presence of the disrupted synX gene and for the capsule negative phenotype. The results verified the knockout of the synX gene.

6) The strain resulting from step 4 was transformed with a plasmid pBE-501 containing zeomycin gene knocking out the lgtA gene (Seq. ID No. 9). Plasmid pBE-501 contained the features found in Table 2. Knock-out of the lgtA gene produced expression of a shortened or truncated LOS that lacks the lacto-N-neotetraose (LNnT) tetrasaccharide (see FIG. 20).

TABLE 2

| Feature | Coordinates (nt #) | Source |
|---|---|---|
| pCR 4-TOPO TA cloning Vector | 1-3667 | Invitrogen. Type: pUC ori |
| Uptake Sequence | 3668-3682 | PCR construct |
| LgtA 5' segment | 3683-4037 | *N. mening.*, 2996, PCR construct |
| pEM7/Zeo | 4038-4122 | Invitrogen. Cloning site and EM7 promoter Zeocin |
|  | 4123-4497 | Zeocin$^R$ gene provided ΔLgtA pEM7/Zeo |
|  | 4498-4633 | Fragment of pEM7/Zeo cloning site LgtA 3' |
| segment | 4634-5448 | *N. mening.*, 2996, PCR construct |
| Uptake Sequence | 5449-5463 | Uptake sequence |
| pCR 4-TOPO TA cloning Vector | 5464-5759 end | Invitrogen |

*) LgtA cDNA was digested by BssH II. Resulting 3' and 5' sticky ends were refilled and Zeocin gene was inserted in this blunt ended cDNA. In case of excising of disruptive Zeocin gene which may occur during of the reparation of bacterial DNA, relegated 5' and 3' of LgtA fragments will bearing unreparable sequence This genetically modified strain was tested to unsure retention of all five mutations and expression of all expected antigens.

Example 2

Production of Vaccine Amounts of the Genetically Modified Strain

The genetically modified strains were then used for production of master and production cell banks for use in vaccine manufacture as detailed in the flow-charts in FIGS. 1-5 to produce a composition of NOMVs. The NOMVs culture is tested for the expression of the outer membrane proteins and LOS.

Example 3

Characterization of Vaccines

The final product obtained from Example 2 was subjected to quality control testing and preclinical safety and immunogenicity testing in mice and rabbits.

The composition of the final product vaccine was:
Protein 2001 ag/ml
Lipooligosaccharide 36 tg/ml
Nucleic Acid 2.5 µg/ml
Sodium Chloride 0.9%
Tris-HCl Buffer 0.01 M pH 7.6

Figure 6:
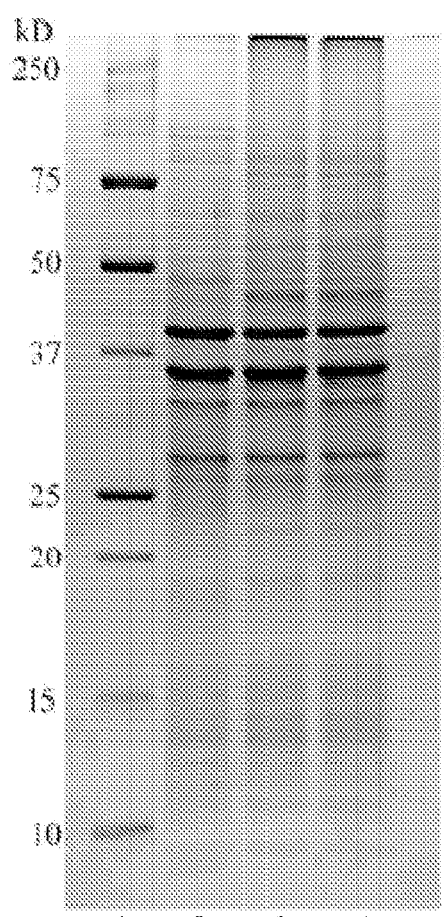
FIG. 6 is a picture of a COOMASSIE® BLUE stained gel showing the protein content of standard marker (lane 1), control 8570 HOPS-G NOMV preparation (lane 2), filtered bulk vaccine (lane 3) and final product vaccine (lane 4).
Figure 7:
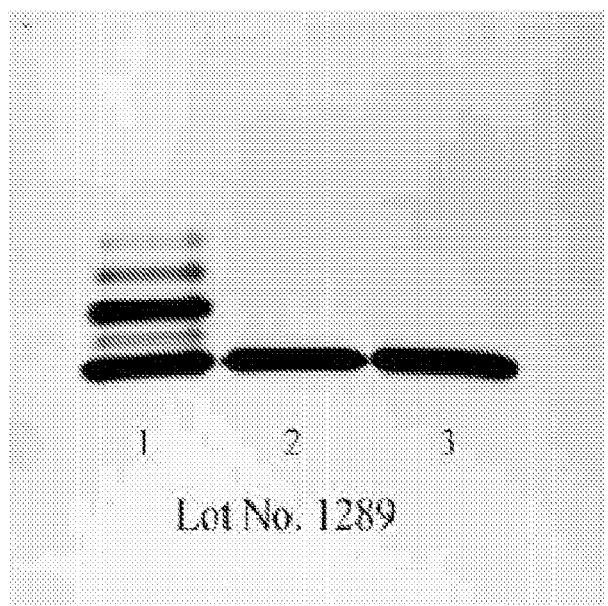
FIG. 7 is a silver stained gel showing lipooligosaccharide content of the vaccine. Lane 1 is the control ML5 LPS, lane 2 is the filtered bulk vaccine and lane 3 is the final vaccine product. Fifteen µl of a 1:2 dilution of 100 µg/ml of the vaccine were run on the gel (20 µl of 100 µl/ml of 1:2 dilution of control).
Figure 9:
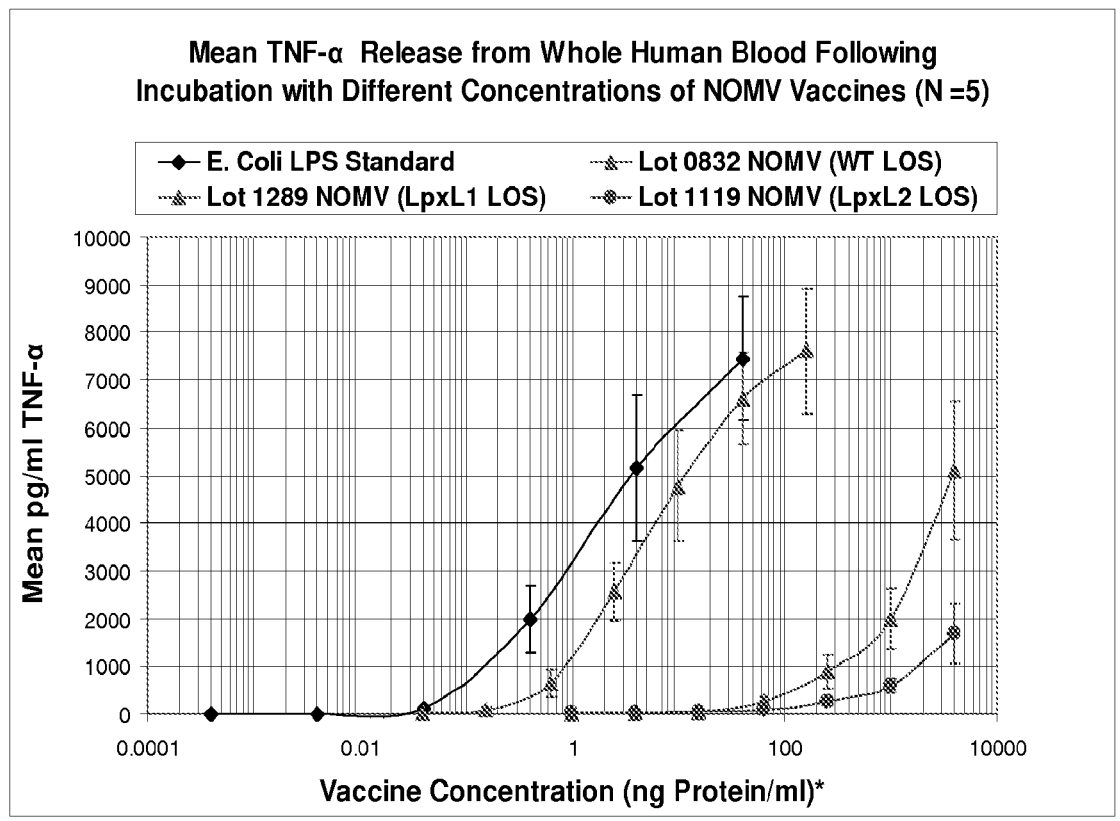
FIG. 9 is a graph depicting the TNF-α released from human blood after incubation with different concentrations of the vaccine.
Figure 10:
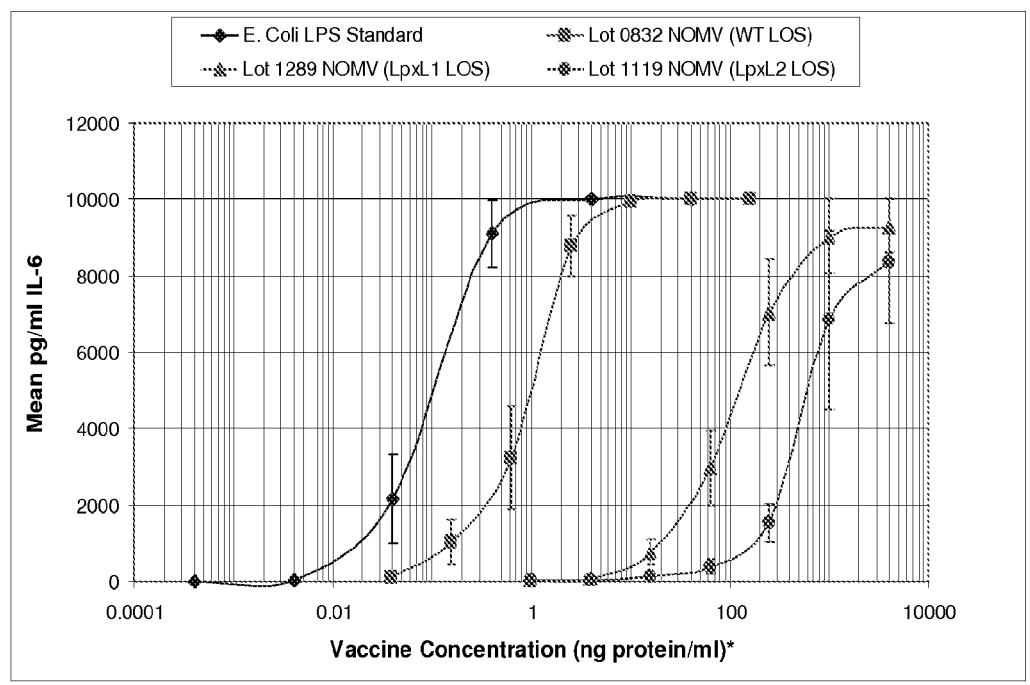
FIG. 10 is a graph depicting IL-6 release from human blood following incubation with different concentrations of the genetically modified NOMV vaccine.
Figure 11:
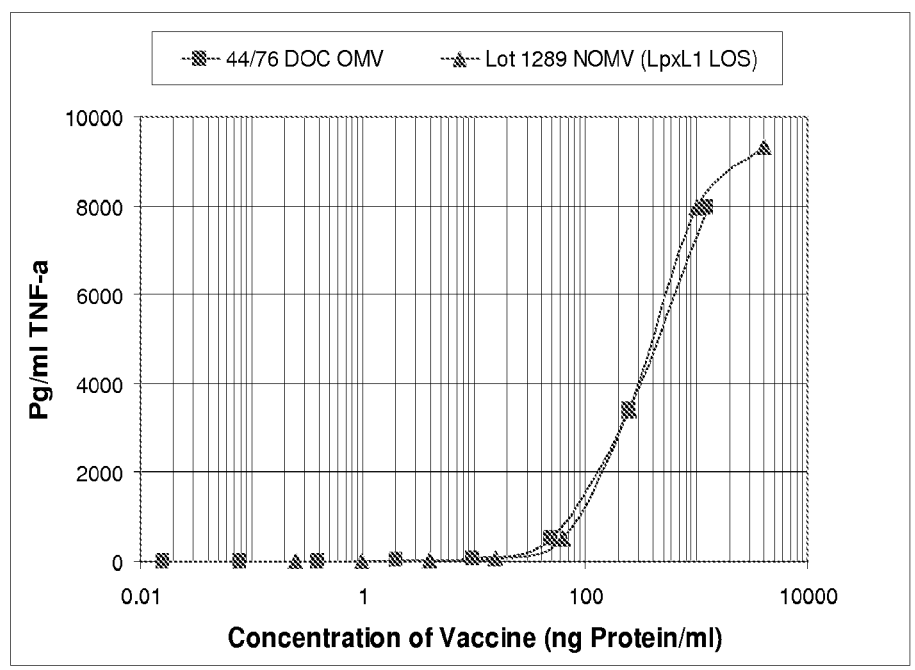
FIG. 11 is a graph depicting the TNF-α released from human blood after incubation with different concentrations of the genetically modified vaccine as compared with DOC-extracted OMV from strain 44/76.

The vaccine composition was further analyzed by sodium dodecyl sulfate polyacrylamide gel electrophoresis and western blotting. FIG. 6 depicts coomassie blue stained gel showing protein content in the vaccine (lane 4) as compared to control (lane 2) and filtered bulk lot (lane 3). FIG. 7 depicts silver stain gel showing the liposaccharide component of the vaccine (lane 3) as compared with control (ML5 LPS, land 1) and filtered bulk vaccine lot (lane 2). FIG. 8 depicts the results of identity testing of the vaccine for the major components of the NOMVs vaccine according to the antibodies as listed in Table 3.

TABLE 3

| Lane | Antibody Specificity | Monoclonal Antibody | Expected Reaction | Test Result |
|---|---|---|---|---|
| 1 | Pre-stained standard | NA | | |
| 2 | L8 LOS | 2-1 L8 | Trace | Trace |
| 3 | L8v LOS | 25-1-LC1 | Positive | Positive |
| 4 | L3, 7 LOS | 9-2-L379 | Trace | Trace |
| 5 | Lip (H8) | 2-1-CA2 | Positive | Positive |
| 6 | Opa P5.10 | 23-1-P5.10 | Negative | Negative |
| 7 | Opa P5.11 | MF7-1-P5.11 | Negative | Negative |
| 8 | Opc (P5.C) | B306-P5C | Positive | Positive |
| 9 | FHBP I (GNA1870) | JAR 4 | Positive | Positive |
| 10 | Rmp | 9F5 | Positive | Positive |
| 11 | PorB P4 | 15-1-P4 | Positive | Positive |
| 12 | PorA P1.14 | MN21G3.17 | Positive | Positive |
| 13 | PorA P1.15 | MN3C5C | Positive | Positive |
| 14 | PorA P1.19 | 2-1-P1.19 | Positive | Positive |
| 15 | TBP2 | 476C2G2 | Positive | Positive |
| 16 | Gp B Polysaccharide | 2-2-B | Negative | Negative |
| 17 | Amido Black Stain | NA | | |

The results are found in FIGS. 6, 7 and 8 showing proteins found in the NOMV of the vaccine from the genetically modified strain 8570 HOPS-G NOMV contain the proteins and LOS as described.

Example 4

General Safety Test of the Vaccine

The vaccine was tested in the General Safety Test as prescribed in 21 CFR 610.11. The results for the vaccine are given in Table 4.

TABLE 4

| Test Article | Test Result | Comments |
|---|---|---|
| 8570 HOPS-G NOMV Vaccine Lot # 1289 | Passed | All animals remained normal and healthy and gained weight |

Example 5

Rabbit Pyrogenicity Test*

The results of the rabbit pyrogen test for endotoxin activity are given in Table 3 for the genetically modified vaccine 8570 HOPS-G NOMV alone and the vaccine adsorbed to aluminum hydroxide adjuvant. The values given are the highest amounts tested that did not induce a fever in the rabbits (temperature increase of >0.5° C.), results of which are found in Table 5.

TABLE 5

| Test Article | Conc. Tested | Temperature Rise for Indicated Rabbit 1 | 2 | 3 |
|---|---|---|---|---|
| 8570 HOPS-G NOMV Vaccine Lot # 1289 | 0.4 pg/kg | 0.1 | 0.2 | 0.2 |

TABLE 5-continued

| Test Article | Conc. Tested | Temperature Rise for Indicated Rabbit 1 | 2 | 3 |
|---|---|---|---|---|
| 8570 HOPS-G NOMV Vaccine Lot # 1289 adsorbed to aluminum Rehydragel HPA lot # 1347 | 0.5 μg/kg | 0 | 0 | 0 |

* These tests were performed by BioReliance, Inc. under GLP following the protocol specified in the CFR.
** Amount of aluminum hydroxide/kg that will be used in the human study for all formulations (doses).

In summary, the vaccine alone passed at 0.4 pg/kg, the aluminum hydroxide adjuvant passed at 15 pg/kg (the largest amount per kg to be used in the clinical study), and the vaccine adsorbed to aluminum hydroxide passed at 0.5 lag/kg but failed at 1.0 pg/kg. Extrapolation of these results on a pg/kg basis suggest the adsorbed vaccine would be non-pyrogenic in humans up to a dose in the range of 25-50 μg.

Example 6

Cytokine Release from Whole Human Blood

The vaccine was tested for endotoxin content by measuring its ability to induce proinflammatory cytokines TNF-alpha and IL-6, from fresh whole human blood. The results are shown in FIGS. 9 and 10. The data are the mean of 3 (*E. Coli* LPS Standard and NOMV vaccine lot 1119 with lpxL2 LOS) or 5 (Lot 0832 NOMV with wild type LOS, and Lot 1289 NOMV vaccine with lpxL1 LOS) tests. The error bars are the standard error of the mean. The concentration of NOMV is based on protein but the *E. Coli* standard LPS is based on LPS by weight. Not to be bound by any particular theory, these results suggest that the current vaccine may have a similar safety profile in human volunteers as was seen with the lpxL2 LOS containing vaccine (Meningococcal 44/76 MOS 5D NOMV vaccine, Lot #1119, BB-IND 12687).

The activity of the 8570 HOPS-G NOMV Vaccine Lot #1289 was compared to the activity of deoxycholate extracted outer membrane vesicles (OMV). The vesicles were prepared using the basic method described by Fredriksen J H, et al. NIPH Annals, 14:67-80, 1991, except 0.5% deoxycholate (DOC) was used through out the procedure rather than using 1.2% DOC to resuspend the ultracentrifuge pellets. The results of this comparison are shown in FIG. 11.

Example 7

Immunogenicity in Mice and Bactericidal Antibody Response

Mice were given three doses of genetically modified vaccine strain 8570 HOPS-G at four week intervals with or without adsorption to aluminum hydroxide adjuvant (REHYDRAGEL® LV). Groups of 10 mice were vaccinated intraperitoneally at 0, 4 and 8 weeks with 0.1, 0.3, 1.0 or 3.0 μg of NOMV, the vaccine groups are listed in Table 6. Serum was taken at 0, 7 and 10 weeks. The sera were tested for bactericidal antibodies against four different strains, the parent of the vaccine strain and several related strains using normal human serum as a source of complement. Pre-vaccination sera were uniformly lacking in bactericidal activity.

TABLE 6

| Vaccine Group | Vaccine amount injected |
|---|---|
| 1 | 0.1 µg |
| 2 | 0.3 µg |
| 3 | 1.0 µg |
| 4 | 3.0 µg |
| 5 | 0.1 µg + Rehydragel LV |
| 6 | 0.3 µg + Rehydragel LV |
| 7 | 1.0 µg + Rehydragel LV |
| 8 | 3.0 µg + Rehydragel LV |
| 9 | 1.0 µg + Rehydragel HPA |

Figure 12:
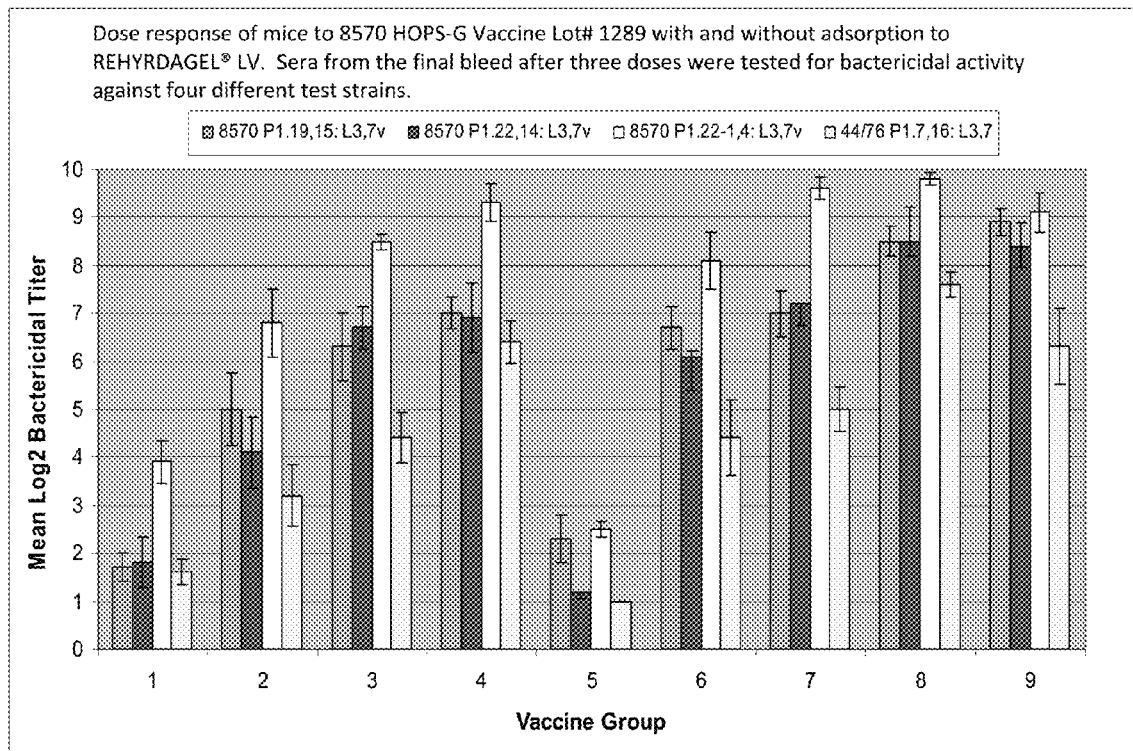
FIG. 12 is a bar graph depicting the bactericidal titers of mice vaccinated with different concentrations of the 8570 HOPS-G Vaccine with or without an adjuvant.

The results obtained with the 10-week sera (three doses of vaccine) are shown in FIG. 12 showing the bactericidal titer of the different vaccine groups for the genetically modified stains. Two of the test strains were isogenic with the parent of the vaccine strain. They were derived from the parent strain by replacing the porA gene with an alternate porA having a different serosubtype specificity. Two of the PorA proteins expressed in these test strains are present in the vaccine (P1.19,15 and P1.22,14), but the third (P1.22-1,4) is not. The fourth strain, 44/76, has a different PorA, a different PorB, and a different LOS core structure as compared to the vaccine strain. Surprisingly different to published studies in which deoxycholate extracted vesicle vaccines show the PorA antigen as typically the dominant antigen, the results of the vaccine of the present technology demonstrates that the majority of the bactericidal activity was not dependent on the serosubtype of the target strain and hence not against PorA.

Figure 13:
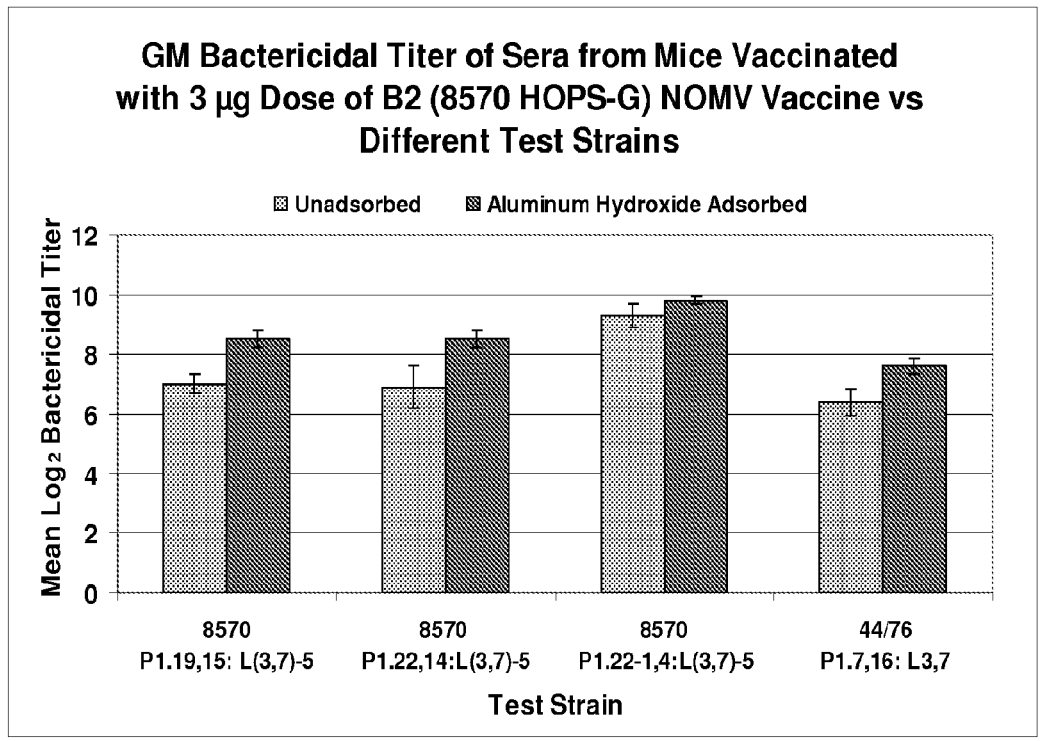
FIG. 13 is a bar graph depicting the bactericidal titer of mice vaccinated with 8570 HOPS-G Vaccine against different test strains.

Bactericidal antibodies induced in mice by the 8570 HOPS-G NOMV vaccine do not show serosubtype specificity, but appear mostly independent of serosubtype and serotype (FIG. 13). The antibodies killing strain 44/76 were found to be mainly directed against the LOS. Bars are standard error of the mean. The vaccine was administered with and without adsorption to REHYDRAGEL® LV aluminum hydroxide adjuvant.

Figure 14:
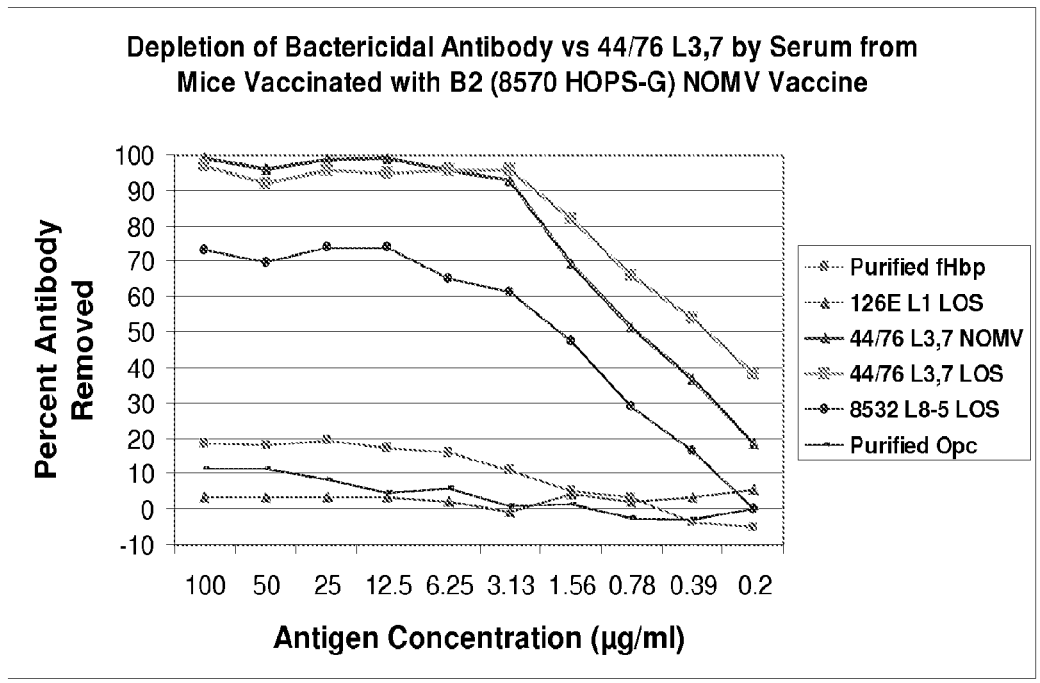
FIG. 14 is a graph depicting the results of the bactericidal antibody depletion assay for LOS, GNA1870, NOMV and Opc antigens.

Analysis of the specificity of the bactericidal antibody response against the heterologous strain 44/76 was undertaken by depletion of bactericidal activity with different isolated antigens. Post-vaccination mouse serum was diluted to the bactericidal endpoint (~50% killing) and incubated in 96-well microplate wells coated with different concentrations of several antigens. After 4-hrs incubation, the serum was tested for bactericidal activity and the percent removal of bactericidal antibody determined Purified LOS prepared from the target strain (immunotype L3,7) was able to remove nearly all the antibody. Purified LOS (immunotype L8v) prepared from the vaccine strain was able to remove about 70% of the antibody. The conserved protein GNA1870 (purified, recombinant protein) appeared to remove about 20% of the bactericidal activity, which, not to be bound by any particular theory, may indicate some cooperative killing involving both anti-LOS antibody and anti-GNA1870 antibody as shown in FIG. 14.

Example 8

Immunogenicity in Rabbits

Figure 15:
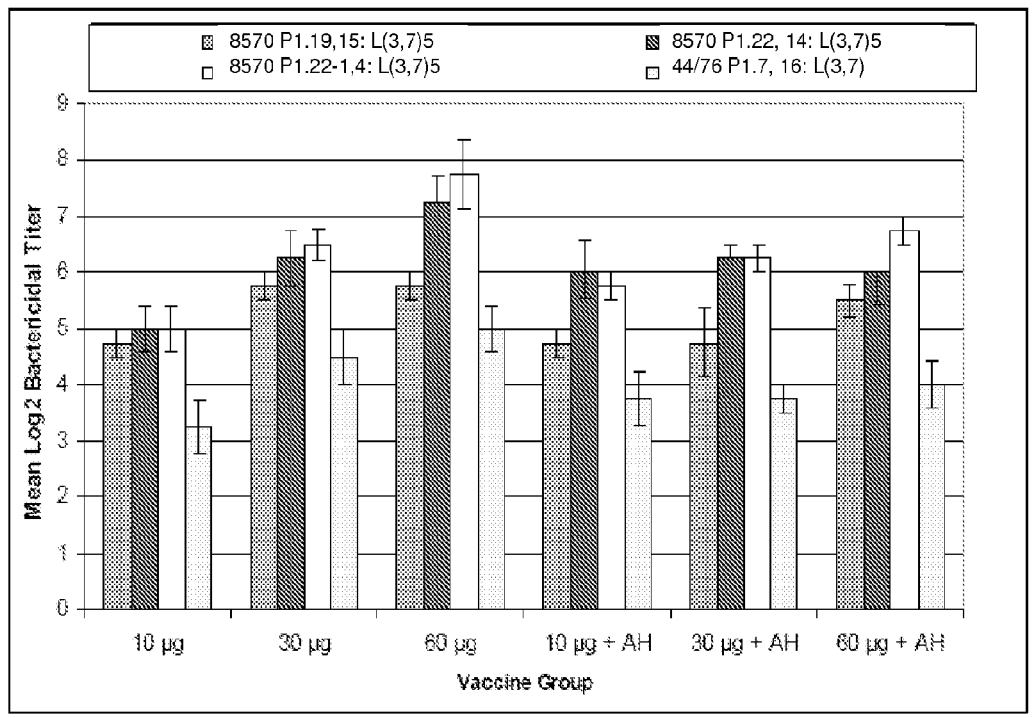
FIG. 15 depicts the antibody response of rabbits vaccinated with the 8570 HOPS-G NOMV vaccine with and without adjuvant.
Figure 16:
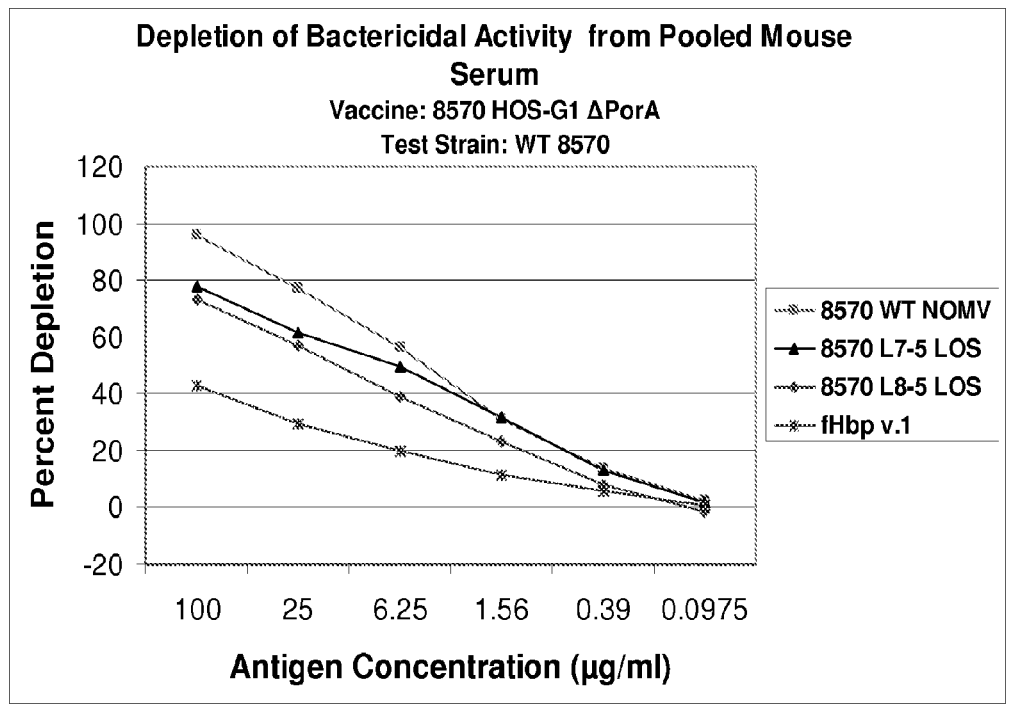
FIG. 16 is a graph depicting the results of an bactericidal depletion assay for test strains against the 8570 HOPS-G1 NOMV vaccine.

The vaccine was also tested for immunogenicity in rabbits. Groups of four rabbits were vaccinated intramuscularly with different doses of vaccine, with or without adsorption to aluminum hydroxide adjuvant. Three doses were given at six week intervals and blood was drawn two weeks after the last injection. The bactericidal antibody response of the rabbits to four test strains was determined. The test strains included 3 isogenic variants of 8570 expressing different PorA proteins and L3,7v LOS and strain 44/76 which has a heterologous PorA and LOS with a different core structure. PorA proteins P1.19,15 and P1.22,14 were present in the vaccine, but P1.22-1,4 was not. The results of the bactericidal tests are given in FIG. 15. Analysis of the cross reactive bactericidal activity toward strain 44/76 was analyzed in the same manner as for the mouse sera and the results were essentially the same. Most of the cross-reactive bactericidal antibodies could be removed by purified LOS homologous to the test strain Example 9

Preparation and Animal Testing of a Laboratory Lot of the Complete Multivalent NOMV Vaccine In addition to strain 8570 HOPS-G1 which was described in the Examples above, two additional vaccine strains were selected and genetically modified. The first was strain B 16B6 (B:2a:P 1.5,2:L2). This strain belongs to the genetic group ET-37 and has a class 2 PorB protein and type I transferrin binding protein B. The second was strain 44/76 (B:15:P1.7, 16:L3,7), which belongs to the genetic group ET-5 and is representative of the epidemic strain responsible for the group B meningococcal epidemic in Norway in the 1970's and 1980's. It expresses a class 3 PorB protein and type II transferrin binding protein B.

Strain B16B6 was genetically modified in much the same manner as described for strain 8570 HOPS-G1. Two genes were disabled, synX and lpxL1, to prevent capsule synthesis and sialylation of LOS and to reduce the toxicity of the LOS. A second porA gene (subtype P1.22-4) was inserted in place of the opaD gene. Variant 2 of GNA 1870 (FHBP) with the IPTG inducible E. coli Ptac promoter, was inserted in place of the nspA gene as a second copy using plasmid pBE-201 (Seq. ID. No 7). Plasmid pBE-201 (7687 b.p. for additional expression of fHBP (variant 2)) was constructed with the features as described in Table 7.

TABLE 7

| Feature | Coordinates (nt ###) | Source |
|---|---|---|
| pUC 19*) | 1-191 | New England Biolabs (NEB) |
| Sac I site (unique) | 192-197 | pUC19 |
| Uptake Sequence | 198-212 | PCR construct |
| 5' NspA NCR | 213-1248 | N. mening., 44-76, PCR construct |
| Bam H I site | 1249-1254 | Gent$^r$ gene cloning site |
| Gent$^r$ gene | 1255-2104 | PCR construct of Gent$^R$ gene |
| Sac II (unique) | 2105-2110 | PCR construct |
| Rmp promoter 5' fragment (rest) | 2111-2230 | N. mening., PCR construct |
| Mfe I site (unique) | 2231-2236 | PCR construct |
| Lac$^q$ operon | 2237-3641 | pMAL-p2X (New England Biolabs) |

TABLE 7-continued

| Feature | Coordinates (nt ##) | Source |
|---|---|---|
| Ptac promoter | 3642-3673 | pMAL-p2X, PCR construct |
| Lac operator | 3674-3702 | pMAL-p2X, PCR construct |
| RBS | 3750-3755 | pMAL-p2X, PCR construct |
| Nde I site (unique) | 3761-3766 | PCR construct |
| fHBP (variant 2) leader peptide | 3764-3823 | N. mening., 2996, PCR construct |
| fHBP (variant 2) ORF with stop codon | 3824-4588 | N. mening., 2996, PCR construct |
| SgrAI site (unique) | 4589-4596 | N. mening., 44-76, PCR construct |
| 3'NspA and 3'NspA NCR | 4597-4638 | Previous plasmid for NspA expression |
| rrnB transcription terminators | 4639-4945 | pBAD/Thio-E (Invitrogen), PCR |
| 3' NspA NCR | 4946-5432 | N. mening., PCR construct |
| Uptake Sequence | 5433-5447 | PCR construct |
| Hind III | 5448-5453 | pUC19 cloning site |
| pUC 19 | 5454-7687 end | NEB, (Amp.$^R$) |

*)Start from nt. 1 of pUC 19. The plasmid was modified to remove Nde I site for further convenient cloning as follow: It was digested by Nde I - EcoR I and 213 b.p. fragment was removed. Sticky ends were filled in and ligated to restore the plasmid. As a result sited Nde I (183) and EcoRI (395) were destroyed. For cloning of constructs for the expression of target protein we used Sac I and Hind III cloning sites of pUC 19.

A phase variant of the resulting strain expressing a truncated alpha chain consisting of glucose and galactose. L2 LOS was selected by colony blotting. The resulting genetically modified strain was designated B16B6 HPS-G2, see FIG. 18.

Strain 44/76 was also modified genetically in the same pattern as described for strain 8570 HOPS-G1. The two genes, synX and lpxL1, were disabled by insertion mutagenesis, a second porA gene (subtype P1.7-1, 1) was inserted along with its promoter in place of the opaD gene, and a second copy of nadA was inserted behind a porA promoter in place of the nspA gene. Plasmid pBE-311 was used for homologous recombination to insert the NadA gene, the plasmid 3-11 was constructed with the features as described in Table 8 and the sequence can be found in Seq. ID No. 8.

In addition, expression of OpcA was stabilized by curing the phase variation associated with its gene. This was done as described for strain 8570 HOPS-G1 by breaking up the poly-G string in its promoter in Example 1. The lgtA gene was interrupted as in Example 1 producing a truncated LOS. A phase variant of the resulting strain expressing the L8 immunotype was selected by colony blotting with an L8 specific monoclonal antibody. This genetically modified strain was designated 44/76 HOPS-D as shown in FIG. 18. The two additional strains were characterized to confirm stability of all the genetic modifications and stocks of each were frozen down.

Example 10

Preparation of NOMV Vaccine from Strains B16B6 HPS-G2 and 44/76 HOPS-D

The three genetically modified strains were used to prepare laboratory lots of NOMV vaccine compositions. The strains were grown in Catlin's modified medium as one liter cultures

TABLE 8

| Feature | Coordinates (nt ##) | Source |
|---|---|---|
| pUC19*) | 1-191 | New England Biolabs (NEB) |
| Sac I site (unique) | 192-197 | pUC19 cloning site |
| Uptake Sequence | 198-212 | PCR construct |
| 5' NspA NCR | 213-1248 | N. mening., 44-76, PCR construct |
| Bam H I site | 1249-1254 | Gent$^r$ gene cloning site |
| Gent$^r$ gene | 1255-2104 | PCR construct of Gent$^R$ gene |
| Sac II (unique) | 2105-2110 | PCR construct |
| PorA promoter (44-76) (modified)**) | 2111-3266 | N. mening., 44-76, PCR construct |
| Nde I site (unique) | 3267-3272 | PCR construct |
| NadA (allele 3) leader peptide | 3270-3338 | N. mening., 2996, PCR construct |
| NadA (allele 3) ORF with stop codon | 3339-4487 | N. mening., 2996, PCR construct |
| SgrAI site (unique) | 4488-4495 | N. mening., 44-76, PCR construct |
| PorA terminator (44-76) | 4496-4910 | N. mening., 44-76, PCR construct |
| Bsm I | 4911-4916 | PCR construct |
| 3' NspA NCR | 4917-5329 | N. mening., PCR construct |
| Uptake Sequence | 5330-5344 | PCR construct |
| Hind III | 5345-5350 | pUC19 cloning site |
| pUC 19 | 5351-7584 end | NEB, (Amp.$^R$) |

*)Start from nt. 1 of pUC 19. The plasmid was modified to remove Nde I site for further convenient cloning as follow: It was digested by Nde I - EcoR I and 213 b.p. fragment was removed. Sticky ends were filled in and ligated to restore the plasmid. As a result sited Nde I (183) and EcoRI (395) were destroyed. For cloning of constructs for the expression of target protein we used Sac I and Hind III cloning sites of pUC 19.
**)The 14Gs Poly G tract of the 44-76 promoter was modified by replacing with optimal for the expression 11Gs.

in Fernbach flasks on a rotary shaker. The cells were harvested by centrifugation, weighed and the cell paste frozen. The cell paste was thawed and used to prepare NOMV following essentially the same procedure as described for the clinical lot of vaccine from strain 8570 HOPS-G1 as described in Example 2. The process was scaled down and ultracentrifugation twice at 225,000×g for 60 min at 2-8° C. to remove nucleic acids and all soluble, non-vesicle material.

Example 11

Immunization of Mice with Complete Multivalent Vaccine

Groups of ten CD-1 mice were vaccinated intraperitoneally with two pg of NOMV vaccine from each genetically modified vaccine strain (6 pg total for the combined vaccine with NOMV from three strains). Three doses were given at 0, 4, and 8 weeks. Blood was drawn pre-vaccination and 2 weeks following the last vaccination (at 10 weeks).

Sera from individual mice were tested for bactericidal antibodies against the homologous strains, and pooled serum from each group of 10 mice was tested against a panel of 14 heterologous group B strains and 1 group C strain expressing a broad range of different subcapsular antigens.

The combined multivalent vaccine induced a geometric mean 1:256 titer against each of the three vaccine strains and a 4-fold or greater increase in bactericidal antibodies against 13 of the heterologous strains. Two of the test strains were not killed in spite of having an antigen shared with one of the vaccine strains. The bactericidal titers observed against the panel of strains are given in the Table 9.

TABLE 9

Bactericidal Titers of Pooled Mouse Sera against a Diverse Panel of Test Strains

| Bactericidal | | Titer of Pooled Serum from Mice Vaccinated with Indicated Vaccine | | | | |
|---|---|---|---|---|---|---|
| Test Strain | Antigens Expressed | B1 + B2 + B3 | B2 + B3 | B1 | B2 | B3 |
| 44/76 | B:15:P1.7,16:P5.11,C:L3,7 | 256 | 256 | 256 | 256 | 1 |
| 8570 | B:4:P1.19,15:P5.5:L3,7v | 256 | 256 | 256 | 256 | 2 |
| 816136 | B:2a:P1.5,2:P5.1a:L2 | 256 | 256 | 1 | 1 | 256 |
| 9162 | B:15:P1.7-2,3:P5.10,11:L3,7* | 16 | 16 | 8 | 2 | 1 |
| M1080 | B:1,19:P1.1:P5.3:L1,3,7 | 2 | 1 | 1 | 1 | 1 |
| 3576 | B:NT:P1.22-1:L3,7 | 128 | 128 | 4 | 2 | 16 |
| 8047 | B:2b:P1.5,2:L3,4,7 | 64 | 128 | 1 | 1 | 128 |
| 9547 | B:4:P1.4:L1 | 256 | 256 | 128 | 2 | 64 |
| 531 | B:2a:P1.5,2:P5.1a,1b,4,5:L3,7 | 256 | 256 | 256 | 1 | 256 |
| 7608 | B:2b:P1.5,2:P5.2,c:L4 | 256 | 128 | 1 | 1 | 128 |
| 6940 | B:8,19:P1.NT:L1 | 4 | 4 | 1 | 1 | 1 |
| 1901 | B:8,19:P1.NT:P5.C:L1,3,7 | 256 | 32 | 128 | 1 | 8 |
| 99M | B:2a:P1.2:P5.1a,1b,5:L3,7 | 512 | 512 | 16 | 8 | 256 |
| 6275 | B:2a:P1.2:P5.1a,4,5:L3,7 | — | 512 | 32 | 1 | 512 |
| 126E | C:8,19:P1.5,2:L1:P5.c | 256 | 256 | 4 | 2 | 64 |
| 2981 | B:8,19:P1.14:L1 | 32 | 8 | 4 | 64 | 2 |
| M4720 | B:19:P1.22,14:L2 | 1 | 1 | 1 | 1 | 1 |
| 6557 | B:17:P1.14:L1(3,7) | 32 | 16 | 1 | 32 | 16 |

Vaccine Code:
B1 = 44/76 HOPS-D NOMV
B2 = 8570 HOS-G1 NOMV
B3 = B16B6 HPS-G2 NOMV These results demonstrate the ability of the combined vaccine to induce bactericidal (protective) antibodies against a broad range of group B strains and potentially strains of other serogroups as well.

Analysis of the bactericidal antibodies using a bactericidal depletion test demonstrated that antibodies to all three sets of antigens were involved in killing at least some of the test strains. In some cases, it appeared that antibodies to more than one antigen were involved and acted together to produce bactericidal activity against a given strain.

Additional groups of mice were vaccinated with NOMV vaccine prepared from isogenic mutants of strain 8570 HOPS-G1. The mutant strains differed in their expression of PorA. Two mutants expressed a single PorA (one or the other of the two in the multivalent vaccine strain) and the third was a PorA knockout mutant expressing no PorA protein. Bactericidal titers induced by each of the four strains against several different test strains are shown in Table 10.

TABLE 10

| | Mutant of 8570 HOPS-G1 from Which NOMV Vaccine Was Prepared | | | |
|---|---|---|---|---|
| Test Strain | 8570 (P1.19, 15 and P1.22, 141 | 8570 (P1.19, 15) | 8570 (P1.22, 14) | 8570 APorA |
| 8570 | 256 | 256 | 256 | 256 |
| 44/76 | 256 | 256 | 256 | 256 |
| B16B6 | 1 | 1 | 1 | 1 |
| 3576 | 2 | 8 | 8 | 8 |
| 9547 | 2 | 4 | 4 | 2 |
| 2981 | 64 | 1 | 16 | 1 |
| 6557 | 32 | 1 | 128 | 1 |

For the first five test strains in Table 10, the PorA expression had no effect on the titer of bactericidal antibodies induced by the vaccine. For the last two strain, which both express P1.14, the presence of the P1.14 epitope in the vaccine correlated with the capacity of the respective serum to kill the strain. This demonstrates that antibodies to PorA are involved in the observed killing for some strains. For other strains such as the homologous strain and strain 44/76 other antigens are responsible for most of the bactericidal activity. This was demonstrated by analysis with the bactericidal depletion assay. Results of one such assay are given in FIG. 16. The results shown in FIG. 17 demonstrate that antibodies to LOS and FHBP (GNA1870) were involved in the killing of strain 8570 by antiserum to PorA knockout mutant of 8570 HOPS-G1.

The invention claimed is:

1. A vaccine composition comprising native outer membrane vesicles (NOMVs) isolated from at least two genetically modified meningococcal strains, wherein the NOMVs include different sets of antigens comprising different meningococcal Porin A (PorA) proteins, meningococcal lipooligosaccharides, and at least one conserved meningococcal outer membrane protein, wherein the genetically modified meningococcal strains are modified to comprise inactivation of its lpxL1, synX, and lgtA genes, wherein at least one of the at least two meningococcal strains is genetically modified to express at least two different meningococcal PorA subtype proteins or at least two different meningococcal PorA subtype epitopes, wherein the genetic modification includes insertion of a second porA gene in place of the opaD gene of the at least one meningococcal strain.

2. The vaccine composition of claim 1, wherein the lipooligosaccharides have a different core structure and have an alpha chain consisting of glucose and galactose.

3. The vaccine composition of claim 1, wherein each of the at least two genetically modified meningococcal strains expresses the at least two different PorA subtype proteins or the at least two different PorA subtype epitopes which are chosen based on the most prevalent of PorA subtypes among serogroup B case isolates of Neisseria meningitidis.

4. The vaccine composition of claim 1, wherein the at least one conserved meningococcal outer membrane protein is overexpressed in each of the at least two meningococcal strains, wherein the at least one conserved meningococcal outer membrane protein is selected from the group consisting of variant 1 factor H binding protein (FHBP), variant 2 FHBP, variant 3 FHBP, NadA, NspA, transferrin binding protein A (TbpA), and transferrin binding protein B (TbpB).

5. The vaccine composition of claim 1, wherein the NOMVs are prepared from packed cells of the genetically modified meningococcal strain or from their spent culture medium without exposure to a detergent or denaturing solvents.

6. The vaccine composition of claim 1, wherein the vaccine composition comprises 5% glucose as an excipient.

7. The vaccine composition of claim 1, wherein the NOMVs are combined with an adjuvant selected from the group consisting of aluminum hydroxide, aluminum phosphate, MF 59, CpG-ODN, and monophosphoryl lipid A.

8. The vaccine composition of claim 1, wherein the inactivation of the lgtA gene in each of the at least two meningococcal strains results in expression of a truncated lipooligosaccharide that lacks lacto-N-neotetraose tetrasaccharide.

9. The vaccine composition of claim 3, wherein the most prevalent PorA subtypes among the serogroup B case isolates of the Neisseria meningitidis are selected from the group consisting of P1.7-1,1; P1.22,14; and P1.22-1,4.

10. A method of eliciting an immune response against serogroup B Neisseria meningitidis in a mammal comprising administering intramuscularly and/or intranasally a dose of the vaccine of claim 1 to said mammal.

* * * * *